(12) United States Patent
Um et al.

(10) Patent No.: US 12,433,154 B2
(45) Date of Patent: Sep. 30, 2025

(54) ELECTROLUMINESCENCE DEVICE

(71) Applicant: Samsung Display Co., Ltd., Yongin-si (KR)

(72) Inventors: Hyunah Um, Seoul (KR); Hyeongmin Kim, Suwon-si (KR); Heechoon Ahn, Seoul (KR); Yeseul Lee, Busan (KR); Hyoyoung Lee, Suwon-si (KR); Yirang Im, Anseong-si (KR); Seowon Cho, Anyang-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 1045 days.

(21) Appl. No.: 17/444,342

(22) Filed: Aug. 3, 2021

(65) Prior Publication Data

US 2022/0140255 A1 May 5, 2022

(30) Foreign Application Priority Data

Nov. 4, 2020 (KR) .................... 10-2020-0145766

(51) Int. Cl.
*H01L 51/50* (2006.01)
*C07D 213/06* (2006.01)
(Continued)

(52) U.S. Cl.
CPC ......... *H10K 85/626* (2023.02); *C07D 213/06* (2013.01); *H10K 85/40* (2023.02);
(Continued)

(58) Field of Classification Search
None
See application file for complete search history.

(56) References Cited

U.S. PATENT DOCUMENTS 9,559,309 B2   1/2017   Min et al.
10,227,528 B2   3/2019   Jatsch et al.
(Continued)

FOREIGN PATENT DOCUMENTS

KR   10-1247626 B1   3/2013
KR   2014130297   *   9/2014   ............ H01L 51/50
(Continued)

*Primary Examiner* — Gregory D Clark
(74) *Attorney, Agent, or Firm* — Womble Bond Dickinson (US) LLP

(57) ABSTRACT

An electroluminescence device of the present disclosure includes a first electrode, a second electrode facing the first electrode, and a plurality of organic layers between the first electrode and the second electrode, wherein at least one organic layer selected from among the plurality of organic layers includes a polycyclic compound represented by Formula 1, thereby showing improved emission efficiency:

Formula 1

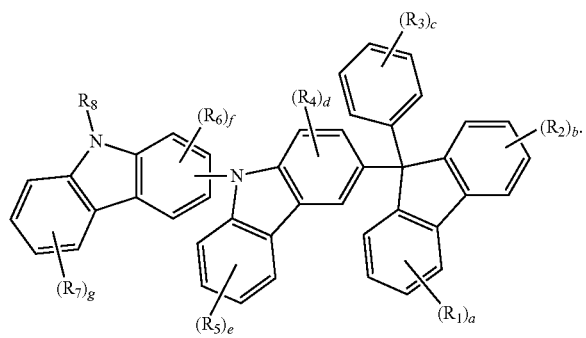

20 Claims, 6 Drawing Sheets

(51) Int. Cl.
  *H10K 85/40* (2023.01)
  *H10K 85/60* (2023.01)
  *C07C 15/20* (2006.01)
  *C09K 11/06* (2006.01)
  *H10K 50/11* (2023.01)
  *H10K 71/00* (2023.01)

(52) U.S. Cl.
  CPC ..... *H10K 85/6572* (2023.02); *H10K 85/6574* (2023.02); *H10K 85/6576* (2023.02); *C07C 15/20* (2013.01); *C09K 11/06* (2013.01); *H10K 50/11* (2023.02); *H10K 71/00* (2023.02)

(56) References Cited

U.S. PATENT DOCUMENTS

| | | | |
|---|---|---|---|
| 10,388,889 | B2 | 8/2019 | Ahn et al. |
| 2019/0131543 | A1 | 5/2019 | Lee et al. |
| 2020/0073605 | A1 | 3/2020 | Tanaka |
| 2020/0403165 | A1* | 12/2020 | Park .................... H10K 85/615 |

FOREIGN PATENT DOCUMENTS

| | | |
|---|---|---|
| KR | 10-1531612 B1 | 6/2015 |
| KR | 10-2015-0100825 A | 9/2015 |
| KR | 10-2018-0011910 A | 2/2018 |
| KR | 10-2110983 B1 | 5/2020 |
| WO | WO 2020/073605 A1 | 4/2020 |

* cited by examiner

ELECTROLUMINESCENCE DEVICE

CROSS-REFERENCE TO RELATED APPLICATIONS

This application claims priority to and the benefit of Korean Patent Application No. 10-2020-0145766, filed on Nov. 4, 2020, in the Korean Intellectual Property Office, the entire content of which is hereby incorporated by reference.

BACKGROUND

1. Field

One or more embodiments of the present disclosure herein relate to an electroluminescence device, and more particularly, to an electroluminescence device including a polycyclic compound used as a light-emitting material.

2. Description of Related Art

Recently, the development of an organic electroluminescence display as an image display is being actively conducted. The organic electroluminescence display is different from a liquid crystal display and is a self-luminescent display in which holes and electrons injected from a first electrode and a second electrode recombine in an emission layer so that a light-emitting material including an organic compound in the emission layer emits light to achieve display of images.

In the application of an electroluminescence device to a display, the decrease of a driving voltage, and the increase of the emission efficiency and the life of the electroluminescence device are required (or desired), and development of materials for an electroluminescence device stably (or suitably) achieving these characteristics is being continuously required (or desired).

SUMMARY

One or more aspects of embodiments of the present disclosure are directed toward an electroluminescence device with high efficiency.

One or more embodiments of the present disclosure provides an electroluminescence device including: a first electrode; a second electrode opposite (e.g., facing) the first electrode; and a plurality of organic layers between the first electrode and the second electrode, wherein at least one organic layer selected from among the plurality of organic layers includes a polycyclic compound, and the polycyclic compound includes: a substituted or unsubstituted fluorene group; a substituted or unsubstituted phenyl group connected with a carbon atom at position 9 of the substituted or unsubstituted fluorene group; a substituted or unsubstituted first carbazole group connected with the carbon atom at position 9 of the substituted or unsubstituted fluorene group; and a substituted or unsubstituted second carbazole group connected with a nitrogen atom of the substituted or unsubstituted first carbazole group.

In one or more embodiments, the substituted or unsubstituted phenyl group may be directly connected with the carbon atom at position 9 of the substituted or unsubstituted fluorene group.

In one or more embodiments, the substituted or unsubstituted first carbazole group may be directly connected with the carbon atom at position 9 of the substituted or unsubstituted fluorene group.

In one or more embodiments, the substituted or unsubstituted second carbazole group may be directly connected with the nitrogen atom of the substituted or unsubstituted first carbazole group.

In one or more embodiments, a substituted or unsubstituted third carbazole group may be connected with a nitrogen atom of the substituted or unsubstituted second carbazole group.

In one or more embodiments, the substituted or unsubstituted phenyl group and the substituted or unsubstituted first carbazole group may not form a ring with each other.

In one or more embodiments, the plurality of organic layers may include a hole transport region, an emission layer, and an electron transport region, and the polycyclic compound may be included in the emission layer.

In one or more embodiments, the emission layer may emit at least one of fluorescence, phosphorescence, or thermally activated delayed fluorescence.

In one or more embodiments, the emission layer may include a host and a dopant, and the host may include the polycyclic compound.

In one or more embodiments, the emission layer may emit light having a central wavelength of about 420 nm to about 470 nm.

BRIEF DESCRIPTION OF THE FIGURES

The accompanying drawings are included to provide a further understanding of the present disclosure and are incorporated in and constitute a part of this specification. The drawings illustrate embodiments of the present disclosure and, together with the description, serve to explain principles of the present disclosure. In the drawings.

DETAILED DESCRIPTION

Figure 1:
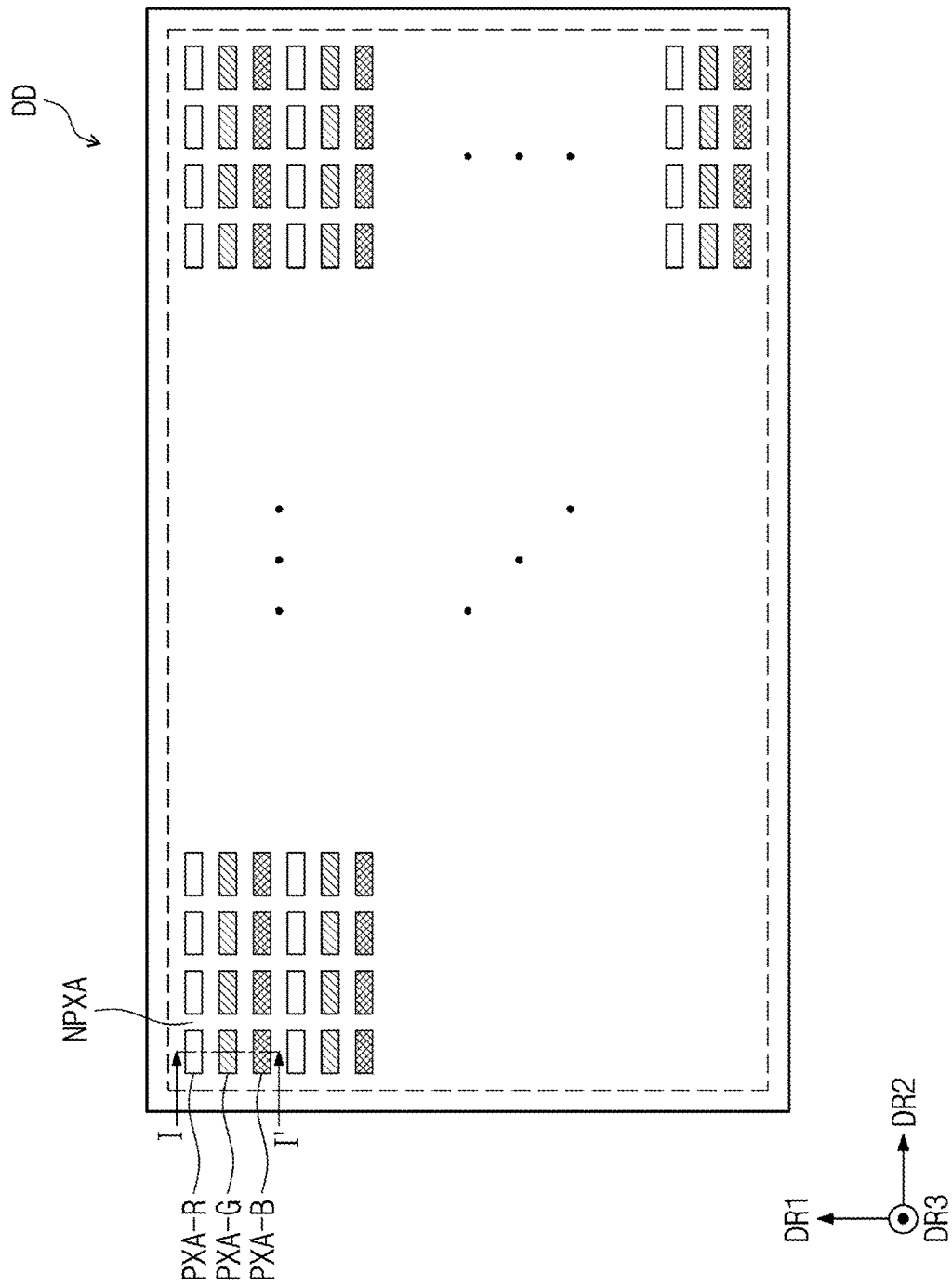
FIG. 1 is a plan view of a display apparatus of one or more embodiments.

The present disclosure may have various modifications and may be embodied in different forms, and embodiments will be explained in more detail with reference to the accompany drawings. The present disclosure may, however, be embodied in different forms and should not be construed as limited to the embodiments set forth herein. Rather, all modifications, equivalents, and substituents which are included in the spirit and technical scope of the present disclosure should be included in the present disclosure.

Like reference numerals refer to like elements throughout. In the drawings, the dimensions of structures are exaggerated for clarity of illustration. It will be understood that, although the terms first, second, etc. may be used herein to describe various elements, these elements should not be limited by these terms. These terms are only used to distinguish one element from another element. For example, a first element could be termed a second element without departing from the teachings of the present disclosure. Similarly, a second element could be termed a first element. As used herein, the singular forms are intended to include the plural forms as well, unless the context clearly indicates otherwise.

In the description, it will be further understood that the terms "comprises" and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof.

In the description, it will also be understood that when a layer, a film, a region, a plate, etc. is referred to as being "on" or "above" another part, it can be "directly on" the other part (without any intervening layers therebetween), or intervening layers may also be present. Similarly, it will also be understood that when a layer, a film, a region, a plate, etc. is referred to as being "under" or "below" another part, it can be "directly under" the other part (without any intervening layers therebetween), or intervening layers may also be present. Also, when an element is referred to as being disposed "on" another element, it can be disposed under the other element.

In the description, the term "substituted or unsubstituted" corresponds to a group that is unsubstituted or that is substituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkynyl group, an alkoxy group, a hydrocarbon ring group, an aryl group, and a heterocyclic group. In addition, each of the substituents may be substituted or unsubstituted. For example, a biphenyl group may be interpreted as an aryl group or a phenyl group substituted with a phenyl group.

In the description, the term "forming a ring via the combination with an adjacent group" may mean forming a substituted or unsubstituted hydrocarbon ring, or a substituted or unsubstituted heterocycle via the combination with an adjacent group. The hydrocarbon ring includes an aliphatic hydrocarbon ring and an aromatic hydrocarbon ring. The heterocycle includes an aliphatic heterocycle and an aromatic heterocycle. The hydrocarbon ring and the heterocycle may be monocyclic rings or polycyclic rings. In addition, the ring formed via the combination with an adjacent group may be combined with another ring to form a spiro structure.

In the description, the term "adjacent group" may mean a pair of substituent groups where the first substituent is connected to an atom which is directly connected to another atom substituted with the second substituent; a pair of substituent groups connected to the same atom; or a pair of substituent groups where the first substituent is sterically positioned at the nearest position to the second substituent. For example, in 1,2-dimethylbenzene, two methyl groups may be interpreted as "adjacent groups" to each other, and in 1,1-diethylcyclopentene, two ethyl groups may be interpreted as "adjacent groups" to each other.

In the description, the halogen atom may be a fluorine atom, a chlorine atom, a bromine atom, or an iodine atom.

In the description, the alkyl (e.g., alkyl group) may be a linear, branched or cyclic alkyl group. The carbon number of the alkyl may be 1 to 50, 1 to 30, 1 to 20, 1 to 10, or 1 to 6. Examples of the alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, the hydrocarbon ring group may mean an optional functional group or substituent derived from an aliphatic hydrocarbon ring. The hydrocarbon ring group may be a saturated hydrocarbon ring group of 5 to 20 carbon atoms for forming a ring.

In the description, the aryl group may mean an optional functional group or substituent derived from an aromatic hydrocarbon ring. The aryl group may be a monocyclic aryl group or a polycyclic aryl group. The carbon number for forming rings in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinquephenyl, sexiphenyl, triphenylenyl, pyrenyl, benzofluoranthenyl, chrysenyl, etc., without limitation.

In the description, the fluorenyl group may be substituted, and two substituents may be combined with each other to form a spiro structure. Examples of a substituted fluorenyl group may be as follows. However, embodiments of the present disclosure are not limited thereto.

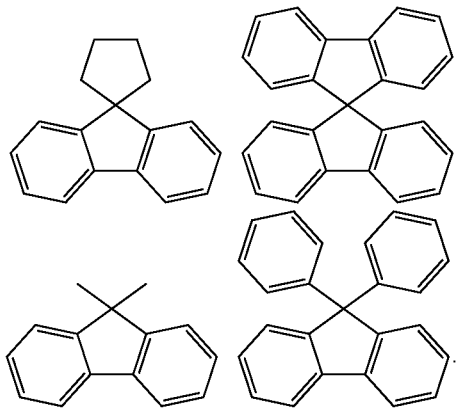

In the description, the heterocyclic group may mean an optional functional group or substituent derived from a ring including one or more among B, O, N, P, Si and S as heteroatoms. The heterocyclic group includes an aliphatic heterocyclic group and an aromatic heterocyclic group. The aromatic heterocyclic group may be a heteroaryl group. An aliphatic heterocycle (e.g., an aliphatic heterocyclic group) and aromatic heterocycle (e.g., an aromatic heterocyclic group) may be a monocycle or a polycycle.

In the description, the heterocyclic group may include one or more among B, O, N, P, Si and S as heteroatoms. If the heterocyclic group includes two or more heteroatoms, two or more heteroatoms may be the same or different. The heterocyclic group may be a monocyclic heterocyclic group or a polycyclic heterocyclic group, and includes a heteroaryl group. The carbon number for forming rings of the heterocyclic group may be 2 to 30, 2 to 20, or 2 to 10.

In the description, the aliphatic heterocyclic group may include one or more among B, O, N, P, Si and S as heteroatoms. The carbon number for forming rings of the aliphatic heterocyclic group may be 2 to 30, 2 to 20, or 2 to 10. Examples of the aliphatic heterocyclic group may include an oxirane group, a thiirane group, a pyrrolidine group, a piperidine group, a tetrahydrofuran group, a tetrahydrothiophene group, a thiane group, a tetrahydropyran group, a 1,4-dioxane group, etc., without limitation.

In the description, the heteroaryl group may include one or more among B, O, N, P, Si and S as heteroatoms. If the heteroaryl group includes two or more heteroatoms, two or more heteroatoms may be the same or different. The heteroaryl group may be a monocyclic heteroaryl group or a polycyclic heteroaryl group. The carbon number for forming rings of the heteroaryl group may be 2 to 30, 2 to 20, or 2 to 10. Examples of the heteroaryl group may include thiophene, furan, pyrrole, imidazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxazole, oxadiazole, thiadiazole, phenothiazine, dibenzosilole, dibenzofuran, etc., without limitation.

In the description, the explanation for the aryl group may be applied to the arylene group except that the arylene group is a divalent group. The explanation for the heteroaryl group may be applied to the heteroarylene group except that the heteroarylene group is a divalent group.

In the description, the silyl group may include an alkyl silyl group and an aryl silyl group. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc. However, embodiments of the present disclosure are not limited thereto.

In the description, the carbon number of a carbonyl group is not specifically limited, but the carbon number may be 1 to 40, 1 to 30, or 1 to 20. For example, the carbonyl group may be selected from the structures below, but is not limited thereto:

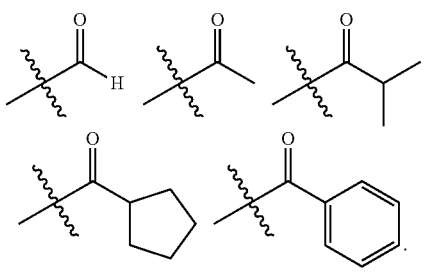

In the description, the boron group may mean the above-defined alkyl group or aryl group which is combined with a boron atom. The boron group includes an alkyl boron group and an aryl boron group. Examples of the boron group may include a trimethylboron group, a triethylboron group, a t-butyldimethylboron group, a triphenylboron group, a diphenylboron group, a phenylboron group, etc., without limitation.

In the description, the alkenyl group may be a linear or branched chain alkenyl group. The carbon number thereof is not specifically limited, but may be 2 to 30, 2 to 20, or 2 to 10. Examples of the alkenyl group may include a vinyl group, a 1-butenyl group, a 1-pentenyl group, a 1,3-butadienyl aryl group, a styrenyl group, a styrylvinyl group, etc., without limitation.

In the description, the carbon number of the amine group is not specifically limited, but may be 1 to 30. The amine group may include an alkyl amine group, and an aryl amine group. Examples of the amine group may include a methylamine group, a dimethylamine group, a phenylamine group, a diphenylamine group, a naphthylamine group, a 9-methyl-anthracenylamine group, a triphenylamine group, etc., without limitation.

In the description, the alkyl group in an alkylthio group, an alkylsulfoxy group, an alkylaryl group, an alkyl boron group, an alkyl silyl group, and an alkyl amine group is the same as the above-described alkyl group.

In the description, the aryl group in an aryloxy group, an arylthio group, an arylsulfoxy group, an aryl boron group, an aryl silyl group, and an aryl amine group is the same as the above-described aryl group.

In the description, the direct linkage may mean a single bond.

Meanwhile, in the description, "⁃⁃" and "———*" mean positions to be connected (e.g., binding sites).

In the description, "carbon number for forming rings" may refer to ring-forming carbon atoms.

Hereinafter, embodiments of the present disclosure will be explained with reference to attached drawings.

Figure 2:
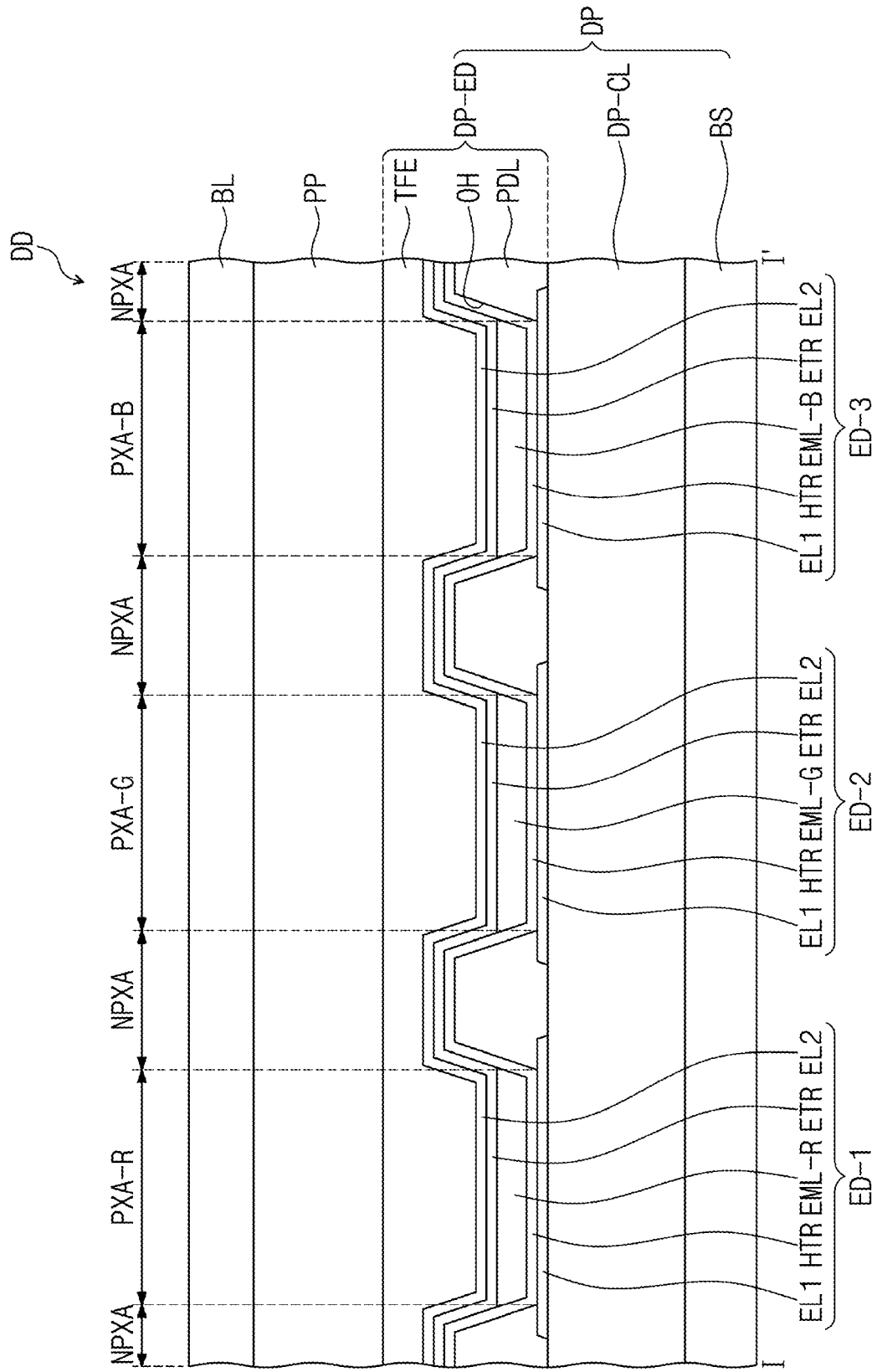
FIG. 2 is a cross-sectional view of a display apparatus of one or more embodiments.

FIG. 1 is a plan view showing one or more embodiments of a display apparatus DD. FIG. 2 is a cross-sectional view of a display apparatus DD of one or more embodiments. FIG. 2 is a cross-sectional view showing a part corresponding to line I-I' in FIG. 1.

The display apparatus DD may include a display panel DP and an optical layer PP positioned on the display panel DP. The display panel DP includes electroluminescence devices ED-1, ED-2 and ED-3. The display apparatus DD may include multiple electroluminescence devices ED-1, ED-2 and ED-3. The optical layer PP is positioned on the display panel DP and may control external light reflected by the display panel DP. The optical layer PP may include, for example, a polarization layer or a color filter layer. In one or more embodiments, the optical layer PP in the display apparatus DD of one or more embodiments may be omitted.

On the optical layer PP, a base substrate BL may be disposed (e.g., positioned). The base substrate BL may be a member providing a base surface where the optical layer PP is disposed. The base substrate BL may be a glass substrate, a metal substrate, a plastic substrate, etc. However, embodiments of the present disclosure are not limited thereto, and the base substrate BL may be an inorganic layer, an organic layer and/or a composite material layer. In one or more embodiments, the base substrate BL may be omitted.

The display apparatus DD according to one or more embodiments may further include a plugging layer. The plugging layer may be disposed (e.g., provided) between the display device layer DP-ED and the base substrate BL. The plugging layer may be an organic material layer. The plugging layer may include at least any one selected from among an acrylic resin, a silicon-based resin, and an epoxy-based resin.

The display panel DP may include a base layer BS, a circuit layer DP-CL provided on the base layer BS and a display device layer DP-ED. The display device layer DP- ED may include a pixel definition layer PDL, electroluminescence devices ED-1, ED-2 and ED-3 disposed between portions of the pixel definition layers PDL, and an encapsulating layer TFE disposed on the electroluminescence devices ED-1, ED-2 and ED-3.

The base layer BS may be a member providing a base surface where the display device layer DP-ED is disposed. The base layer BS may be a glass substrate, a metal substrate, a plastic substrate, etc. However, embodiments of the present disclosure are not limited thereto, and the base layer BS may be an inorganic layer, an organic layer and/or a composite material layer.

In one or more embodiments, the circuit layer DP-CL is disposed on the base layer BS, and the circuit layer DP-CL may include multiple transistors. Each of the transistors may include a control electrode, an input electrode, and an output electrode. For example, the circuit layer DP-CL may include switching transistors and driving transistors for driving the electroluminescence devices ED-1, ED-2 and ED-3 of the display device layer DP-ED.

Each of the electroluminescence devices ED-1, ED-2 and ED-3 may have the structure of an electroluminescence device ED of one or more embodiments according to FIG. 3 to FIG. 6, which will be explained in more detail below. Each of the electroluminescence devices ED-1, ED-2 and ED-3 may include a first electrode EL1, a hole transport region HTR, a corresponding one of emission layers EML-R, EML-G and EML-B, an electron transport region ETR, and a second electrode EL2.

In FIG. 2, shown is an embodiment where the emission layers EML-R, EML-G and EML-B of the electroluminescence devices ED-1, ED-2 and ED-3 are disposed in opening portions OH defined in the pixel definition layer PDL, and the hole transport region HTR, the electron transport region ETR and the second electrode EL2 are provided as common layers in all of the electroluminescence devices ED-1, ED-2 and ED-3. However, embodiments of the present disclosure are not limited thereto. In one or more embodiments, the hole transport region HTR and the electron transport region ETR may be patterned and provided in the opening portions OH defined in the pixel definition layer PDL. For example, in one or more embodiments, the hole transport region HTR, the emission layers EML-R, EML-G and EML-B, and the electron transport region ETR of the electroluminescence devices ED-1, ED-2 and ED-3 may be patterned by an ink jet printing method and provided.

The encapsulating layer TFE may cover the electroluminescence devices ED-1, ED-2 and ED-3. The encapsulating layer TFE may encapsulate the display device layer DP-ED. The encapsulating layer TFE may be a thin film encapsulating layer. The encapsulating layer TFE may be one layer or a stacked structure of multiple layers. The encapsulating layer TFE may include at least one insulating layer. The encapsulating layer TFE according to one or more embodiments may include at least one inorganic layer (hereinafter, encapsulating inorganic layer). In one or more embodiments, the encapsulating layer TFE may include at least one organic layer (hereinafter, encapsulating organic layer) and at least one encapsulating inorganic layer.

The encapsulating inorganic layer protects the display device layer DP-ED from moisture/oxygen, and the encapsulating organic layer protects the display device layer DP-ED from foreign materials such as dust particles. The encapsulating inorganic layer may include silicon nitride, silicon oxy nitride, silicon oxide, titanium oxide, and/or aluminum oxide, without specific limitation. The encapsulating organic layer may include an acrylic compound, an epoxy-based compound, etc. The encapsulating organic layer may include a photopolymerizable organic material, without specific limitation.

The encapsulating layer TFE may be disposed on the second electrode EL2 and may plug (e.g., fill and/or cover) the opening portion OH.

Referring to FIG. 1 and FIG. 2, the display apparatus DD may include a non-luminous area NPXA and luminous areas PXA-R, PXA-G and PXA-B. The luminous areas PXA-R, PXA-G and PXA-B may be areas emitting (e.g., to emit) light produced from the electroluminescence devices ED-1, ED-2 and ED-3, respectively. The luminous areas PXA-R, PXA-G and PXA-B may be separated from each other on a plane (e.g., in plan view).

The luminous areas PXA-R, PXA-G and PXA-B may be areas separated by the pixel definition layer PDL. The non-luminous areas NPXA may be areas positioned among (e.g., between) neighboring luminous areas PXA-R, PXA-G and PXA-B and may be areas corresponding to the pixel definition layer PDL. Meanwhile, in the disclosure, each of the luminous areas PXA-R, PXA-G and PXA-B may correspond to each pixel. The pixel definition layer PDL may divide (e.g., separate) the electroluminescence devices ED-1, ED-2 and ED-3. The emission layers EML-R, EML-G and EML-B of the electroluminescence devices ED-1, ED-2 and ED-3 may be disposed and divided (e.g., separated from each other) in the opening portions OH defined in the pixel definition layer PDL.

The luminous areas PXA-R, PXA-G and PXA-B may be divided into numbers of groups according to the color of light produced from the electroluminescence devices ED-1, ED-2 and ED-3. In the display apparatus DD of one or more embodiments, shown in FIG. 1 and FIG. 2, three luminous areas PXA-R, PXA-G and PXA-B emitting (e.g., to emit) red light, green light and blue light are illustrated as an example. For example, the display apparatus DD of one or more embodiments may include a red luminous area PXA-R, a green luminous area PXA-G and a blue luminous area PXA-B, which are separated from each other.

In the display apparatus DD according to one or more embodiments, multiple electroluminescence devices ED-1, ED-2 and ED-3 may emit light having different wavelength regions. For example, in one or more embodiments, the display apparatus DD may include a first electroluminescence device ED-1 emitting (e.g., to emit) red light, a second electroluminescence device ED-2 emitting (e.g., to emit) green light, and a third electroluminescence device ED-3 emitting (e.g., to emit) blue light. That is, the red luminous area PXA-R, the green luminous area PXA-G, and the blue luminous area PXA-B of the display apparatus DD may correspond to the first electroluminescence device ED-1, the second electroluminescence device ED-2, and the third electroluminescence device ED-3, respectively.

However, embodiments of the present disclosure are not limited thereto, and the first to third electroluminescence devices ED-1, ED-2 and ED-3 may emit light in the same wavelength region, or at least one thereof may emit light in a different wavelength region. For example, all the first to third electroluminescence devices ED-1, ED-2 and ED-3 may emit blue light.

The luminous areas PXA-R, PXA-G and PXA-B in the display apparatus DD according to one or more embodiments may be arranged in a stripe shape or stripe pattern. Referring to FIG. 1, multiple red luminous areas PXA-R, multiple green luminous areas PXA-G and multiple blue luminous areas PXA-B may be arranged along a second directional axis DR2. For example, multiple red luminous areas PXA-R may be arranged with each other along the second directional axis DR2, multiple green luminous areas PXA-G may be arranged with each other along the second directional axis DR2, and multiple blue luminous areas PXA-B may be arranged with each other along the second directional axis DR2. In addition, a red luminous area PXA-R, a green luminous area PXA-G and a blue luminous area PXA-B may be arranged alternatingly with each other along a first directional axis DR1.

In FIG. 1 and FIG. 2, the areas of the luminous areas PXA-R, PXA-G and PXA-B are shown to be similar, but embodiments of the present disclosure are not limited thereto. The areas of the luminous areas PXA-R, PXA-G and PXA-B may be different from each other according to the wavelength region of light emitted therefrom. As used herein, the areas of the luminous areas PXA-R, PXA-G and PXA-B may mean areas on a plane defined by the first directional axis DR1 and the second directional axis DR2.

The arrangement type of the luminous areas PXA-R, PXA-G and PXA-B is not limited to the configuration shown in FIG. 1, and the arrangement order of the red luminous areas PXA-R, the green luminous areas PXA-G and the blue luminous areas PXA-B may be provided in various suitable combinations according to the properties of display quality required (or desired) for the display apparatus DD. For example, the arrangement of the luminous areas PXA-R, PXA-G and PXA-B may be a PenTile®/PEN-TILE® arrangement (PENTILE® is a registered trademark owned by Samsung Display Co., Ltd.), or a diamond arrangement.

In some embodiments, the areas of the luminous areas PXA-R, PXA-G and PXA-B may be different from each other. For example, in one or more embodiments, the area of the green luminous area PXA-G may be smaller than the area of the blue luminous area PXA-B, but embodiments of the present disclosure are not limited thereto.

Hereinafter, FIG. 3 to FIG. 6 are cross-sectional views schematically showing electroluminescence devices according to embodiments. The electroluminescence device ED according to one or more embodiments may include a first electrode EL1, a hole transport region HTR, an emission layer EML, an electron transport region ETR, and a second electrode EL2 stacked in order.

Figure 3:
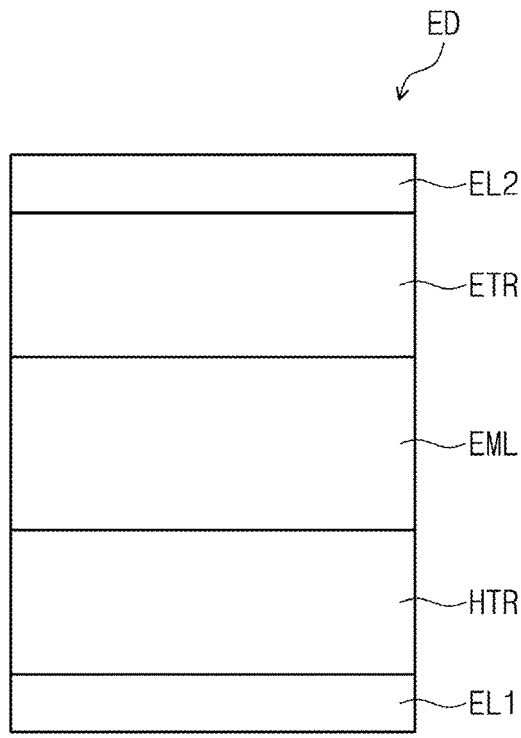
FIG. 3, FIG. 4, FIG. 5 and FIG. 6 are cross-sectional views schematically showing electroluminescence devices of embodiments.
Figure 4:
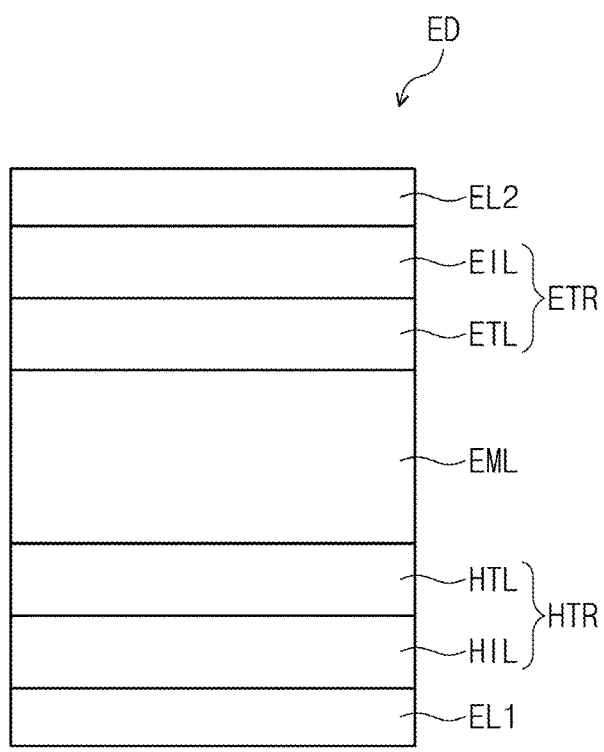
Figure 5:
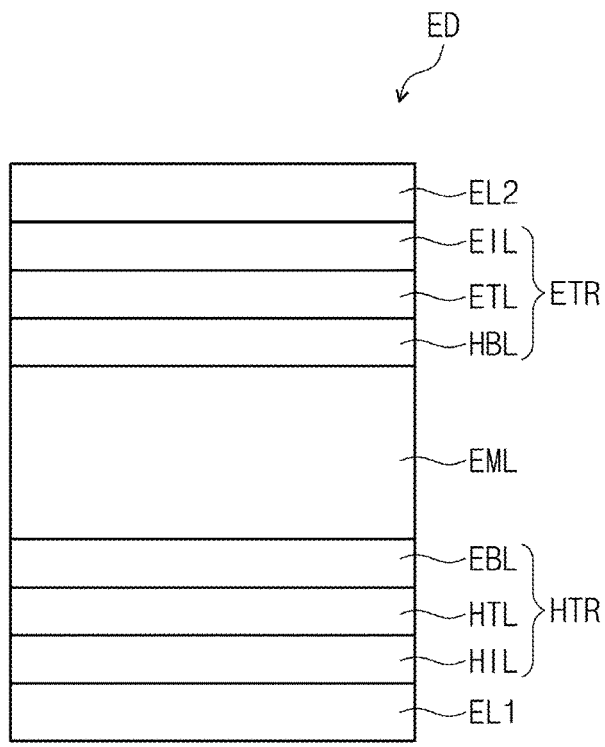
Figure 6:
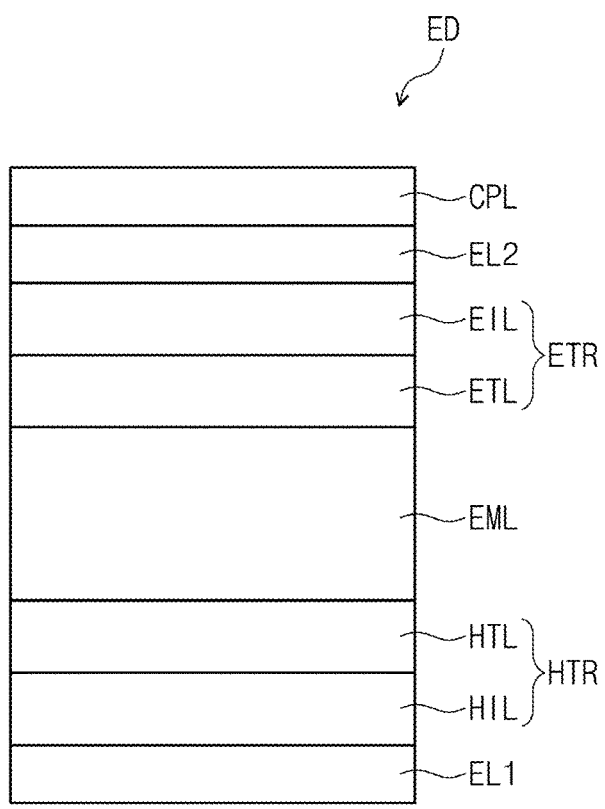

When compared with FIG. 3, FIG. 4 shows the cross-sectional view of an electroluminescence device ED of one or more embodiments, wherein a hole transport region HTR includes a hole injection layer HIL and a hole transport layer HTL, and an electron transport region ETR includes an electron injection layer EIL and an electron transport layer ETL. In addition, when compared with FIG. 3, FIG. 5 shows the cross-sectional view of an electroluminescence device ED of one or more embodiments, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. When compared with FIG. 4, FIG. 6 shows the cross-sectional view of an electroluminescence device ED of one or more embodiments, including a capping layer CPL disposed on the second electrode EL2.

The first electrode EL1 has conductivity. The first electrode EL1 may be formed using a metal material, a metal alloy or any suitable conductive compound. The first electrode EL1 may be an anode or a cathode. However, embodiments of the present disclosure are not limited thereto. For example, the first electrode EL1 may be a pixel electrode. The first electrode EL1 may be a transmissive electrode, a transflective electrode, or a reflective electrode. If the first electrode EL1 is the transmissive electrode, the first electrode EL1 may be formed using a transparent metal oxide such as indium tin oxide (ITO), indium zinc oxide (IZO), zinc oxide (ZnO), and/or indium tin zinc oxide (ITZO). If the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, W, a compound thereof, or a mixture thereof (for example, a mixture of Ag and Mg). In one or more embodiments, the first electrode EL1 may have a structure including multiple layers including a reflective layer or a transflective layer formed using any of the above materials, and a transmissive conductive layer formed using ITO, IZO, ZnO, and/or ITZO. For example, the first electrode EL1 may include a three-layer structure of ITO/Ag/ITO. However, embodiments of the present disclosure are not limited thereto. The first electrode EL1 may include the aforementioned metal materials, combinations of two or more metal materials selected from the aforementioned metal materials, and/or oxides of the aforementioned metal materials. The thickness of the first electrode EL1 may be from about 700 Å to about 10,000 Å. For example, the thickness of the first electrode EL1 may be from about 1,000 Å to about 3,000 Å.

The hole transport region HTR is provided on the first electrode EL1. The hole transport region HTR may include at least one of a hole injection layer HIL, a hole transport layer HTL, a buffer layer, an emission auxiliary layer or an electron blocking layer EBL. The thickness of the hole transport region HTR may be from about 50 Å to about 15,000 Å.

The hole transport region HTR may have a single layer formed using (e.g., consisting of) a single material, a single layer formed using multiple different materials, or a multi-layer structure including multiple layers formed using multiple different materials.

For example, the hole transport region HTR may have the structure of a single layer of a hole injection layer HIL or a hole transport layer HTL, or may have a structure of a single layer formed using a hole injection material and a hole transport material. In one or more embodiments, the hole transport region HTR may have a structure of a single layer formed using multiple (e.g., a plurality) of different materials, or a structure stacked from the first electrode EL1 of hole injection layer HIL/hole transport layer HTL, hole injection layer HIL/hole transport layer HTL/buffer layer, hole injection layer HIL/buffer layer, hole transport layer HTL/buffer layer, or hole injection layer HIL/hole transport layer HTL/electron blocking layer EBL, without limitation.

The hole transport region HTR may be formed using one or more suitable methods such as a vacuum deposition method, a spin coating method, a cast method, a Langmuir-Blodgett (LB) method, an inkjet printing method, a laser printing method, and/or a laser induced thermal imaging (LITI) method.

The hole transport region HTR may include a compound represented by Formula H-1 below:

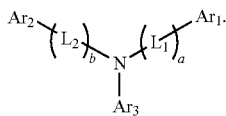

Formula H-1

In Formula H-1, $L_1$ and $L_2$ may be each independently a direct linkage, a substituted or unsubstituted arylene group of 6 to 30 ring-forming carbon atoms, or a substituted or unsubstituted heteroarylene group of 2 to 30 ring-forming carbon atoms. "a" and "b" may be each independently an integer of 0 to 10. Meanwhile, if "a" or "b" is an integer of 2 or more, multiple (a plurality of) $L_1$ and $L_2$ may be each independently a substituted or unsubstituted arylene group of 6 to 30 ring-forming carbon atoms, or a substituted or unsubstituted heteroarylene group of 2 to 30 ring-forming carbon atoms.

In Formula H-1, $Ar_1$ and $Ar_2$ may be each independently a substituted or unsubstituted aryl group of 6 to 30 ring-forming carbon atoms, or a substituted or unsubstituted heteroaryl group of 2 to 30 ring-forming carbon atoms. In one or more embodiments, in Formula H-1, $Ar_3$ may be a substituted or unsubstituted aryl group of 6 to 30 ring-forming carbon atoms.

The compound represented by Formula H-1 may be a monoamine compound. In one or more embodiments, the compound represented by Formula H-1 may be a diamine compound in which at least one selected from among $Ar_1$ to $Ar_3$ includes an amine group as a substituent. Further, the compound represented by Formula H-1 may be a carbazole-based compound in which a substituted or unsubstituted carbazole group is included in at least one selected from among $Ar_1$ and $Ar_2$, or a fluorene-based compound in which a substituted or unsubstituted fluorene group is included in at least one selected from among $Ar_1$ and $Ar_2$.

The compound represented by Formula H-1 may be represented by any one selected from among the compounds represented in Compound Group H below. However, the compounds illustrated in Compound Group H are embodiments, and the compound represented by Formula H-1 is not limited to those represented in Compound Group H below:

Compound Group H

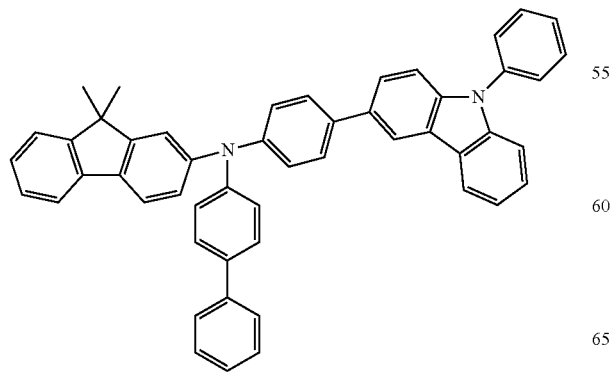

-continued

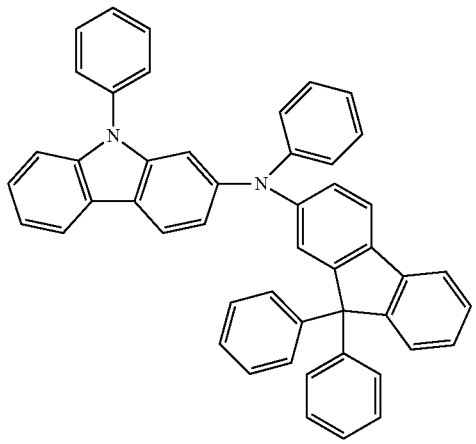

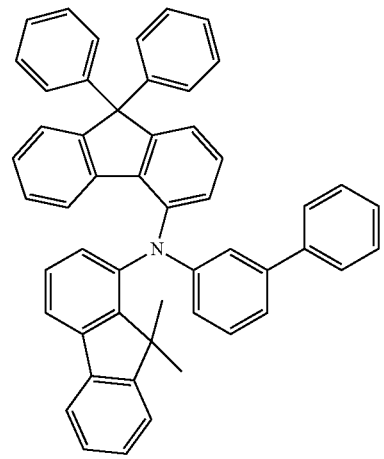

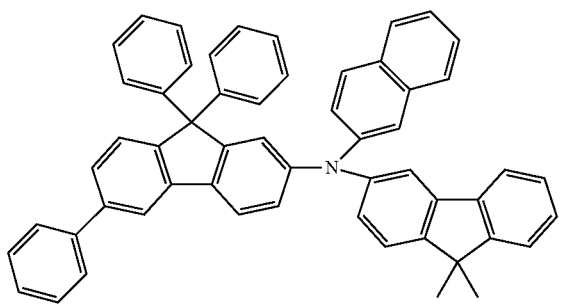

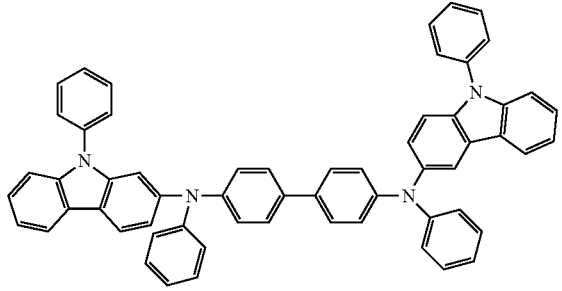

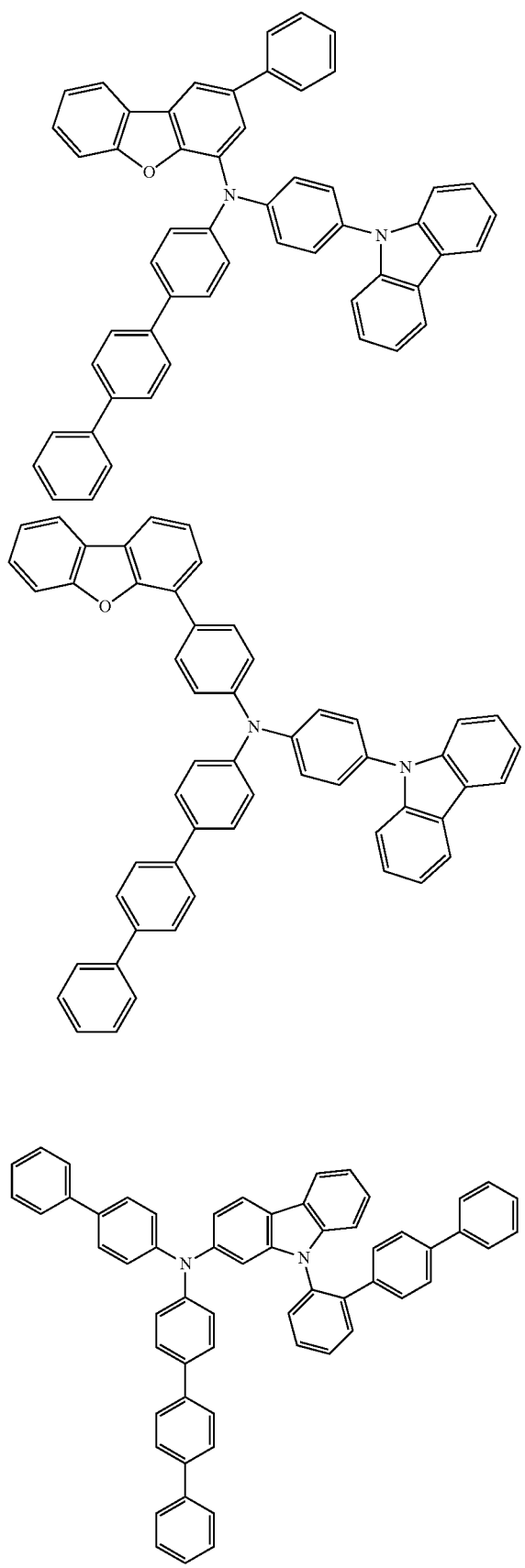
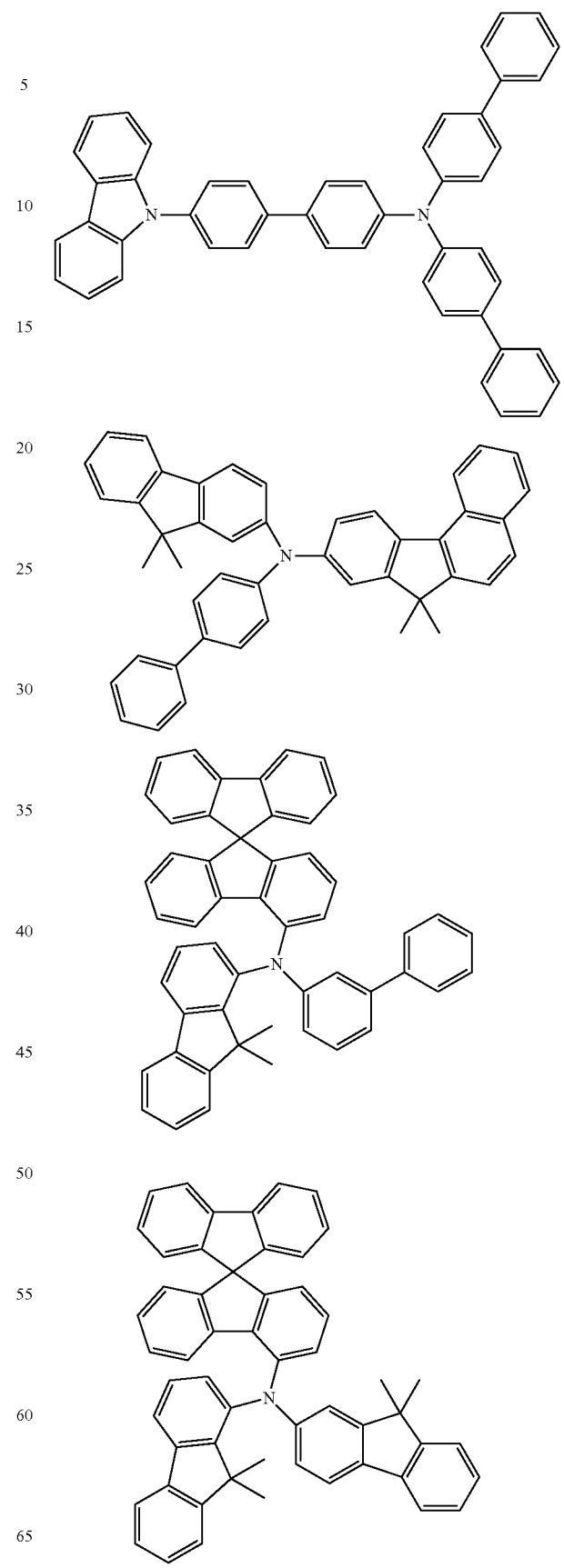

-continued

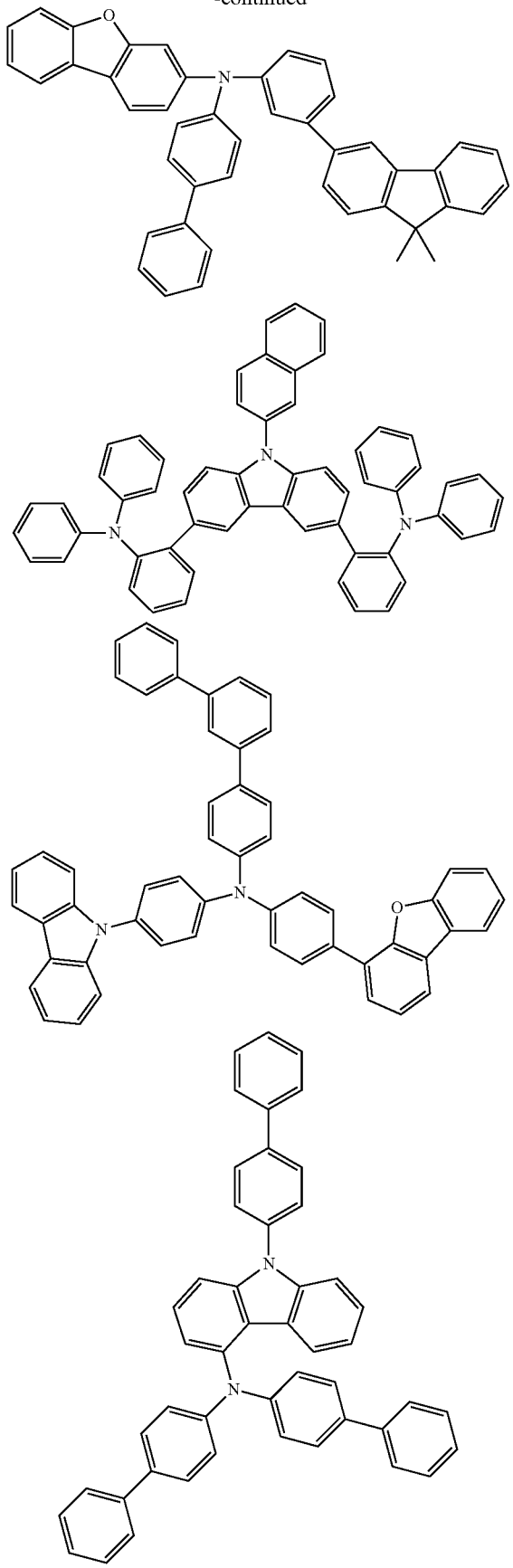

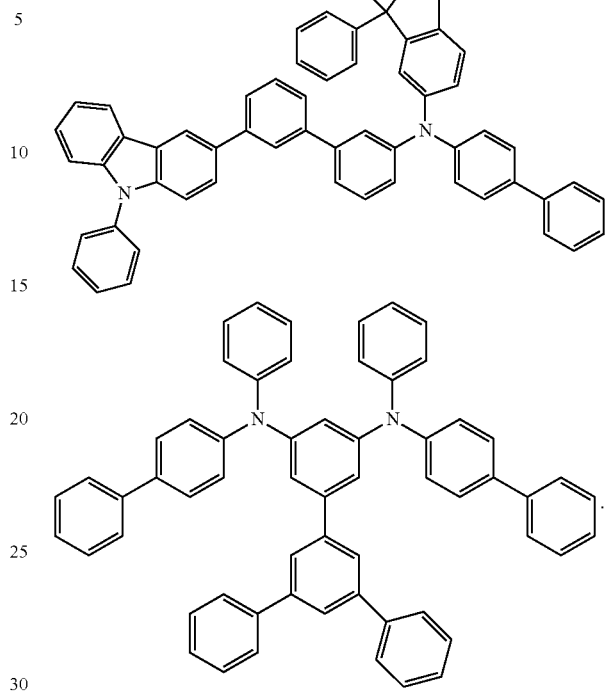

The hole transport region HTR may include a phthalocyanine compound (such as copper phthalocyanine), $N^1,N^{1'}$-([1,1'-biphenyl]-4,4'-diyl)bis($N^1$-(phenyl-$N^4$,$N^4$-di-m-tolylbenzene-1,4-diamine (DNTPD), 4,4',4''-[tris(3-methylphenyl)phenylamino]triphenylamine (m-MTDATA), 4,4',4''-tris(N,N-diphenylamino)triphenylamine (TDATA), 4,4',4''-tris[N(2-naphthyl)-N-phenylamino]-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(1-naphthalene-1-yl)-N,N'-diphenylbenzidine (NPB), triphenylamine-containing polyetherketone (TPAPEK), 4-isopropyl-4'-methyldiphenyliodonium [tetrakis(pentafluorophenyl)borate], and/or dipyrazino[2,3-f:2',3'-h] quinoxaline-2,3,6,7,10,11-hexacarbonitrile (HAT-CN).

The hole transport region HTR may include carbazole derivatives (such as N-phenyl carbazole and/or polyvinyl carbazole), fluorene-based derivatives, N,N'-bis(3-methylphenyl)-N,N'-diphenyl-[1,1'-biphenyl]-4,4'-diamine (TPD), triphenylamine-based derivatives (such as 4,4',4''-tris(N-carbazolyl)triphenylamine (TCTA)), N,N'-di(1-naphthalene-1-yl)-N,N'-diphenyl-benzidine (NPB), 4,4'-cyclohexylidene bis[N,N-bis(4-methylphenyl)benzeneamine (TAPC), 4,4'-bis[N,N'-(3-tolyl)amino]-3,3'-dimethylbiphenyl (HMTPD), 1,3-bis(N-carbazolyl)benzene (mCP), etc.

In one or more embodiments, the hole transport region HTR may include carbazole derivatives (such as N-phenyl carbazole and/or polyvinyl carbazole), fluorene-based derivatives, N,N'-bis(3-methylphenyl)-N, N'-diphenyl-[1,1-biphenyl]-4,4'-diamine (TPD), triphenylamine-based derivatives (such as 4,4',4''-tris(N-carbazolyl)triphenylamine (TCTA)), N,N'-di(1-naphthalene-1-yl)-N,N'-diphenyl-benzidine (NPB), 4,4'-cyclohexylidene bis[N,N-bis(4-methylphenyl)benzeneamine (TAPC), 4,4'-bis[N,N'-(3-tolyl) amino]-3,3'-dimethylbiphenyl (HMTPD), 9-(4-tert-butylphenyl)-3,6-bis(triphenylsilyl)-9H-carbazole (CzSi), 9-phenyl-9H-3,9'-bicarbazole (CCP), 1,3-bis(N-carbazolyl) benzene (mCP), 1,3-bis(1,8-dimethyl-9H-carbazol-9-yl) benzene (mDCP), etc.

The hole transport region HTR may include the above-described compounds of the hole transport region in at least one of a hole injection layer HIL, a hole transport layer HTL, or an electron blocking layer EBL.

The thickness of the hole transport region HTR may be from about 100 Å to about 10,000 Å, for example, from about 100 Å to about 5,000 Å. In case where the hole transport region HTR includes the hole injection layer HIL, the thickness of the hole injection region HIL may be, for example, from about 30 Å to about 1,000 Å. In case where the hole transport region HTR includes the hole transport layer HTL, the thickness of the hole transport layer HTL may be from about 30 Å to about 1,000 Å. For example, in case where the hole transport region HTR includes the electron blocking layer EBL, the thickness of the electron blocking layer EBL may be from about 10 Å to about 1,000 Å. If the thicknesses of the hole transport region HTR, the hole injection layer HIL, the hole transport layer HTL and the electron blocking layer EBL satisfy the above-described respective ranges, satisfactory (or suitable) hole transport properties may be obtained without substantial increase of a driving voltage.

The hole transport region HTR may further include a charge generating material, in addition to the above-described materials, to increase conductivity. The charge generating material may be dispersed uniformly or non-uniformly in the hole transport region HTR. The charge generating material may be, for example, a p-dopant. The p-dopant may include any one selected from among halogenated metal compounds, quinone derivatives, metal oxides, and cyano group-containing compounds, without limitation. For example, the p-dopant may include halogenated metal compounds (such as CuI and/or RbI), quinone derivatives (such as tetracyanoquinodimethane (TCNQ) and/or 2,3,5,6-tetrafluoro-7,7',8,8-tetracyanoquinodimethane (F4-TCNQ)), metal oxides (such as tungsten oxide and/or molybdenum oxide), cyano group-containing compounds (such as dipyrazino[2,3-f: 2',3'-h] quinoxaline-2,3, 6,7,10,11-hexacarbonitrile (HATCN) and/or 4-[[2,3-bis [cyano-(4-cyano-2,3,5,6-tetrafluorophenyl)methylidene] cyclopropylidene]-cyanomethyl]-2,3,5,6-tetrafluorobenzonitrile), etc., without limitation.

As described above, the hole transport region HTR may further include at least one of a buffer layer or an electron blocking layer EBL, in addition to the hole injection layer HIL and the hole transport layer HTL. The buffer layer may compensate an optical resonance distance according to the wavelength of light emitted from an emission layer EML and may increase light emission efficiency. Materials which may be included in a hole transport region HTR may be used as materials included in a buffer layer. The electron blocking layer EBL is a layer playing the role of preventing or reducing the electron injection from the electron transport region ETR to the hole transport region HTR.

The emission layer EML is provided on the hole transport region HTR. The emission layer EML may, for example, have a thickness of about 100 Å to about 1,000 Å or about 100 Å to about 300 Å. The emission layer EML may have a single layer formed using (e.g., consisting of) a single material, a single layer formed using multiple different materials, or a multilayer structure having multiple layers formed using multiple different materials.

The emission layer EML of the electroluminescence device ED of one or more embodiments may include the polycyclic compound of one or more embodiments.

The polycyclic compound of one or more embodiments includes a substituted or unsubstituted fluorene group, a substituted or unsubstituted phenyl group connected with a carbon atom at position 9 of the substituted or unsubstituted fluorene group, a substituted or unsubstituted first carbazole group connected with the carbon atom at position 9 of the substituted or unsubstituted fluorene group, and a substituted or unsubstituted second carbazole group connected with a nitrogen atom of the substituted or unsubstituted first carbazole group. The following images illustrate positions in a fluorene moiety and in a carbazole moiety:

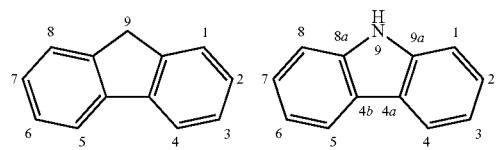

The substituted or unsubstituted fluorene group may be one in which the substituted or unsubstituted phenyl group and the substituted or unsubstituted first carbazole group are substituted at the carbon atom at position 9, and hydrogen atoms are substituted at carbon atoms at positions 1 to 8. In one or more embodiments, deuterium atoms may be substituted at the carbon atoms at positions 1 to 8. For example, two benzene rings included in the substituted or unsubstituted fluorene group may be unsubstituted benzene rings or benzene rings substituted with deuterium atoms.

The substituted or unsubstituted phenyl group may be directly connected with the carbon atom at position 9 of the substituted or unsubstituted fluorene group. The substituted or unsubstituted first carbazole group may be directly connected with the carbon atom at position 9 of the substituted or unsubstituted fluorene group. That is, the substituted or unsubstituted phenyl group and the substituted or unsubstituted first carbazole group may be directly connected with the carbon atom at position 9 of the substituted or unsubstituted fluorene group without separate linkers.

The substituted or unsubstituted phenyl group and the substituted or unsubstituted first carbazole group may be connected with each other but may not form a ring. For example, a substituent connected with the substituted or unsubstituted phenyl group and a substituent substituted at the substituted or unsubstituted first carbazole group may not be connected with each other, or may be connected but may not form a ring.

In one or more embodiments, the carbon atom at position 9 in the fluorene group may be a carbon atom which is not shared with a benzene ring, among five carbon atoms forming a pentagonal ring combined between two benzene rings. The carbon atoms at positions 1 to 8 may be eight carbon atoms which are not shared with the pentagonal ring among the carbon atoms of two benzene rings included in the fluorene group.

At the nitrogen atom at position 9 of the substituted or unsubstituted first carbazole group, a substituted or unsubstituted second carbazole group may be substituted. The substituted or unsubstituted second carbazole group may be directly connected with the nitrogen atom of the substituted or unsubstituted first carbazole group.

With the nitrogen atom of the second carbazole group, a hydrogen atom, a deuterium atom, a halogen atom, a cyano group, a substituted or unsubstituted silyl group, a substituted or unsubstituted alkyl group of 1 to 30 carbon atoms, a substituted or unsubstituted alkenyl group of 2 to 30 carbon atoms, a substituted or unsubstituted amine group, a substituted or unsubstituted aryl group of 6 to 30 ring-forming carbon atoms, or a substituted or unsubstituted heteroaryl group of 2 to 30 ring-forming carbon atoms may be connected. For example, with the nitrogen atom of the second carbazole group, a substituted or unsubstituted aryl group of 6 to 30 ring-forming carbon atoms, or a substituted or unsubstituted heteroaryl group of 2 to 30 ring-forming carbon atoms may be connected. In some embodiments, with the nitrogen atom of the second carbazole group, a substituted or unsubstituted phenyl group may be connected, or a substituted or unsubstituted dibenzoheterole group may be connected. For example, with the nitrogen atom of the second carbazole group, derivatives of a dibenzoheterole group such as a substituted or unsubstituted third carbazole group, a substituted or unsubstituted dibenzofuran group, a substituted or unsubstituted dibenzothiophene group, and/or a substituted or unsubstituted dibenzofuran group may be connected.

The polycyclic compound of one or more embodiments may be represented by Formula 1 below:

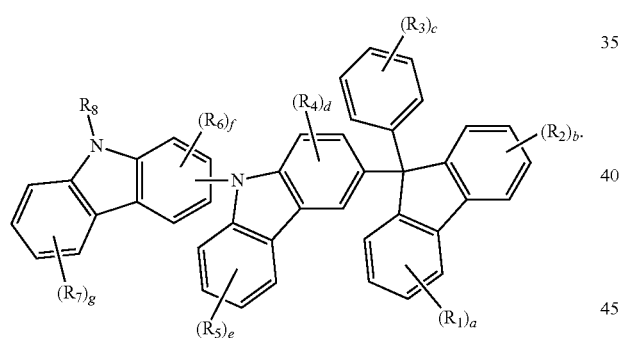

Formula 1

In Formula 1, $R_1$ to $R_8$ may be each independently a hydrogen atom, a deuterium atom, a halogen atom, a cyano group, a substituted or unsubstituted silyl group, a substituted or unsubstituted alkyl group of 1 to 30 carbon atoms, a substituted or unsubstituted alkenyl group of 2 to 30 carbon atoms, a substituted or unsubstituted amine group, a substituted or unsubstituted aryl group of 6 to 30 ring-forming carbon atoms, or a substituted or unsubstituted heteroaryl group of 2 to 30 ring-forming carbon atoms.

For example, $R_1$ to $R_4$, $R_6$, and $R_7$ may be each independently a hydrogen atom or a deuterium atom.

For example, $R_5$ may be a hydrogen atom, a deuterium atom, a substituted or unsubstituted carbazole group, a substituted or unsubstituted dibenzofuran group, or a substituted or unsubstituted dibenzothiophene group.

For example, $R_5$ may be any one selected from among substituents represented by $t_1$ to $t_6$. However, examples of $R_5$ are not limited thereto:

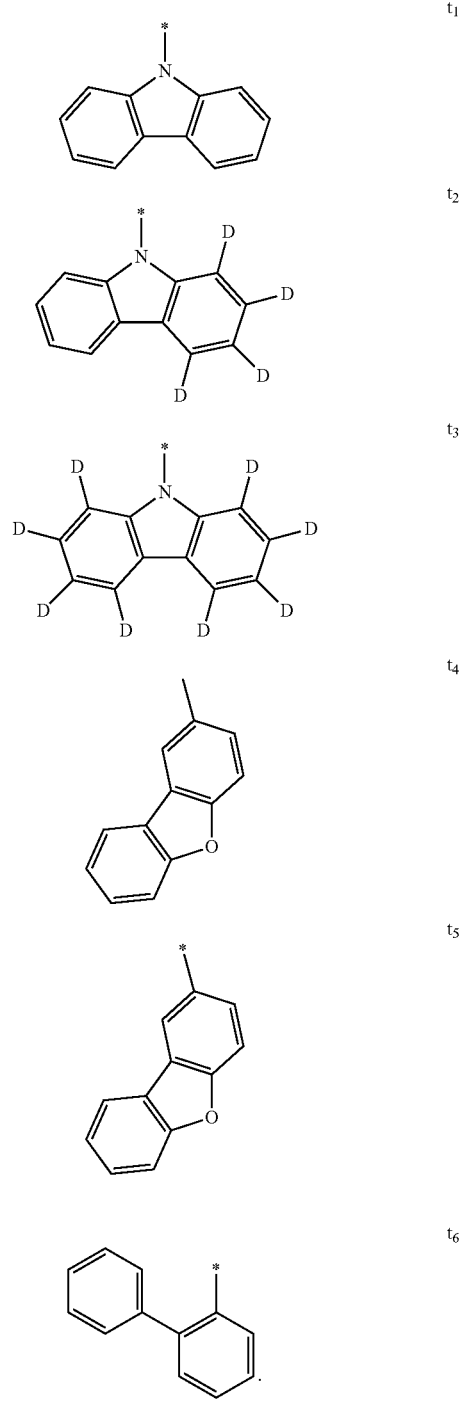

In one or more embodiments, $R_8$ may be a substituted or unsubstituted aryl group of 6 to 30 ring-forming carbon atoms, or a substituted or unsubstituted heteroaryl group of 2 to 30 ring-forming carbon atoms. For example, $R_8$ may be a substituted or unsubstituted phenyl group, a substituted or unsubstituted fluorene group, or a substituted or unsubstituted dibenzoheterole group.

For example, $R_8$ may be any one selected from among substituents represented by $S_1$ to $S_{17}$. However, examples of $R_8$ are not limited thereto:

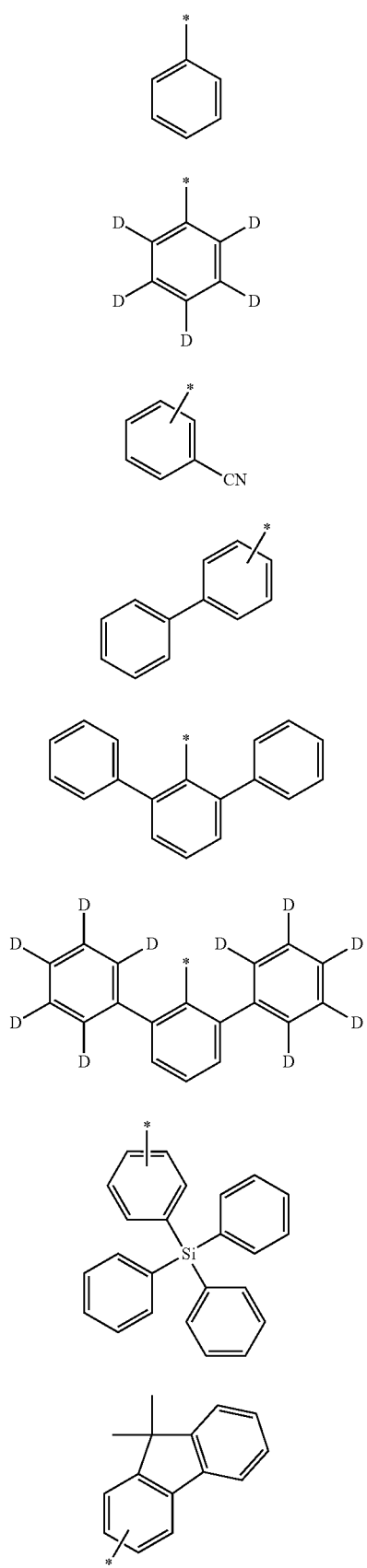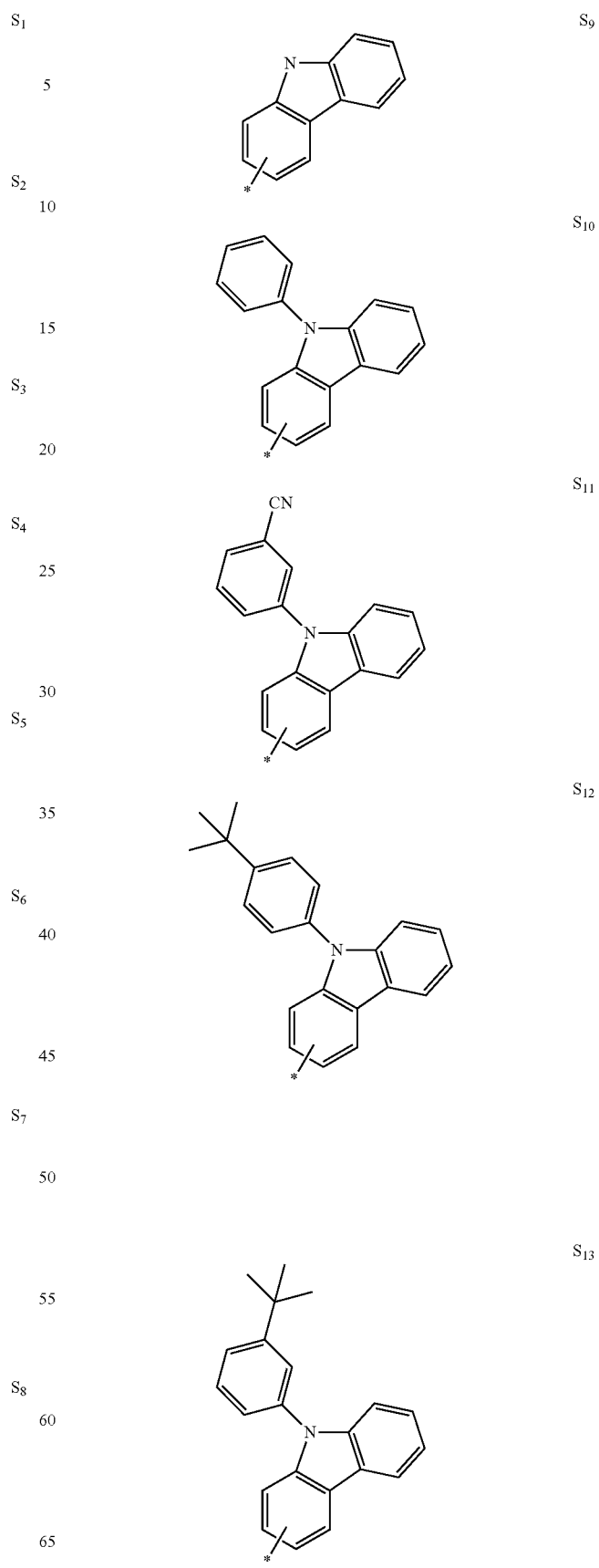

In Formula 1, "a" and "b" may be each independently an integer of 0 to 4, "c" may be an integer of 0 to 5, "d" may be an integer of 0 to 3, "e" may be an integer of 0 to 4, "f" may be an integer of 0 to 3, and "g" is an integer of 0 to 4.

For example, "a", "b" and "c" may be 0. A case where "a" is 0 may be the same as a case where $R_1$ is a hydrogen atom. Cases where "b" and "c" are 0 may be the same as cases where $R_2$ and $R_3$ are hydrogen atoms, respectively.

For example, "d" may be 0 or 3. A case where "d" is 0 may be the same as a case where $R_4$ is a hydrogen atom. A case where "d" is 3 may be a case where three $R_4$ groups are deuterium atoms.

For example, "e" may be 0, 1 or 4. A case where "e" is 0 may be the same as a case where $R_5$ is a hydrogen atom. A case where "e" is 1 may be a case where $R_5$ is a substituted or unsubstituted carbazole group, a substituted or unsubstituted dibenzofuran group, or a substituted or unsubstituted dibenzothiophene group. For example, a case where "e" is 1 may be a case where $R_5$ is any one selected from among the substituents represented by $t_1$ to $t_6$. A case where "e" is 4 may be a case where $R_5$ is a deuterium atom (e.g., where four $R_5$ groups are deuterium atoms).

For example, "f" may be 0 or 3. A case where "f" is 0 may be the same as a case where $R_6$ is a hydrogen atom. A case where "f" is 3 may be a case where three $R_6$ groups are deuterium atoms.

For example, "g" may be 0 or 4. A case where "g" is 0 may be the same as a case where $R_7$ is a hydrogen atom. A case where "g" is 4 may be a case where four $R_7$ groups are deuterium atoms.

In one or more embodiments, Formula 1 may be represented by Formula 1-1 below:

Formula 1-1

In Formula 1-1, X may be $NAr_1$, O or S.

$Y_1$ to $Y_8$ may be each independently $CR_a$ or N. For example, in case where X is O, one among $Y_1$ to $Y_8$ may be N. For example, in case where X is $NAr_1$ or S, all $Y_1$ to $Y_8$ may be all $CR_a$.

$Ar_1$ may be a substituted or unsubstituted aryl group of 6 to 30 ring-forming carbon atoms, or a substituted or unsubstituted heteroaryl group of 2 to 30 ring-forming carbon atoms. For example, $Ar_1$ may be a substituted or unsubstituted phenyl group.

$R_a$ may be a hydrogen atom, a deuterium atom, a halogen atom, a cyano group, a substituted or unsubstituted silyl group, a substituted or unsubstituted alkyl group of 1 to 30 carbon atoms, a substituted or unsubstituted alkenyl group of 2 to 30 carbon atoms, a substituted or unsubstituted amine group, a substituted or unsubstituted aryl group of 6 to 30 ring-forming carbon atoms, or a substituted or unsubstituted heteroaryl group of 2 to 30 ring-forming carbon atoms. For example, $R_a$ may be a hydrogen atom.

$R_1$ to $R_7$, and "a" to "g" are the same as defined in Formula 1 above.

In one or more embodiments, Formula 1 may be represented by any one selected from among Formula 2-1 to Formula 2-3 below:

Formula 2-1

Formula 2-2

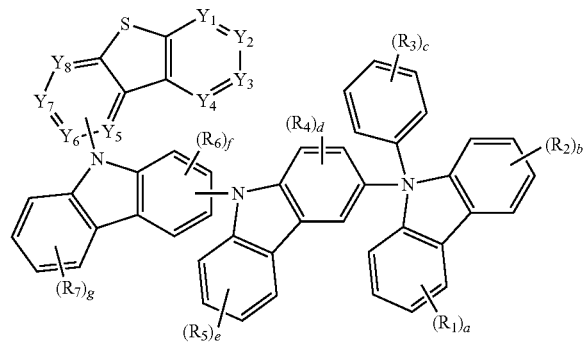

Formula 3-2

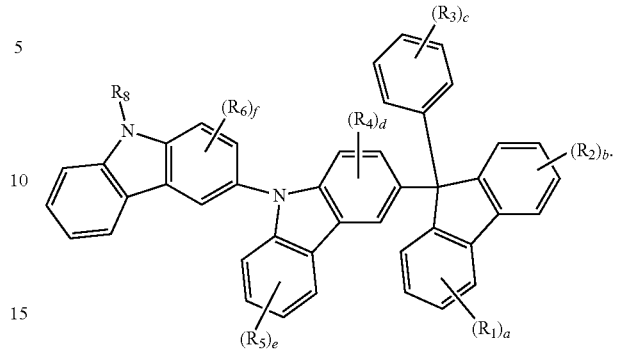

Formula 2-3

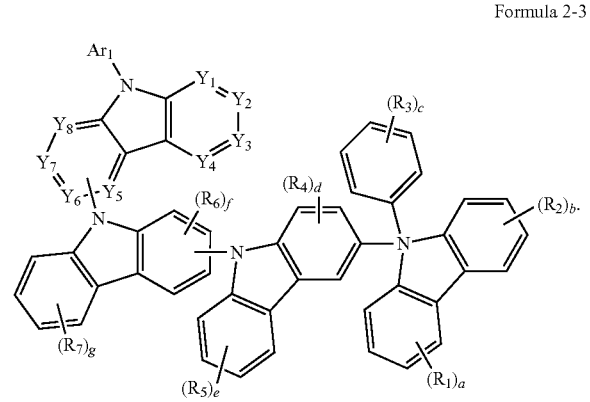

Formula 2-1 to Formula 2-3 are embodiments of Formula 1-1 where X is O, S, and $NAr_1$, respectively.

$Y_1$ to $Y_8$, $Ar_1$, $R_a$, $R_1$ to $R_7$, and "a" to "g" are the same as defined in Formula 1 and Formula 1-1.

In one or more embodiments, Formula 1 may be represented by Formula 3-1 or Formula 3-2 below:

Formula 3-1

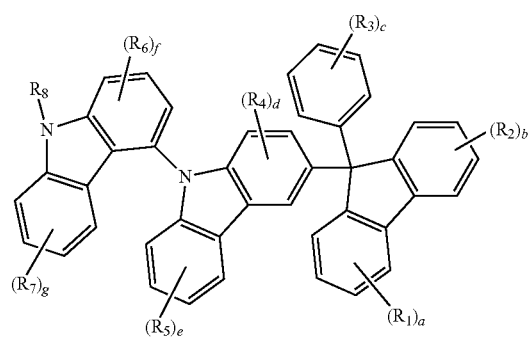

Formula 3-1 and Formula 3-2 correspond to Formula 1 in which the positions where two carbazole groups are connected, are embodied (e.g., defined). Formula 3-1 is a case where a carbazole group connected with a fluorene group (e.g., the first carbazole group) is substituted at the carbon atom at position 4 of the carbazole group where $R_8$ is directly connected (e.g., the second carbazole group). Formula 3-2 is a case where a carbazole group connected with a fluorene group (e.g., the first carbazole group) is substituted at the carbon atom at position 3 of the carbazole group where $R_8$ is directly connected (e.g., the second carbazole group).

$R_1$ to $R_8$, and "a" to "g" are the same as defined in Formula 1 above.

In one or more embodiments, Formula 1 may be represented by Formula 4-1 below:

Formula 4-1

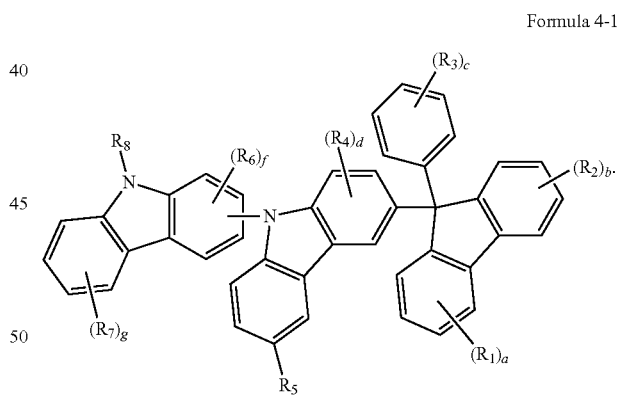

Formula 4-1 corresponds to Formula 1 where "e" is 1, and a substitution position where $R_5$ is connected to the benzene ring of a carbazole group is embodied (e.g., defined). $R_5$ may be connected with the carbon atom at position 6 of the carbazole group.

$R_1$ to $R_8$, "a" to "d", and "f" to "g" are the same as defined in Formula 1 above.

In one or more embodiments, the polycyclic compound represented by Formula 1 may include at least one selected from among the compounds represented in Compound Group 1 below:

Compound Group 1
1
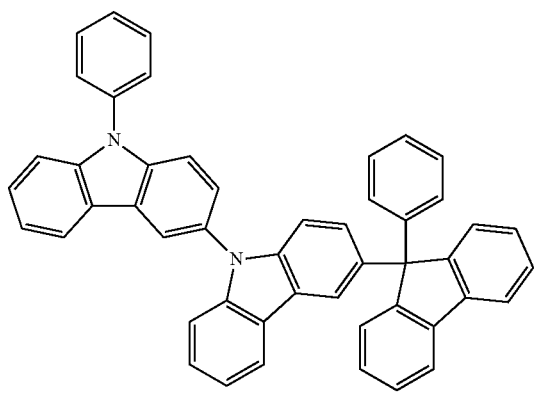
2
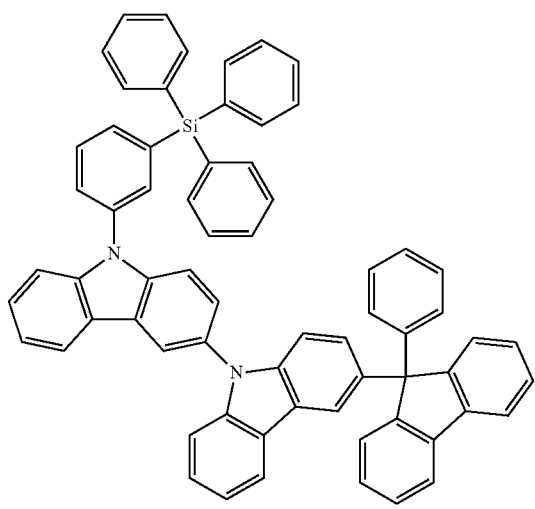
3
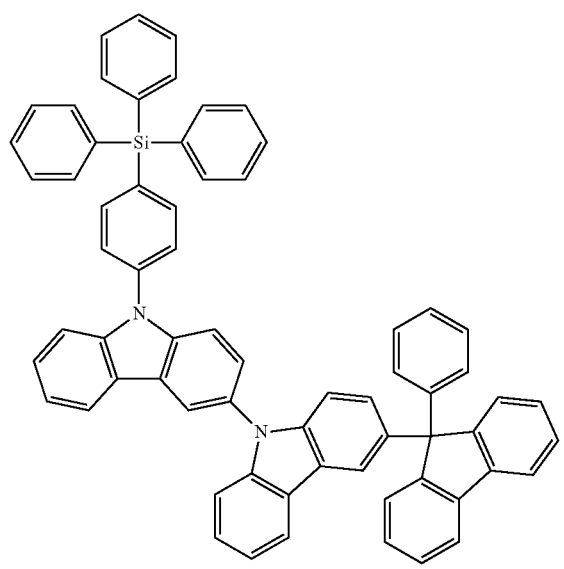
4
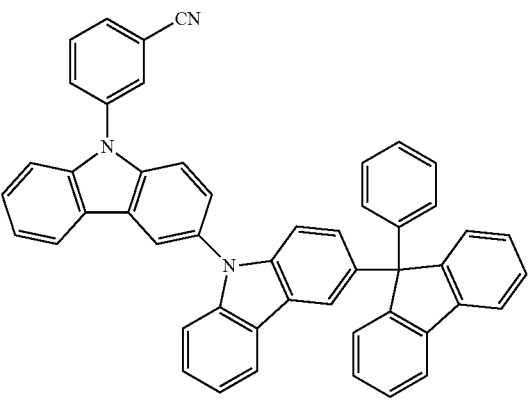
5
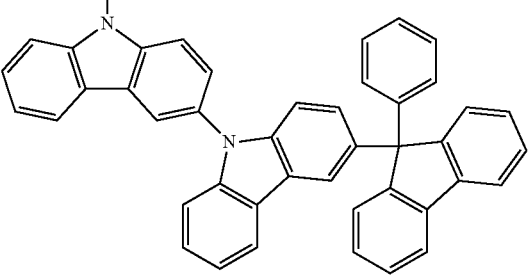
6
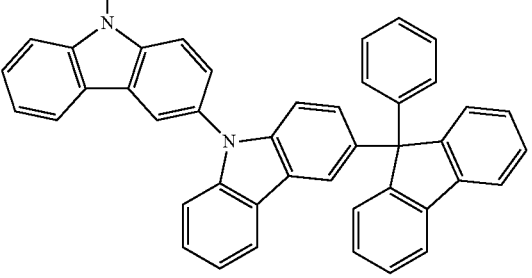

-continued
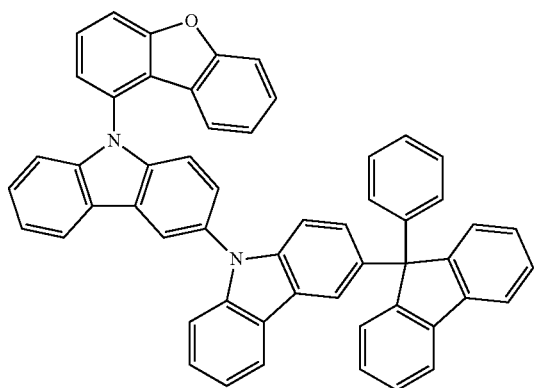
7
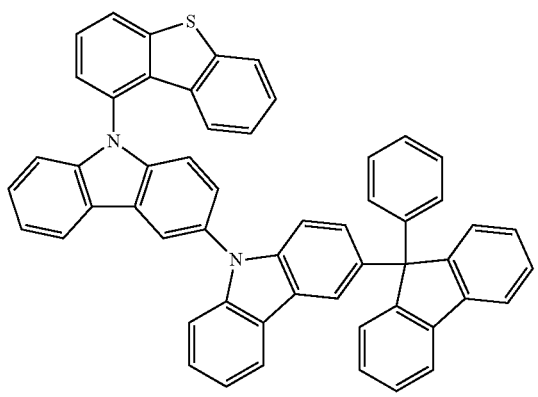
10
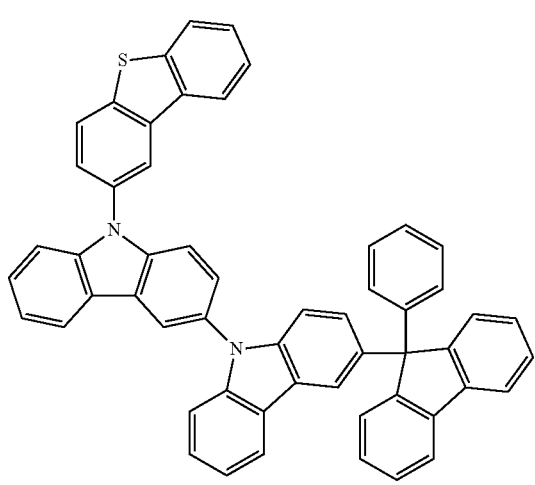
8
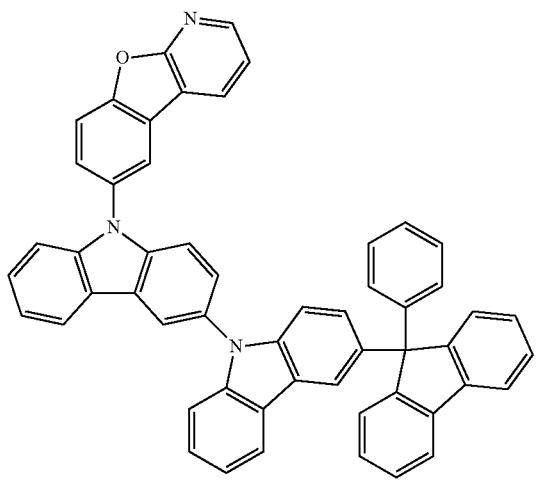
11
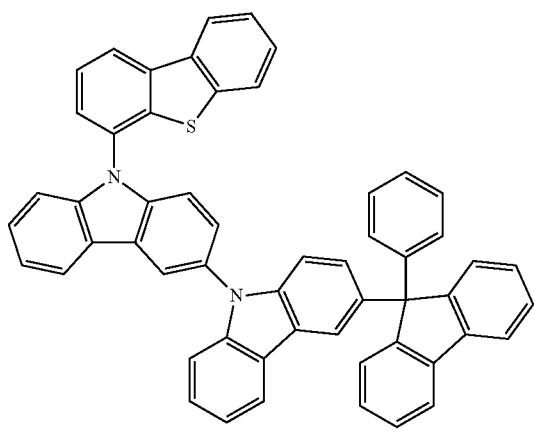
9
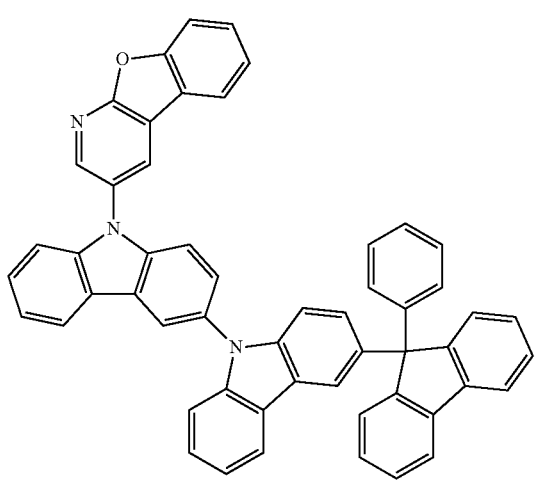
12

13
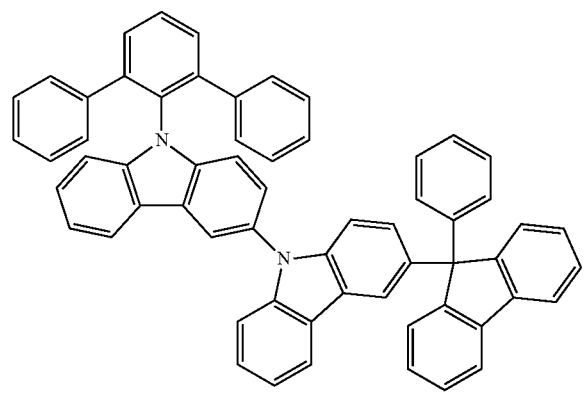
14
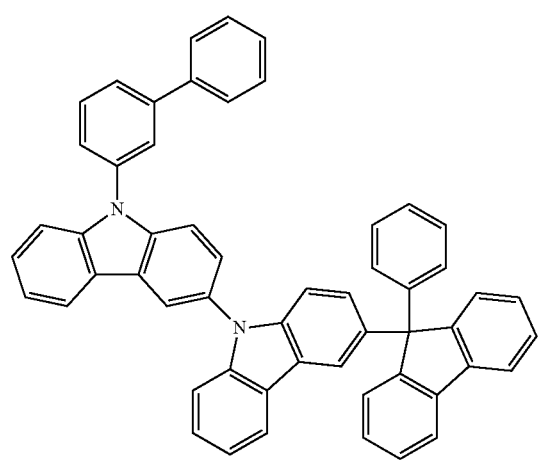
15
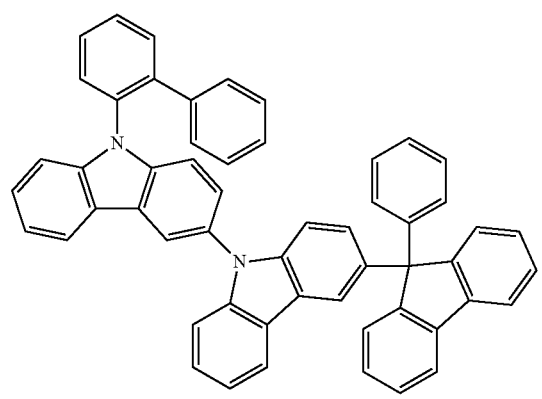
16
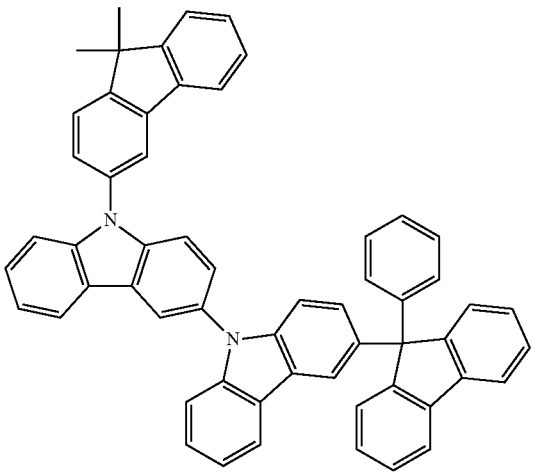
17
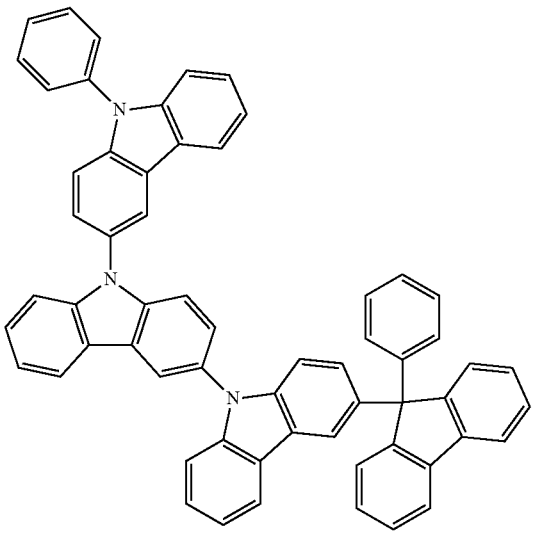
18
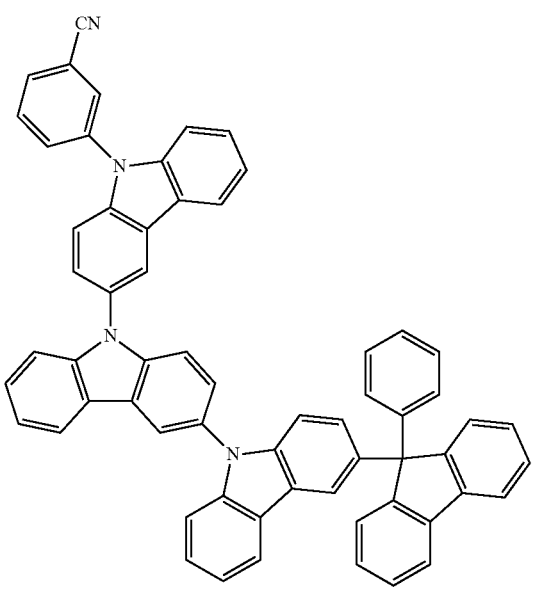

19
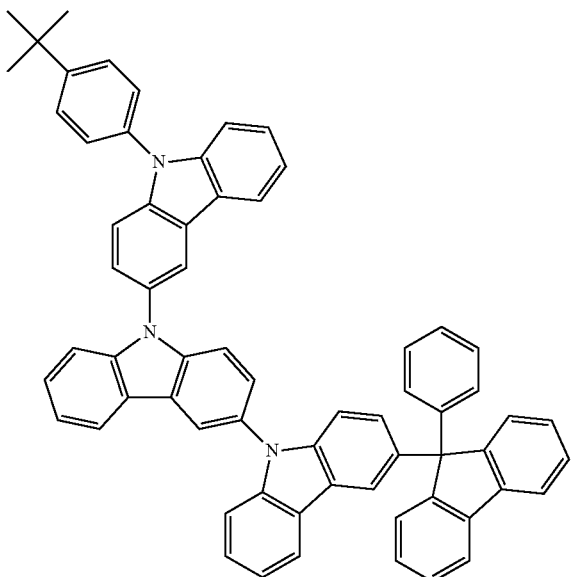
21
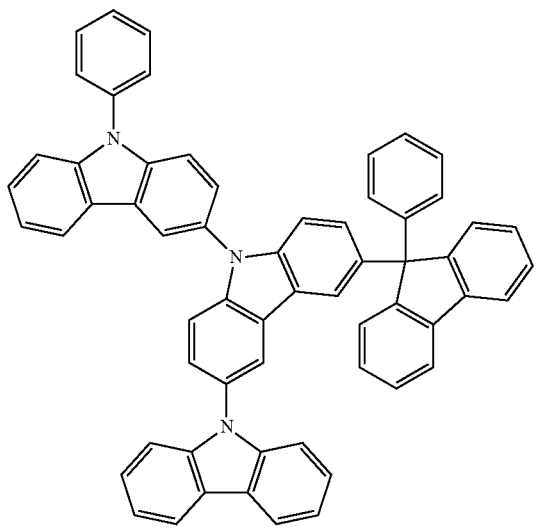
20
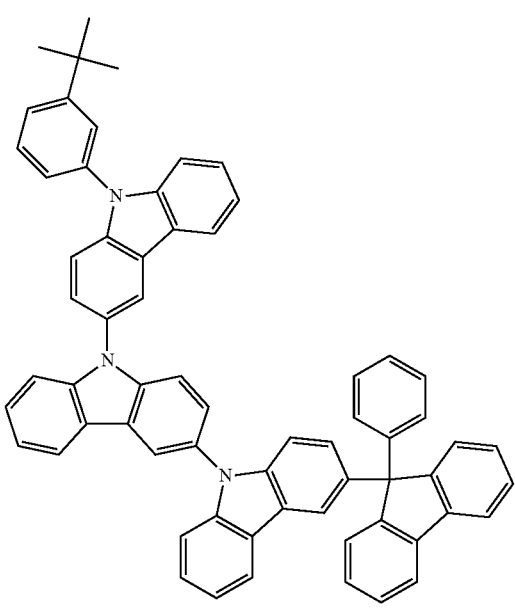
22
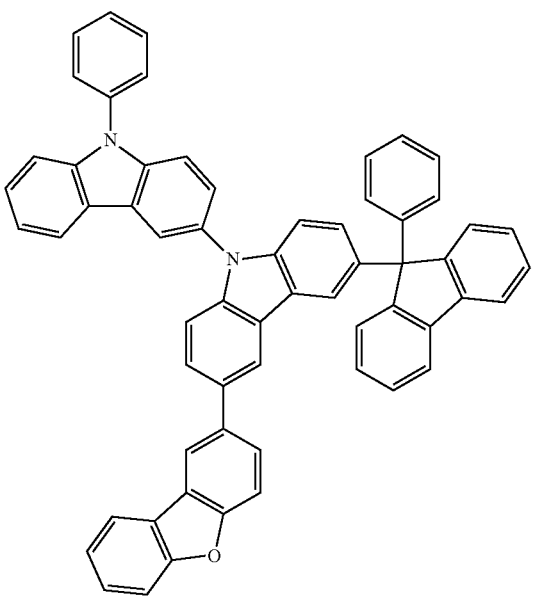

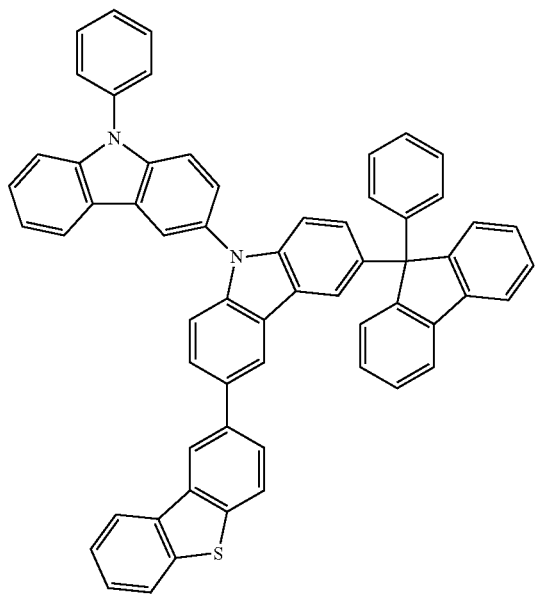
23
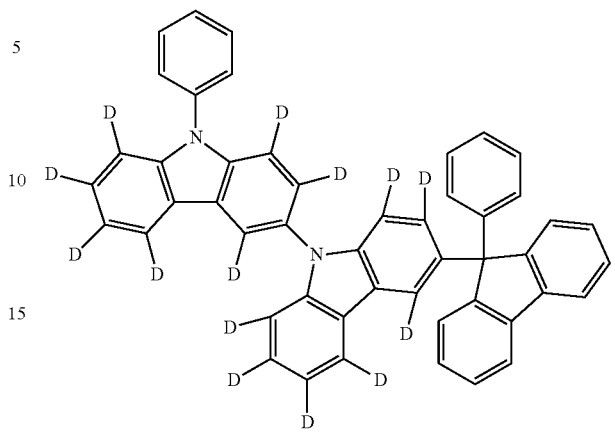
26
24
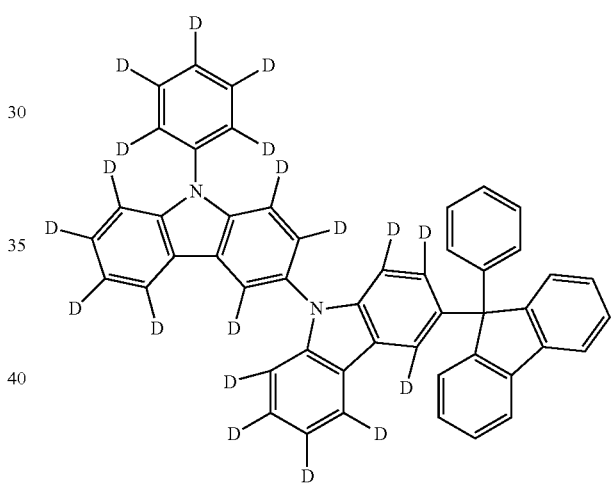
27
25
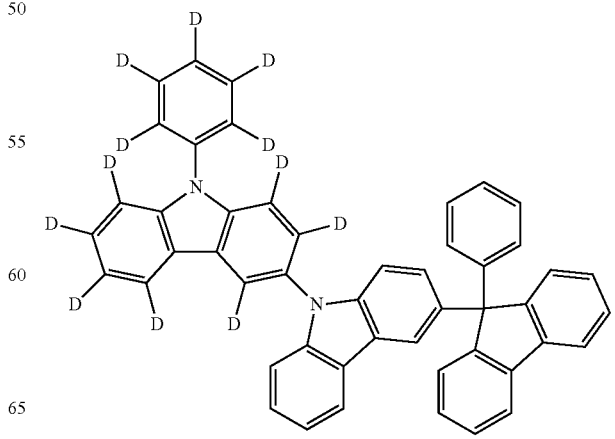
28

29
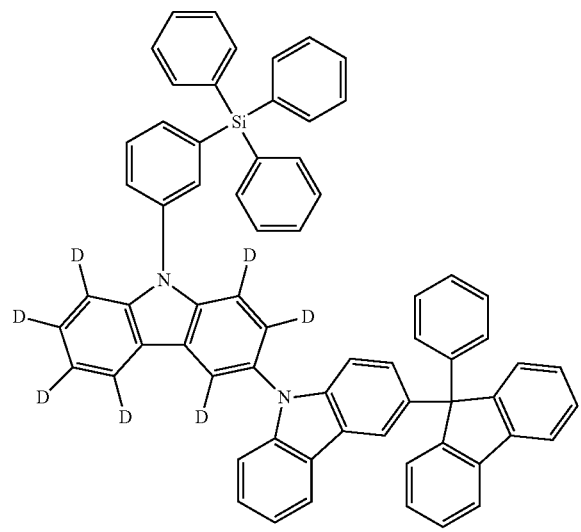
30
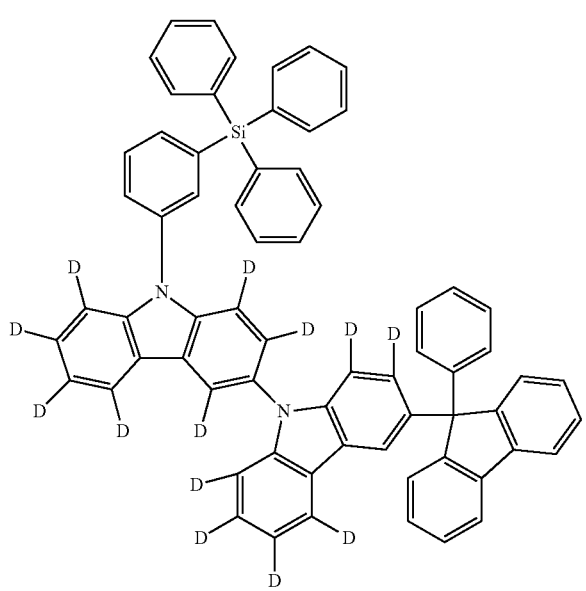
31
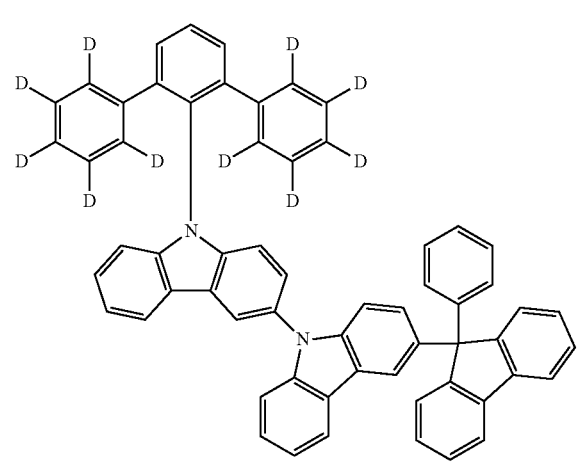
32
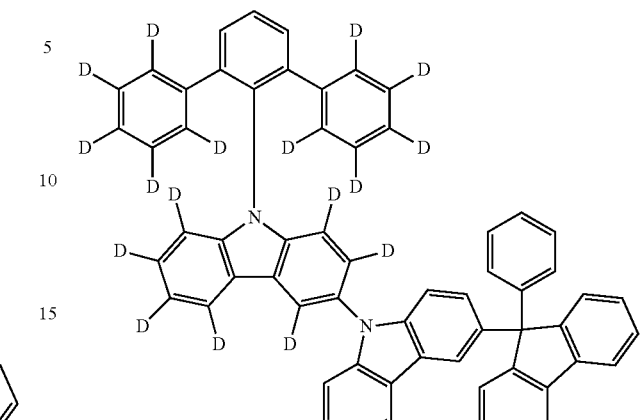
33
34

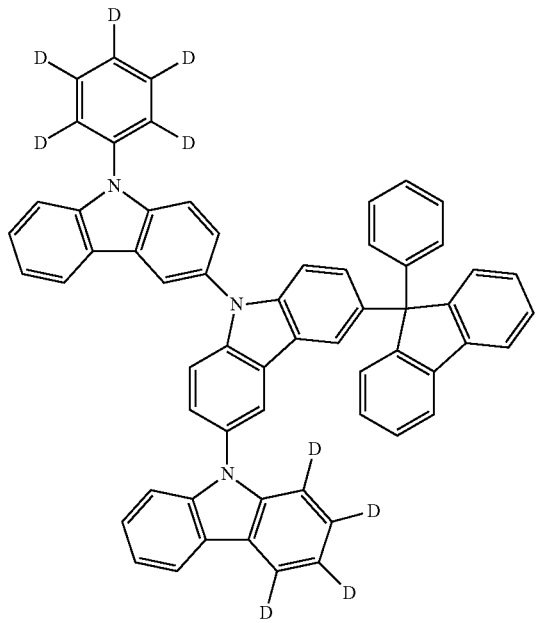
35
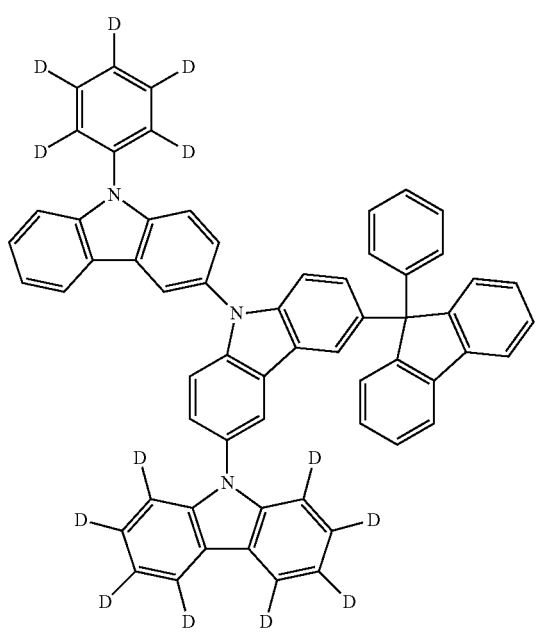
36
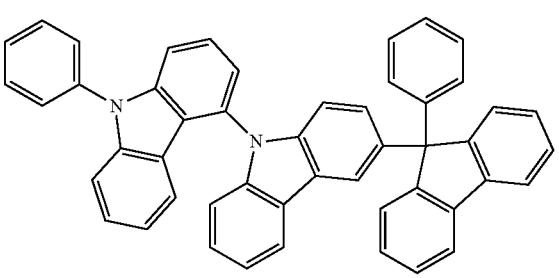
37
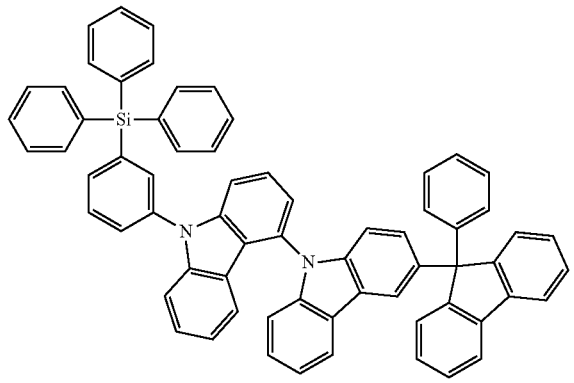
38
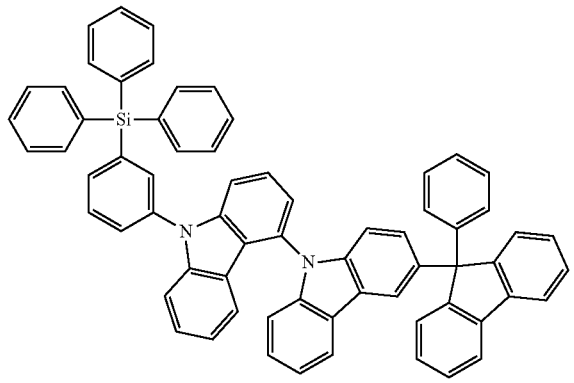
39
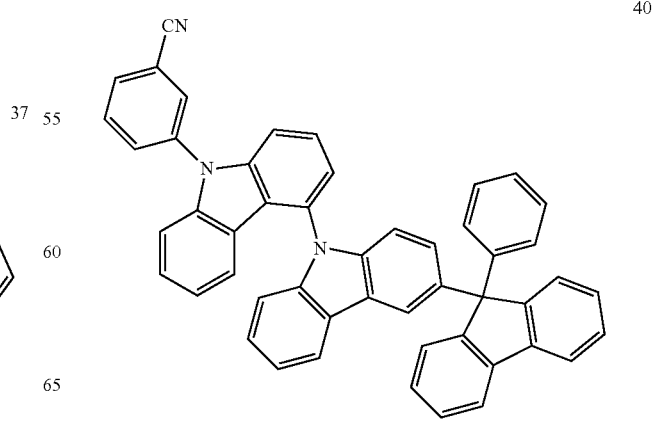
40

41
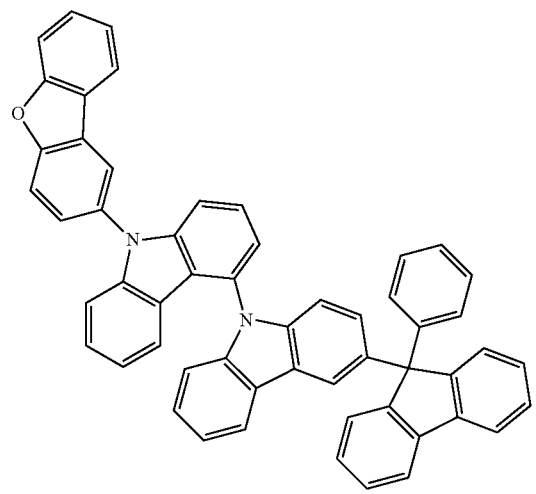
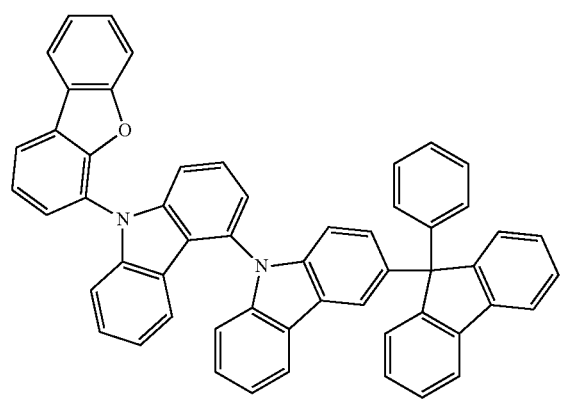
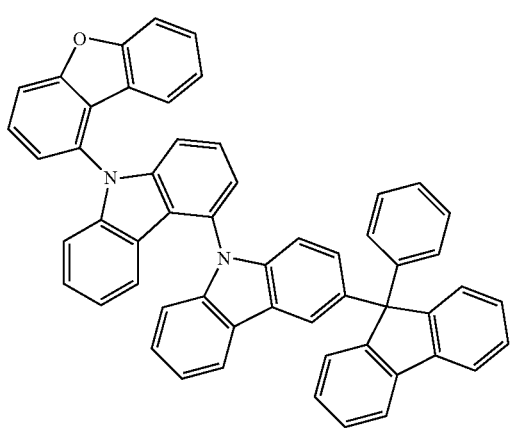
42
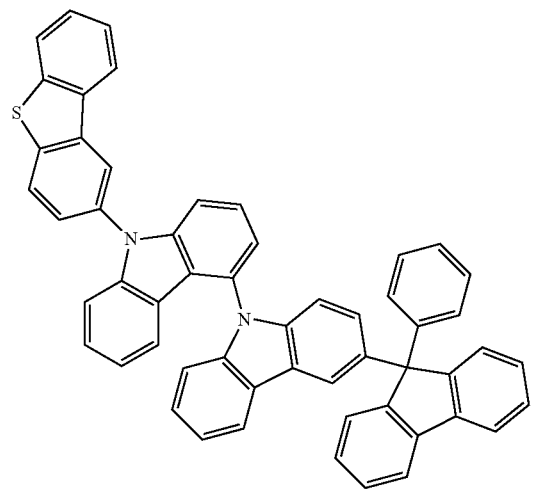
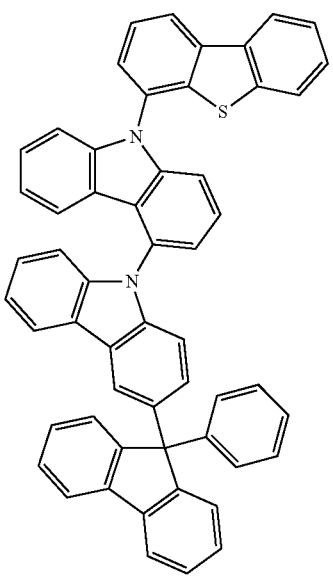
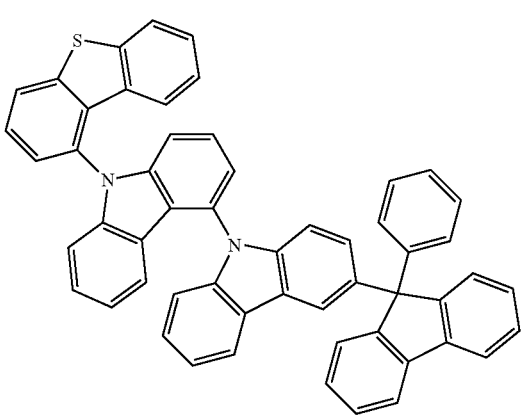

47
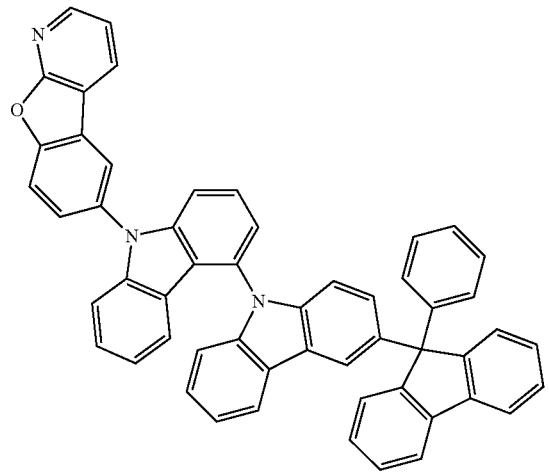
48
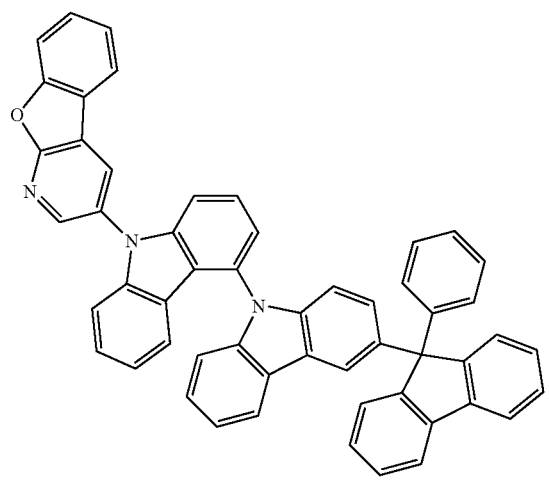
49
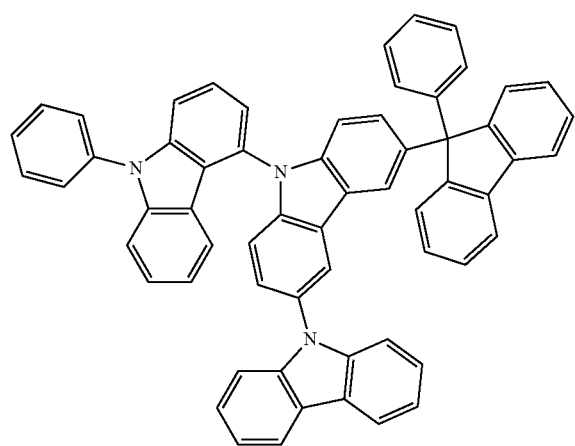
50
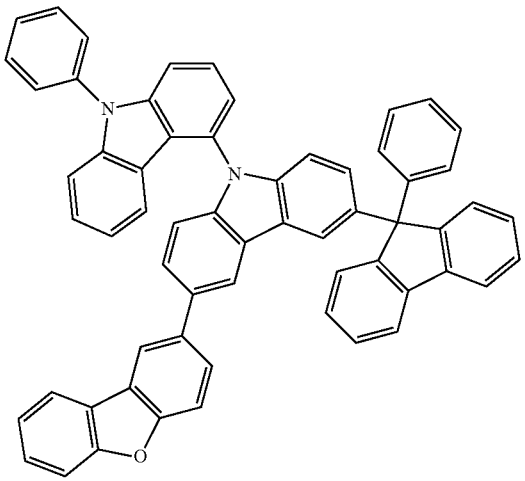
51
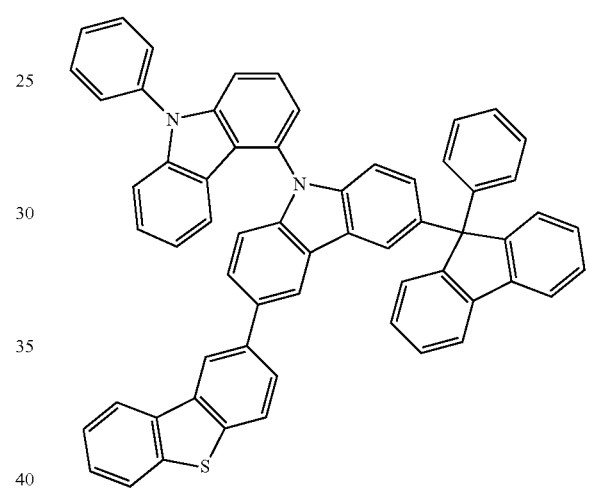
52
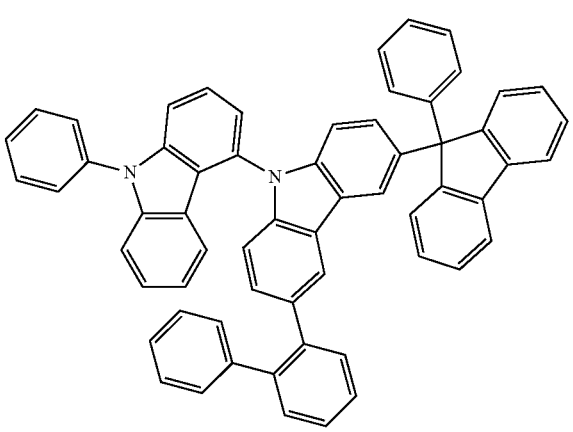

-continued

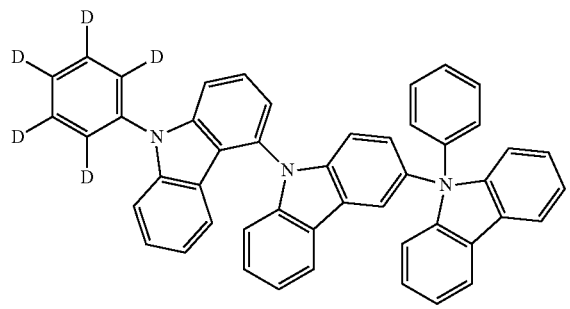
53

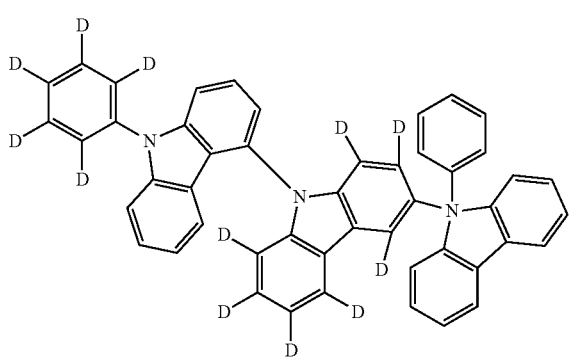
54

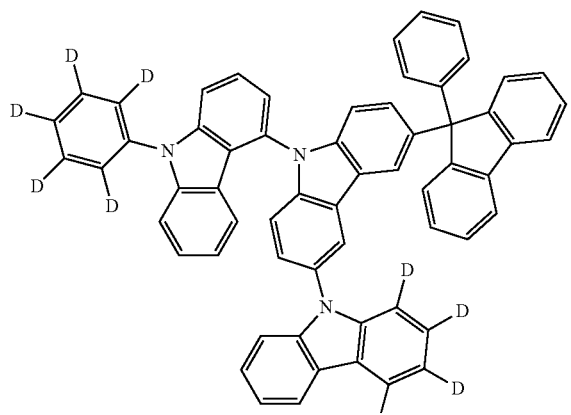
55

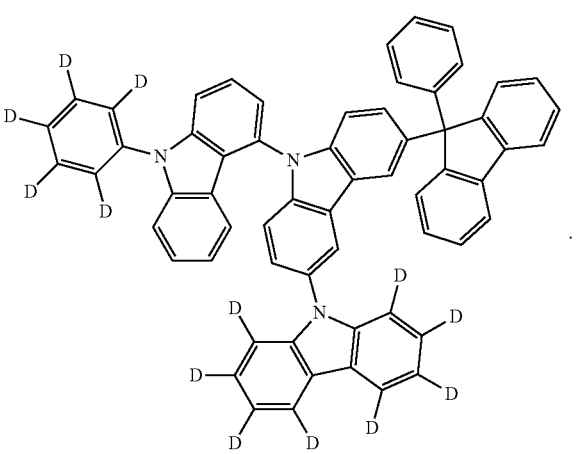
56

The polycyclic compound of the present disclosure includes a fluorene group, a phenyl group connected at a carbon atom at position 9 of a fluorene group, and a carbazole group (e.g., first carbazole group) connected at position 9 of the fluorene group, and includes a diphenyl fluorene skeleton. In addition, at least one carbazole group is connected with the carbazole group (e.g., the first carbazole group), and the hole transport properties of a molecule may be improved, steric hindrance effects may be induced, and a high triplet excitation energy level ($T_1$ level) may be achieved.

The electroluminescence device ED of one or more embodiments may include the polycyclic compound of the present disclosure in the above-described hole transport region HTR as well as the emission layer EML. For example, the polycyclic compound of the present disclosure may be included in the hole transport layer HTL of the hole transport region HTR.

The electroluminescence device ED of one or more embodiments includes the polycyclic compound of the present disclosure in at least one of the emission layer EML or the hole transport region HTR, and may increase the emission efficiency of the device.

In the electroluminescence device ED of one or more embodiments, the emission layer EML may emit at least one of fluorescence, phosphorescence, or thermally activated delayed fluorescence (TADF).

In the electroluminescence device ED of one or more embodiments, the emission layer EML may emit blue light. For example, the emission layer EML may emit light having a central wavelength of about 420 nm to about 470 nm.

In electroluminescence devices ED of embodiments, shown in FIG. 3 to FIG. 6, an emission layer EML may include a host and a dopant. The emission layer EML of one or more embodiments may include the polycyclic compound of one or more embodiments as a host.

In the electroluminescence device ED of one or more embodiments, the emission layer EML may further include any suitable host material. For example, in the electroluminescence device ED, the emission layer EML may include anthracene derivative(s), pyrene derivative(s), fluoranthene derivative(s), chrysene derivative(s), dihydrobenzanthracene derivative(s), and/or triphenylene derivative(s). For example, the emission layer EML may include anthracene derivative(s) and/or pyrene derivative(s).

In electroluminescence devices ED of embodiments, shown in FIG. 3 to FIG. 6, an emission layer EML may include a host and a dopant, and the emission layer EML may include a compound represented by Formula E-1 below. The compound represented by Formula E-1 below may be used as a fluorescence host material:

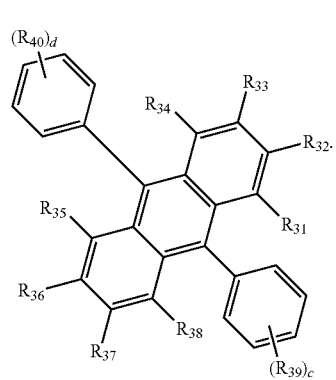

Formula E-1

In Formula E-1, $R_{31}$ to $R_{40}$ may be each independently a hydrogen atom, a deuterium atom, a halogen atom, a substituted or unsubstituted silyl group, a substituted or unsubstituted alkyl group of 1 to 10 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. $R_{31}$ to $R_{40}$ may be combined with an adjacent group to form a saturated hydrocarbon ring or unsaturated hydrocarbon ring.

In Formula E-1, "c" and "d" may be each independently an integer of 0 to 5.

The compound represented by Formula E-1 may be any one represented by Compound E1 to Compound E19 below:

E1
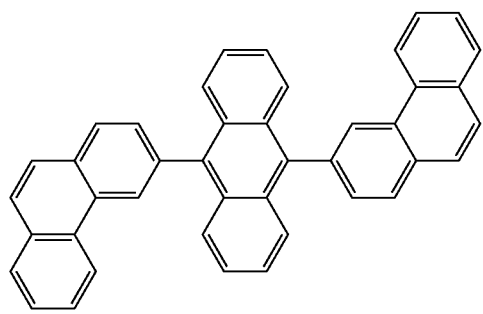

E2
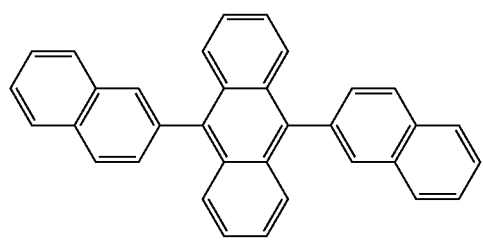

E3
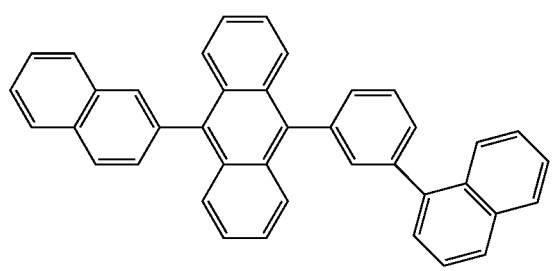

E4
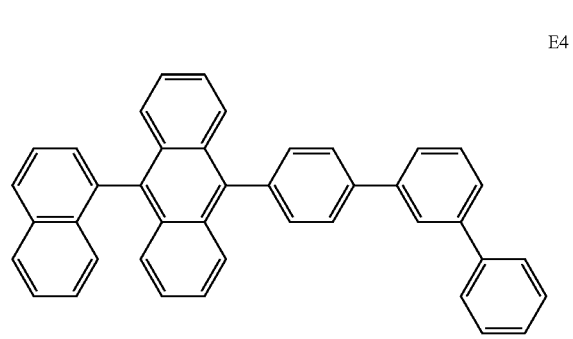

E5
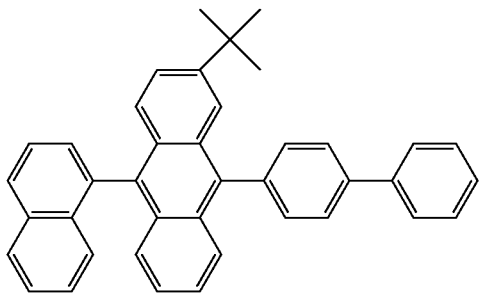

E6
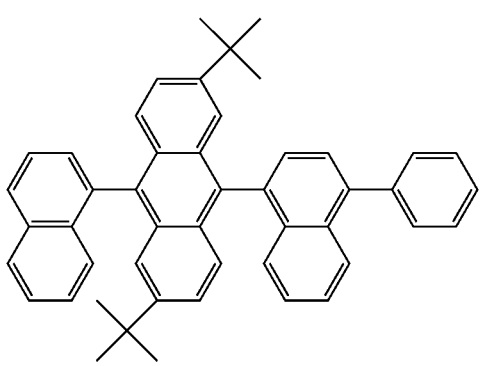

E7
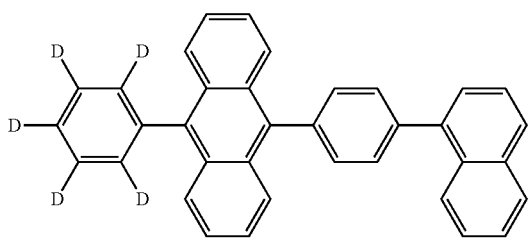

E8
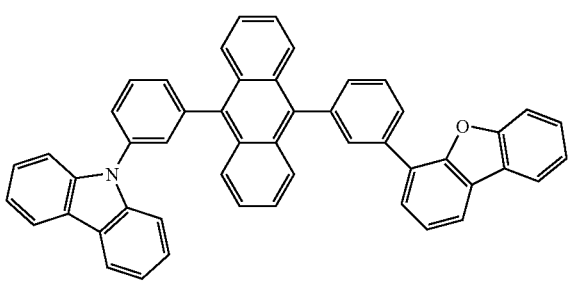

E9
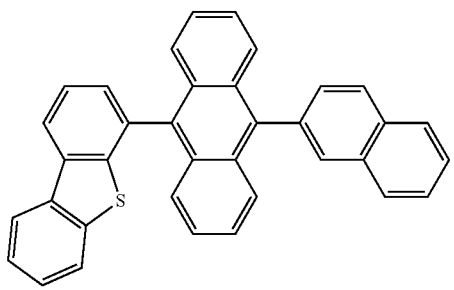

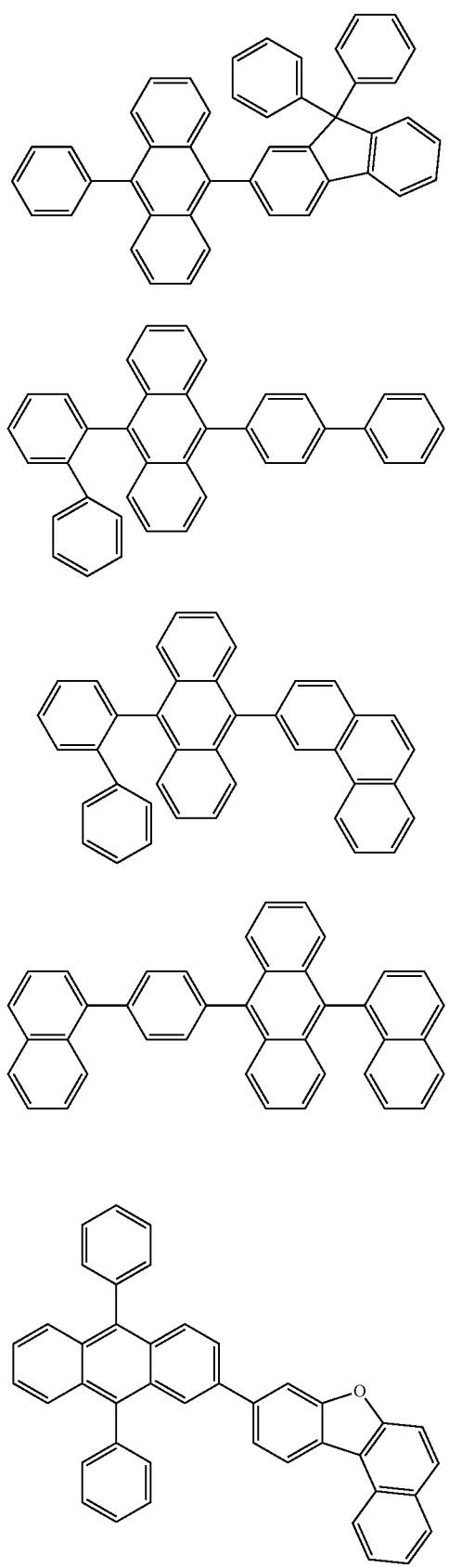

E19

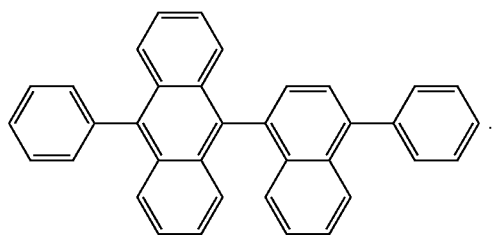

In one or more embodiments, the emission layer EML may include a compound represented by Formula E-2a or Formula E-2b below. The compound represented by Formula E-2a or Formula E-2b may be used as a phosphorescence host material:

Formula E-2a

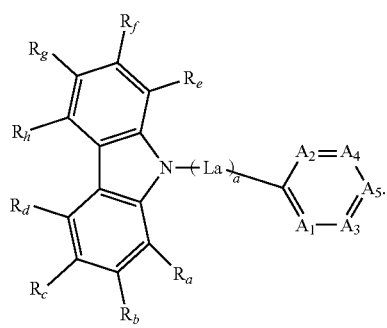

In Formula E-2a, "a" is an integer of 0 to 10, $L_a$ may be a direct linkage, a substituted or unsubstituted arylene group of 6 to 30 ring-forming carbon atoms, or a substituted or unsubstituted heteroarylene group of 2 to 30 ring-forming carbon atoms. If "a" is an integer of 2 or more, multiple (e.g., a plurality of) $L_a$ groups may be each independently a substituted or unsubstituted arylene group of 6 to 30 ring-forming carbon atoms, or a substituted or unsubstituted heteroarylene group of 2 to 30 ring-forming carbon atoms.

In Formula E-2a, $A_1$ to $A_5$ may be each independently N or $CR_i$. $R_a$ to $R_i$ may be each independently a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring. $R_a$ to $R_i$ may be combined with an adjacent group to form a hydrocarbon ring or a heterocycle including N, O, S, etc., as a ring-forming element.

In Formula E-2a, two or three selected from $A_1$ to $A_5$ may be N, and the remainder may be $CR_i$.

Formula E-2b

In Formula E-2b, Cbz1 and Cbz2 may be each independently an unsubstituted carbazole group, or a carbazole group substituted with an aryl group of 6 to 30 ring-forming carbon atoms. $L_b$ may be a direct linkage, a substituted or unsubstituted arylene group of 6 to 30 ring-forming carbon atoms, or a substituted or unsubstituted heteroarylene group of 2 to 30 ring-forming carbon atoms. "b" is an integer of 0 to 10, and if "b" is an integer of 2 or more, multiple (e.g., a plurality of) $L_b$ groups may be each independently a substituted or unsubstituted arylene group of 6 to 30 ring-forming carbon atoms, or a substituted or unsubstituted heteroarylene group of 2 to 30 ring-forming carbon atoms.

The compound represented by Formula E-2a or Formula E-2b may be represented by any one selected from among the compounds in Compound Group E-2 below. However, the compounds in Compound Group E-2 below are illustrations, and the compound represented by Formula E-2a or Formula E-2b is not limited to the compounds represented in Compound Group E-2 below:

Compound Group E-2

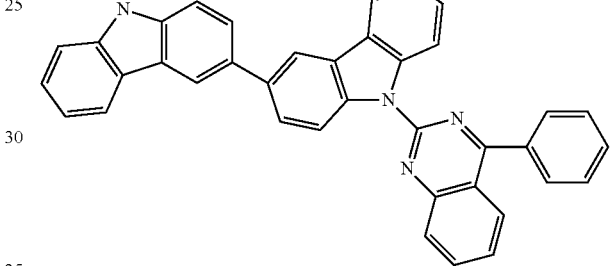

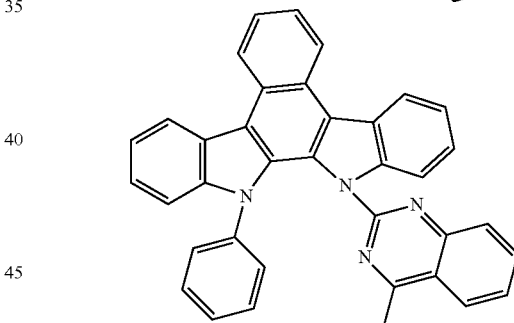

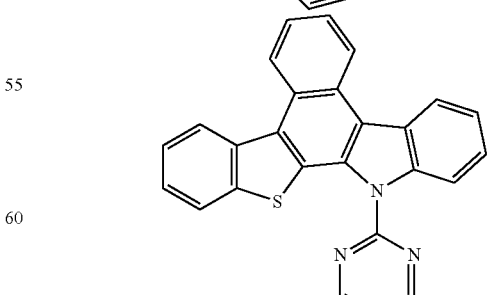

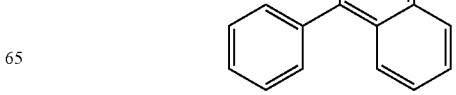

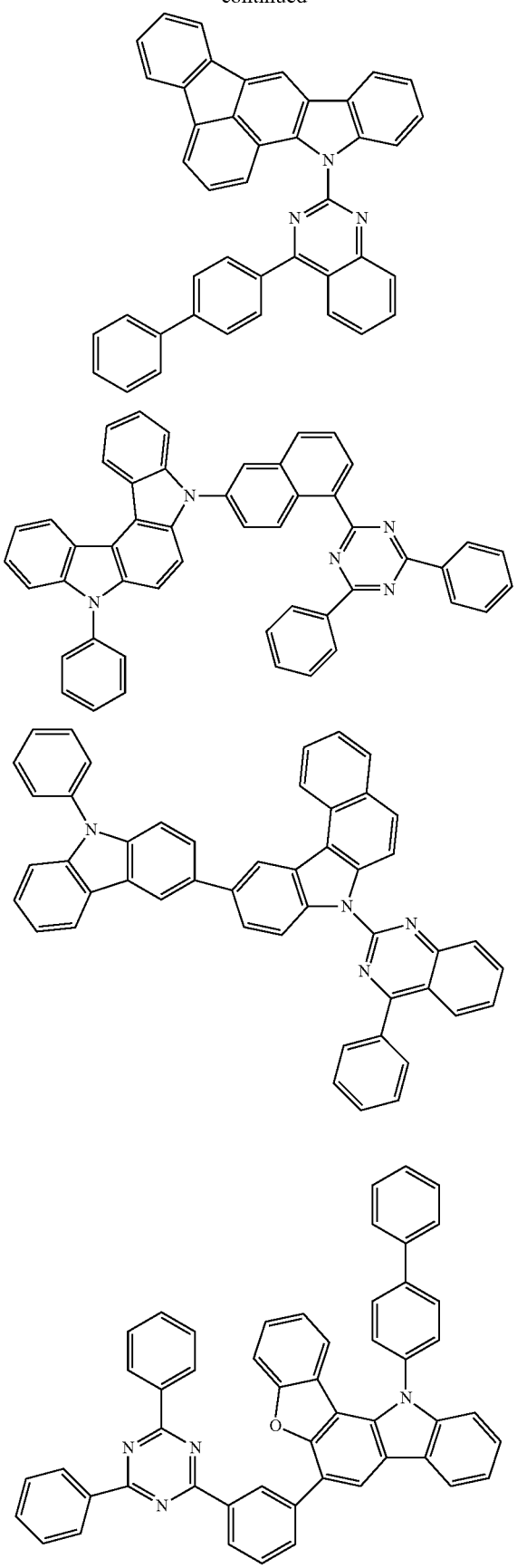

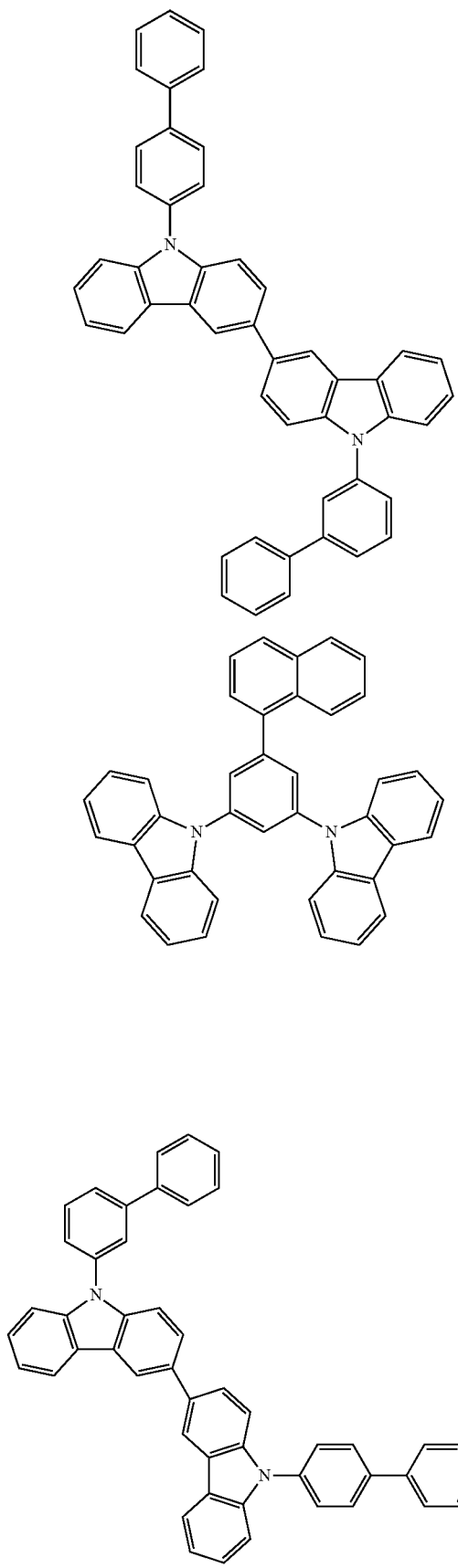
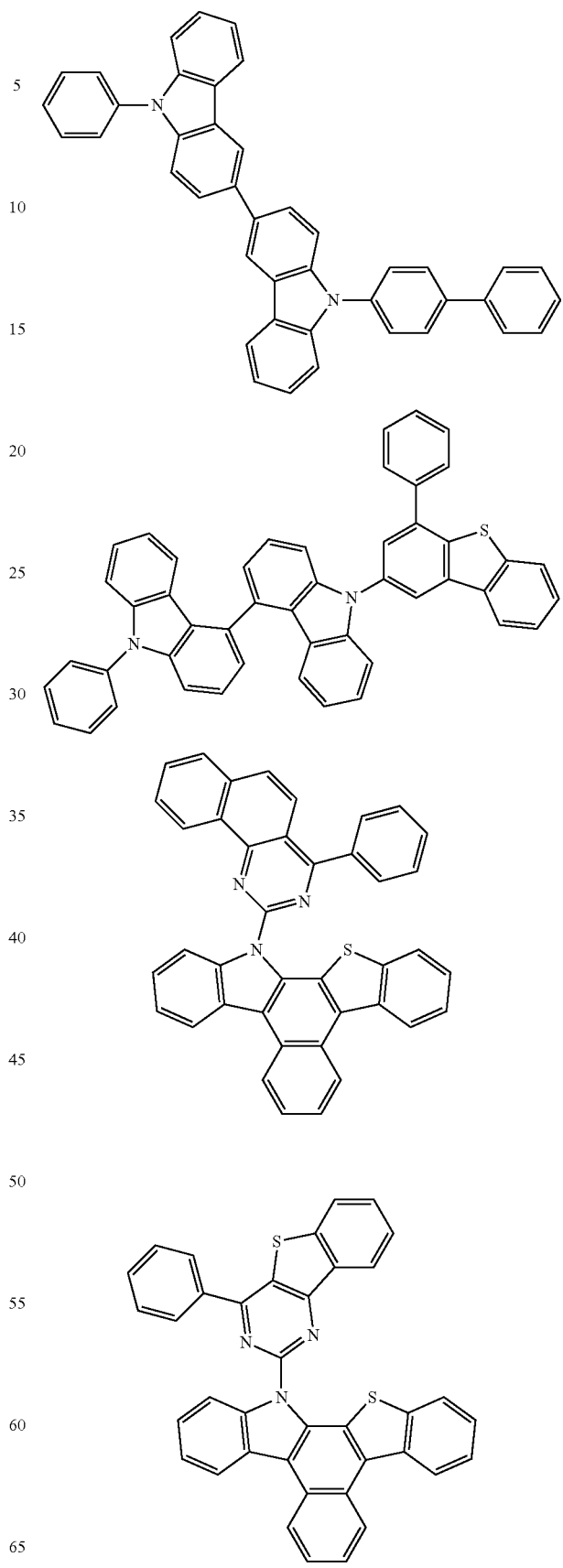

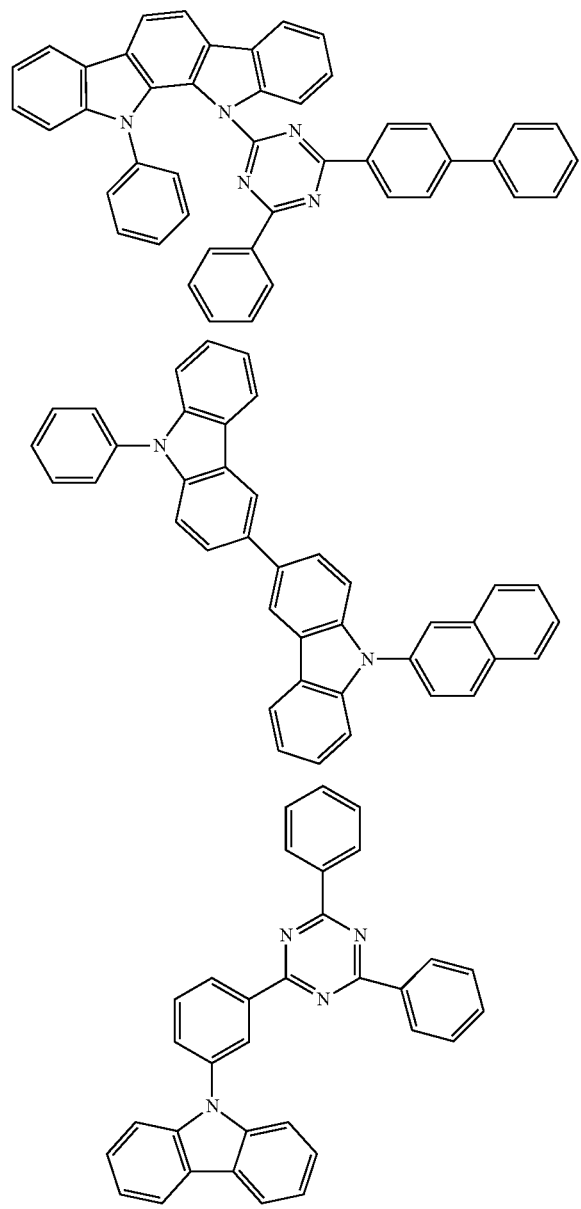

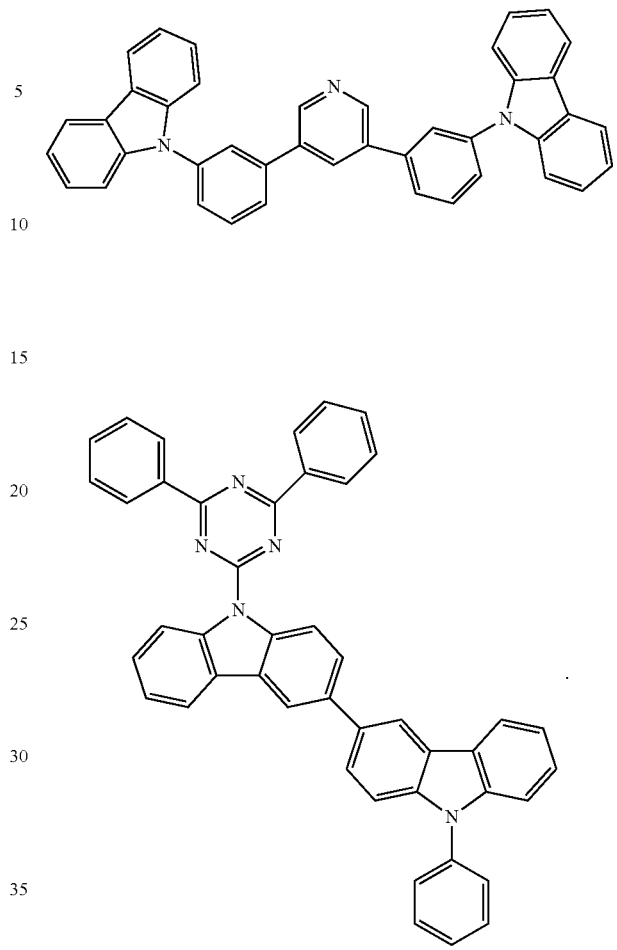

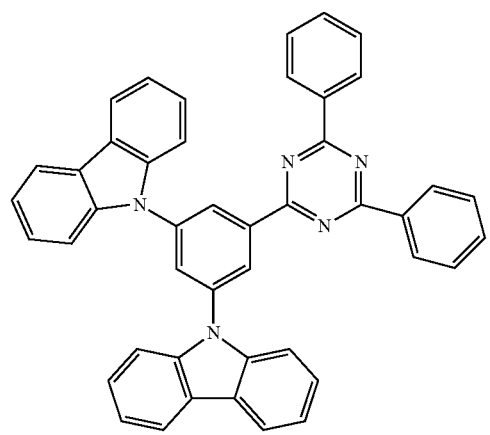

The emission layer EML may further include any suitable material as a host material. For example, the emission layer EML may include, as a host material, at least one of bis[2-(diphenylphosphino)phenyl] ether oxide (DPEPO), 4,4'-bis(carbazol-9-yl)biphenyl (CBP), 1,3-bis(carbazol-9-yl)benzene (mCP), 2,8-bis(diphenyl phosphoryl)dibenzo[b,d]furan (PPF), 4,4',4"-tris(carbazol-9-yl)-triphenylamine (TCTA), or 1,3,5-tris(1-phenyl-1H-benzo[d]imidazole-2-yl) benzene (TPBi). However, embodiments of the present disclosure are not limited thereto. For example, tris(8-hydroxyquinolino)aluminum ($Alq_3$), 4,4'-bis(N-carbazolyl)-1,1'-biphenyl (CBP), poly(N-vinylcarbazole) (PVK), 9,10-di(naphthalene-2-yl)anthracene (ADN), 4,4',4"-tris (carbazol-9-yl)-triphenyamine (TCTA), 1,3,5-tris(N-phenylbenzimidazole-2-yl)benzene (TPBi), 2-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenyl cyclotriphosphazene (CP1), 1,4-bis (triphenylsilyl)benzene (UGH2), hexaphenylcyclotrisiloxane ($DPSiO_3$), octaphenylcyclotetra siloxane ($DPSiO_4$), 2,8-bis(diphenylphosphoryl)dibenzofuran (PPF), etc. may be used as the host material.

The emission layer EML may include a compound represented by Formula M-a or Formula M-b below. The compound represented by Formula M-a or Formula M-b below may be used as a phosphorescence dopant material:

Formula M-a

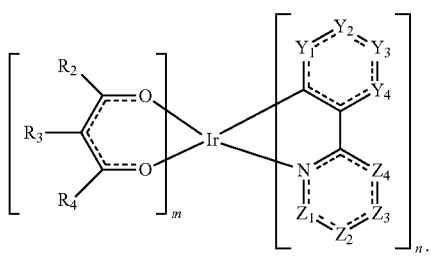

In Formula M-a above, $Y_1$ to $Y_4$, and $Z_1$ to $Z_4$ may be each independently $CR_1$ or N, and $R_1$ to $R_4$ may be each independently a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Formula M-a, "m" is 0 or 1, and "n" is 2 or 3. In Formula M-a, if "m" is 0, "n" is 3, and if "m" is 1, "n" is 2.

The compound represented by Formula M-a may be used as a red phosphorescence dopant or a green phosphorescence dopant.

The compound represented by Formula M-a may be represented by any one selected from among Formula M-a1 to Formula M-a19 below. However, Formula M-a1 to Formula M-a19 below are only illustrations, and the compound represented by Formula M-a is not limited to the compounds represented by Formula M-a1 to Formula M-a19 below:

M-a1

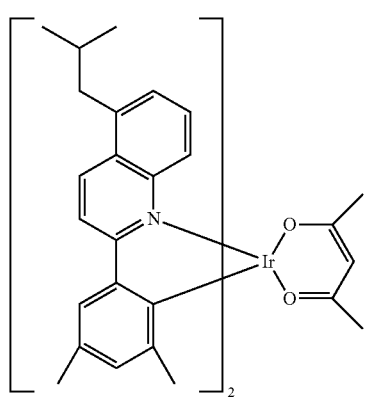

M-a2

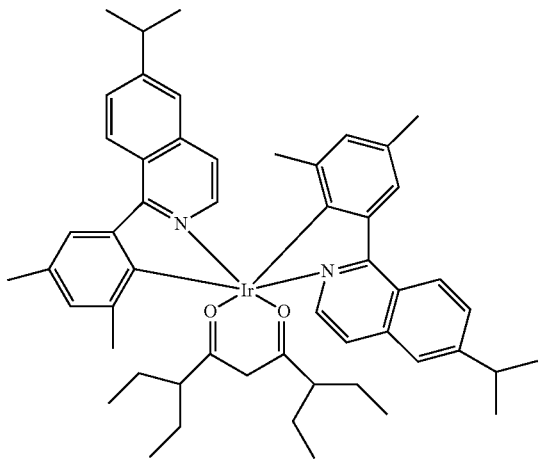

M-a3

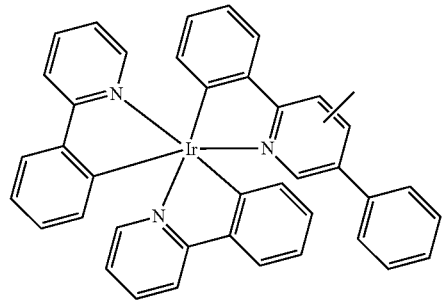

Ma-4

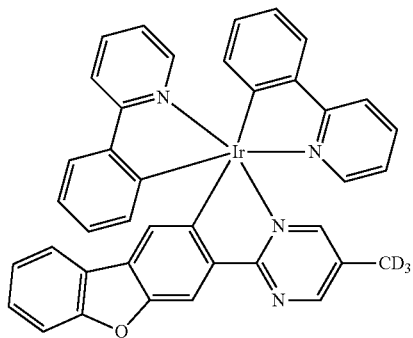

M-a5

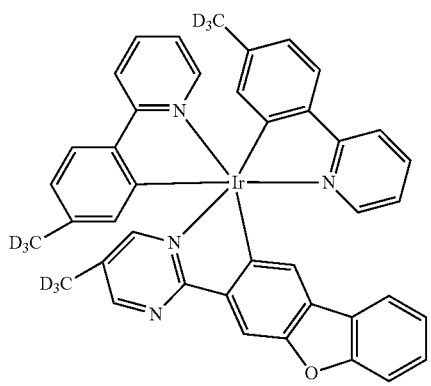

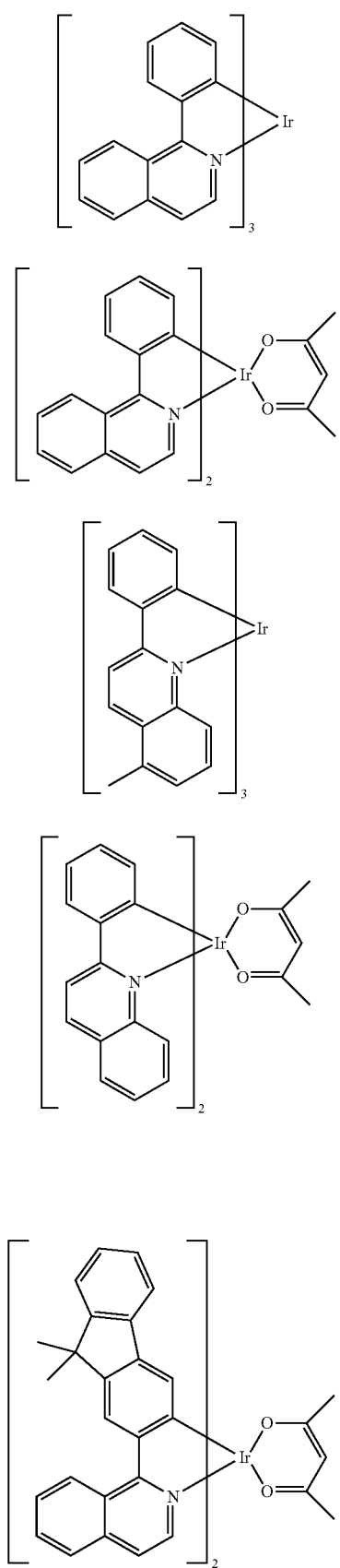
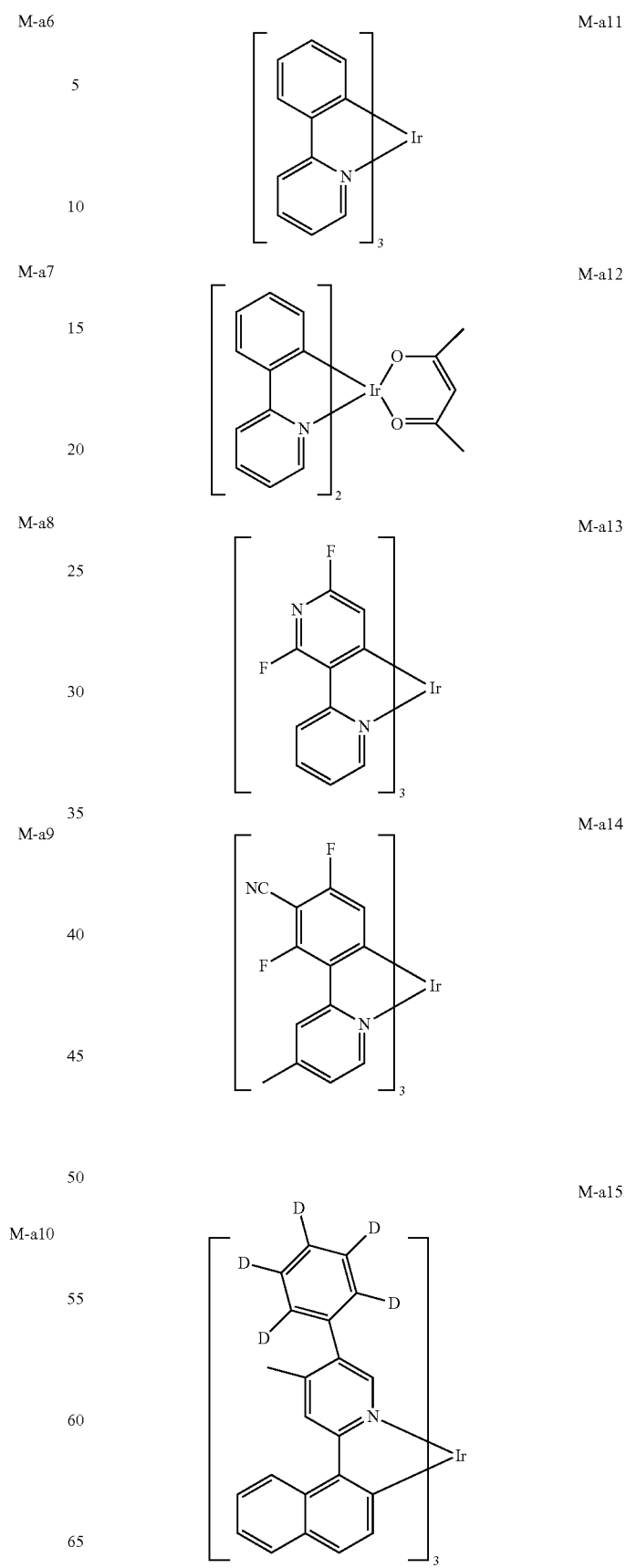

M-a16

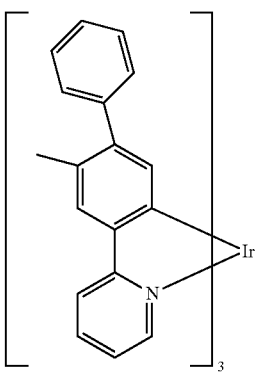

M-a17

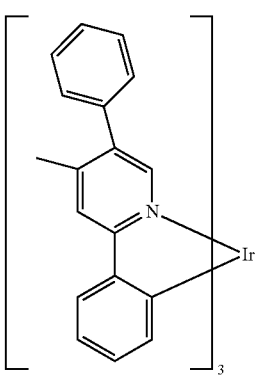

M-a18

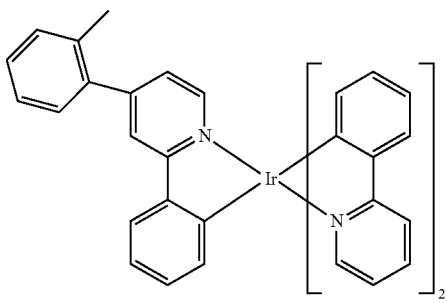

M-a19

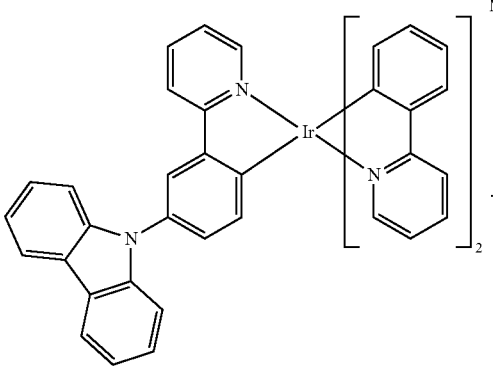

Formula M-a1 and Formula M-a2 may be used as red dopant materials, and Formula M-a3 to Formula M-a5 may be used as green dopant materials.

Formula M-b

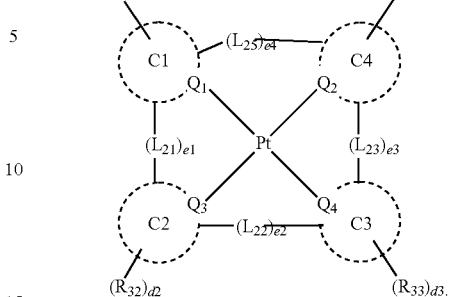

In Formula M-b, $Q_1$ to $Q_4$ may be each independently C or N, and C1 to C4 may be each independently a substituted or unsubstituted hydrocarbon ring of 5 to 30 ring-forming carbon atoms, or a substituted or unsubstituted heterocycle of 2 to 30 ring-forming carbon atoms. $L_{21}$ to $L_{24}$ may be each independently a direct linkage, *—O—*, *—S—*,

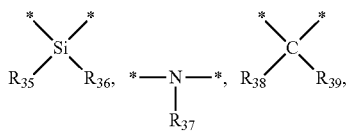

a substituted or unsubstituted alkyl group of 1 to 20 carbon atoms, a substituted or unsubstituted arylene group of 6 to 30 ring-forming carbon atoms, or a substituted or unsubstituted heteroarylene group of 2 to 30 ring-forming carbon atoms, and e1 to e4 are each independently 0 or 1. $R_{31}$ to $R_{39}$ may be each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring, and d1 to d4 may be each independently an integer of 0 to 4.

The compound represented by Formula M-b may be used as a blue phosphorescence dopant or a green phosphorescence dopant.

The compound represented by Formula M-b may be represented by any one selected from among the compounds below. However, the compounds are illustrations, and the compound represented by Formula M-b is not limited thereto:

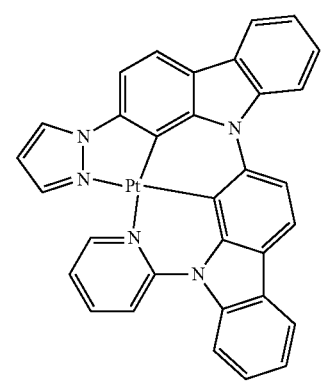
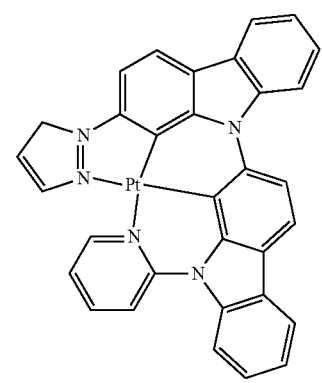
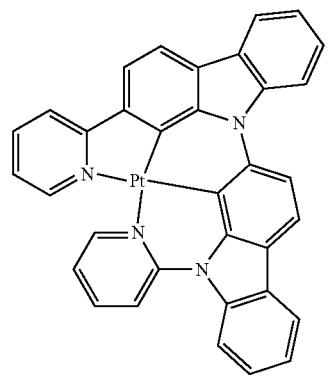
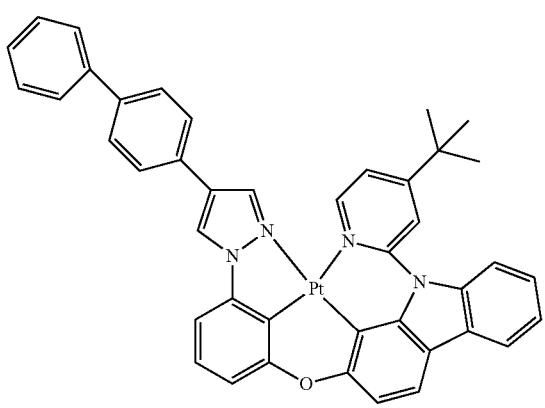
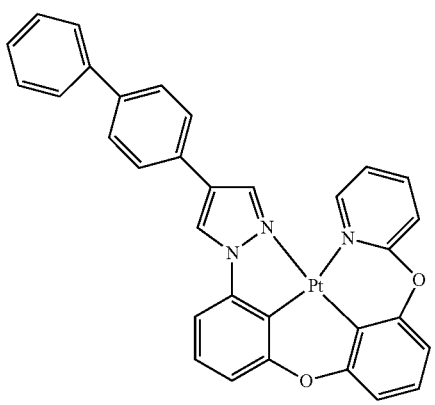
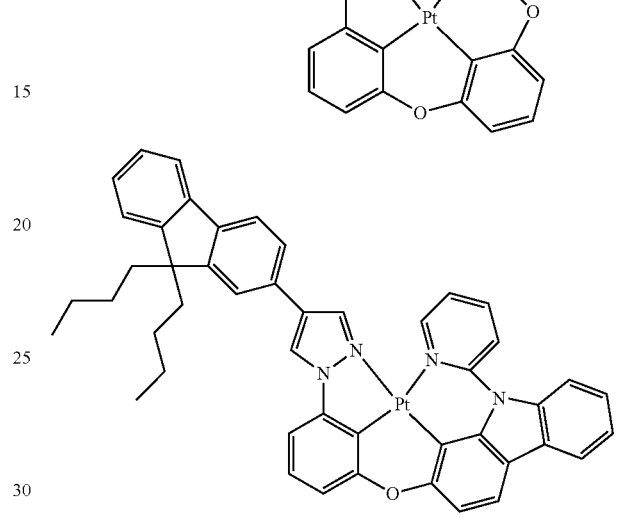
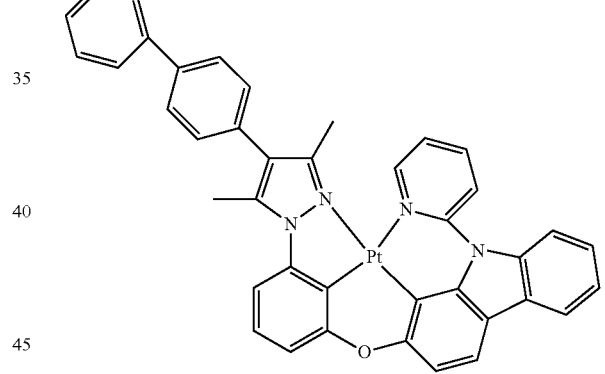
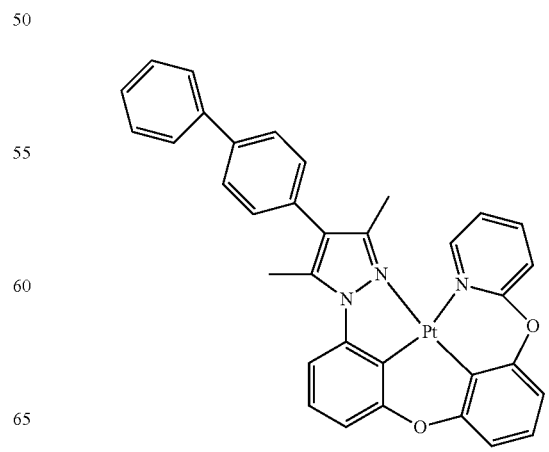

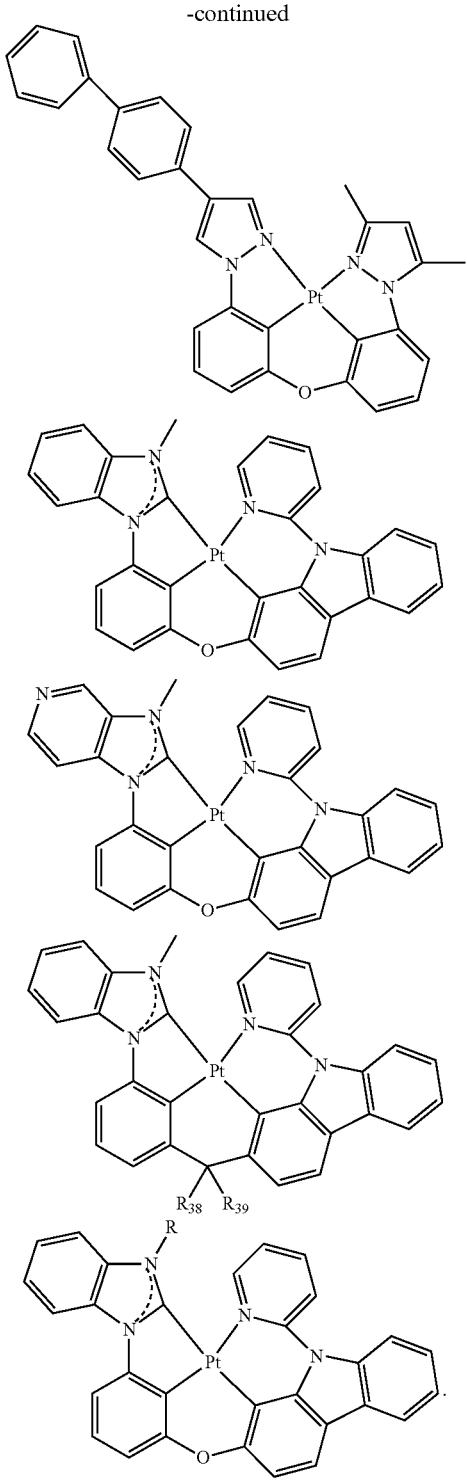

In the compounds above, R, $R_{38}$, and $R_{39}$ may be each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

The emission layer EML may include a compound represented by any one selected from among Formula F-a to Formula F-c below. The compounds represented by Formula F-a to Formula F-c below may be used as fluorescence dopant materials:

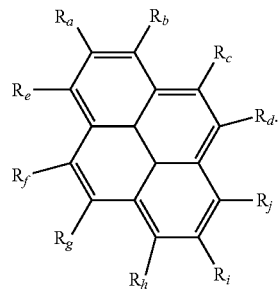

Formula F-a

In Formula F-a, two selected from $R_a$ to $R_j$ may be each independently substituted with *—$NAr_1Ar_2$. The remainder not substituted with *—$NAr_1Ar_2$ among $R_a$ to $R_j$ may be each independently a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. In *—$NAr_1Ar_2$, $Ar_1$ and $Ar_2$ may be each independently a substituted or unsubstituted aryl group of 6 to 30 ring-forming carbon atoms, or a substituted or unsubstituted heteroaryl group of 2 to 30 ring-forming carbon atoms. For example, at least one selected from among $Ar_1$ and $Ar_2$ may be a heteroaryl group including O or S as a ring-forming atom.

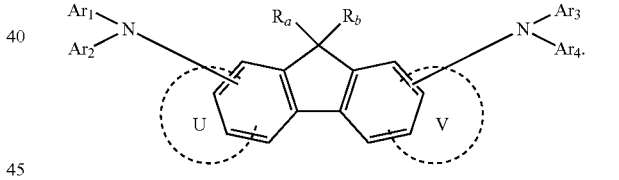

Formula F-b

In Formula F-b, Ra and Rb may be each independently a hydrogen atom, a deuterium atom, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be each independently combined with an adjacent group to form a ring.

In Formula F-b, U and V may be each independently a substituted or unsubstituted hydrocarbon ring of 5 to 30 ring-forming carbon atoms, or a substituted or unsubstituted heterocycle of 2 to 30 ring-forming carbon atoms.

In Formula F-b, the number of rings represented by U and V may be each independently 0 or 1. For example, in Formula F-b, if the number of U or V is 1, one ring forms a fused ring at the designated part by U or V, and if the number of U or V is 0, a ring is not present at the designated part by U or V. For example, if the number of U is 0, and the number of V is 1, or if the number of U is 1, and the number of V is 0, a fused ring having the fluorene core of Formula F-b may be a ring compound with four rings. if the number of both U and V is 0, the fused ring of Formula F-b may be a ring compound with three rings. If the number of both U and V is 1, a fused ring having the fluorene core of Formula F-b may be a ring compound with five rings.

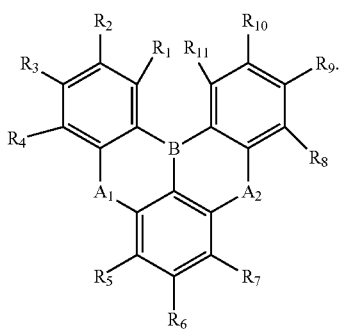

Formula F-c

In Formula F-c, $A_1$ and $A_2$ may be each independently O, S, Se, or $NR_m$, and $R_m$ may be a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. $R_1$ to $R_{11}$ may be each independently a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring.

In Formula F-c, $A_1$ and $A_2$ may be each independently combined with the substituents of an adjacent ring to form a fused ring. For example, if $A_1$ and $A_2$ are each independently $NR_m$, $A_1$ may be combined with $R_4$ or $R_5$ to form a ring. In addition, $A_2$ may be combined with $R_7$ or $R_8$ to form a ring.

In one or more embodiments, the emission layer EML may include, as a dopant material, styryl derivative(s) (for example, 1,4-bis[2-(3-N-ethylcarbazoryl)vinyl]benzene (BCzVB), 4-(di-p-tolylamino)-4'-[(di-p-tolylamino)styryl] stilbene (DPAVB), N-(4-((E)-2-(6-((E)-4-(diphenylamino) styryl)naphthalen-2-yl)vinyl)phenyl)-N-phenylbenzenamine (N-BDAVBi) and 4,4'-bis[2-(4-(N,N-diphenylamino)phenyl)vinyl]biphenyl (DPAVBi)), perylene and/or the derivative(s) thereof (for example, 2,5,8,11-tetrat-butylperylene (TBP)), pyrene and/or the derivative(s) thereof (for example, 1,1-dipyrene, 1,4-dipyrenylbenzene, 1,4-bis(N,N-diphenylamino)pyrene), etc.

The emission layer EML may include a suitable phosphorescence dopant material. For example, the phosphorescent dopant may use a metal complex including iridium (Ir), platinum (Pt), osmium (Os), gold (Au), titanium (Ti), zirconium (Zr), hafnium (Hf), europium (Eu), terbium (Tb) or thulium (Tm). For example, iridium (III) bis(4,6-difluorophenylpyridinato-N,$C^2$Ç (Bis[2-(4,6-difluorophenyl)pyridinato-C2,N](picolinato)iridium (III) or Flrpic), bis(2,4-difluorophenylpyridinato)-tetrakis(1-pyrazolyl)borate iridium (III) (Fir6), or platinum octaethyl porphyrin (PtOEP) may be used as the phosphorescence dopant. However, embodiments of the present disclosure are not limited thereto.

The emission layer EML may include a quantum dot material. The core of the quantum dot may be selected from II-VI group compounds, III-V group compounds, IV-VI group compounds, IV group elements, IV group compounds, and combinations thereof.

The II-VI group compound may be selected from the group consisting of a binary compound selected from the group consisting of CdSe, CdTe, CdS, ZnS, ZnSe, ZnTe, ZnO, HgS, HgSe, HgTe, MgSe, MgS, and mixtures thereof; a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and mixtures thereof; and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and mixtures thereof.

The III-VI group compound may include a binary compound such as $In_2S_3$ and/or $In_2Se_3$; a ternary compound such as $InGaS_3$ and/or $InGaSe_3$, or optional combinations thereof.

The I-III-VI group compound may be a ternary compound selected from the group consisting of AgInS, $AgInS_2$, CuInS, $CuInS_2$, $AgGaS_2$, $CuGaS_2$, $CuGaO_2$, $AgGaO_2$, $AgAlO_2$ and mixtures thereof; or a quaternary compound such as $AgInGaS_2$ and/or $CuInGaS_2$.

The III-V group compound may be selected from the group consisting of a binary compound selected from the group consisting of GaN, GaP, GaAs, GaSb, AlN, AlP, AlAs, AlSb, InN, InP, InAs, InSb, and mixtures thereof; a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and mixtures thereof; and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and mixtures thereof. In one or more embodiments, the III-V group compound may further include a metal in group II. For example, InZnP, etc., may be selected as the III-II-V group compound.

The IV-VI group compound may be selected from the group consisting of a binary compound selected from the group consisting of SnS, SnSe, SnTe, PbS, PbSe, PbTe, and mixtures thereof; a ternary compound selected from the group consisting of SnSeS, SnSeTe, SnSTe, PbSeS, PbSeTe, PbSTe, SnPbS, SnPbSe, SnPbTe, and mixtures thereof; and a quaternary compound selected from the group consisting of SnPbSSe, SnPbSeTe, SnPbSTe, and mixtures thereof. The IV group element may be selected from the group consisting of Si, Ge, and mixtures thereof. The IV group compound may be a binary compound selected from the group consisting of SiC, SiGe, and mixtures thereof.

In the one or more embodiments, the binary compound, the ternary compound and/or the quaternary compound may be present at uniform concentration in a particle or may be present at a partially different concentration distribution state in the same particle. In one or more embodiments, a core/shell structure in which one quantum dot wraps another quantum dot may be possible. The core/shell structure may have a concentration gradient in which the concentration of an element present in the shell decreases toward a center.

In some embodiments, the quantum dot may have a core-shell structure including a core including a nanocrystal and a shell wrapping the core. The shell of the quantum dot may play the role of a protection layer for preventing or reducing the chemical deformation of the core to maintain semiconductor properties and/or a charging layer for imparting the quantum dot with electrophoretic properties. The shell may have a single layer or a multilayer. Examples of the shell of the quantum dot may include a metal oxide, a non-metal oxide, a semiconductor compound, or combinations thereof.

For example, the metal oxide or non-metal oxide may each independently include a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$ and/or NiO; or a ternary compound such as $MgAl_2O_4$, $CoFe_2O_4$, $NiFe_2O_4$ and/or $CoMn_2O_4$, but embodiments of the present disclosure are not limited thereto.

In one or more embodiments, the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but embodiments of the present disclosure are not limited thereto.

The quantum dot may have a full width of half maximum (FWHM) of emission wavelength spectrum of about 45 nm or less, for example, about 40 nm or less, or about 30 nm or less. Within any of these ranges, color purity and/or color reproducibility may be improved. In addition, light emitted via such quantum dot is emitted in all directions, and light view angle may be improved.

The shape of the quantum dot may be any suitable shape in the art, without specific limitation. For example, the shape of spherical, pyramidal, multi-arm, and/or cubic nanoparticle, nanotube, nanowire, nanofiber, nanoplate particle, etc. may be used.

The quantum dot may control the color of emitted light (e.g., light to be emitted) according to the particle size, and accordingly, the quantum dot may have various emission colors such as blue, red and/or green.

In the electroluminescence devices ED of embodiments, as shown in FIG. 3 to FIG. 6, the electron transport region ETR is provided on the emission layer EML. The electron transport region ETR may include at least one of an electron blocking layer HBL, an electron transport layer ETL or an electron injection layer EIL. However, embodiments of the present disclosure are not limited thereto.

The electron transport region ETR may have a single layer formed using (e.g., consisting of) a single material, a single layer formed using multiple different materials, or a multilayer structure having multiple layers formed using multiple different materials.

For example, the electron transport region ETR may have a single layer structure of an electron injection layer EIL or an electron transport layer ETL, or a single layer structure formed using an electron injection material and an electron transport material. In one or more embodiments, the electron transport region ETR may have a single layer structure having multiple different materials, or a structure stacked from the emission layer EML of electron transport layer ETL/electron injection layer EIL, or hole blocking layer HBL/electron transport layer ETL/electron injection layer EIL, without limitation. The thickness of the electron transport region ETR may be, for example, from about 1,000 Å to about 1,500 Å.

The electron transport region ETR may be formed using one or more suitable methods such as a vacuum deposition method, a spin coating method, a cast method, a Langmuir-Blodgett (LB) method, an inkjet printing method, a laser printing method, and/or a laser induced thermal imaging (LITI) method.

The electron transport region ETR may include a compound represented by Formula ET-1 below:

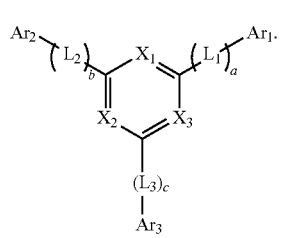

Formula ET-1

In Formula ET-1, at least one selected from among $X_1$ to $X_3$ is N, and the remainder are $CR_a$. $R_a$ may be a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. $Ar_1$ to $Ar_3$ may be each independently a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

In Formula ET-1, "a" to "c" may be each independently an integer of 0 to 10. In Formula ET-1, $L_1$ to $L_3$ may be each independently a direct linkage, a substituted or unsubstituted arylene group of 6 to 30 ring-forming carbon atoms, or a substituted or unsubstituted heteroarylene group of 2 to 30 ring-forming carbon atoms. Meanwhile, if "a" to "c" are integers of 2 or more, $L_1$ to $L_3$ may be each independently a substituted or unsubstituted arylene group of 6 to 30 ring-forming carbon atoms, or a substituted or unsubstituted heteroarylene group of 2 to 30 ring-forming carbon atoms.

The electron transport region ETR may include an anthracene-based compound. However, embodiments of the present disclosure are not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-yl) phenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate ($Bebq_2$), 9,10-di(naphthalene-2-yl)anthracene (ADN), 1,3-bis[3,5-di(pyridin-3-yl)phenyl]benzene (BmPyPhB), and mixtures thereof, without limitation.

In one or more embodiments, the electron transport region ETR may include a metal halide such as LiF, NaCl, CsF, RbCl, RbI, CuI and/or KI; a metal in lanthanoides such as Yb; or a co-depositing material of the metal halide and the metal in lanthanoides. For example, the electron transport region ETR may include KI:Yb, RbI:Yb, etc., as the co-depositing material. In one or more embodiments, the electron transport region ETR may use a metal oxide such as $Li_2O$ and/or BaO, and/or 8-hydroxy-lithium quinolate (Liq). However, embodiments of the present disclosure are not limited thereto. The electron transport region ETR may also be formed using a mixture material of an electron transport material and an insulating organo metal salt. The organo metal salt may be a material having an energy band gap of about 4 eV or more. For example, the organo metal salt may include, for example, metal acetate(s), metal benzoate(s), metal acetoacetate(s), metal acetylacetonate(s), and/or metal stearate(s).

The electron transport region ETR may further include at least one of 2,9-dimethyl-4,7-diphenyl-1,10-phenanthroline (BCP), or 4,7-diphenyl-1,10-phenanthroline (Bphen). However, embodiments of the present disclosure are not limited thereto.

The electron transport region ETR may include the compounds of the electron transport region in at least one selected from among an electron injection layer EIL, an electron transport layer ETL, and a hole blocking layer HBL.

If the electron transport region ETR includes the electron transport layer ETL, the thickness of the electron transport layer ETL may be from about 100 Å to about 1,000 Å, for example, from about 150 Å to about 500 Å. If the thickness of the electron transport layer ETL satisfies any of the above-described ranges, satisfactory (or suitable) electron transport properties may be obtained without substantial increase of a driving voltage. If the electron transport region ETR includes the electron injection layer EIL, the thickness of the electron injection layer EIL may be from about 1 Å to about 100 Å, for example, from about 3 Å to about 90 Å. If the thickness of the electron injection layer EIL satisfies any of the above described ranges, satisfactory (or suitable) electron injection properties may be obtained without inducing a substantial increase of a driving voltage.

The second electrode EL2 is provided on the electron transport region ETR. The second electrode EL2 may be a common electrode. The second electrode EL2 may be a cathode or an anode, but embodiments of the present disclosure are not limited thereto. For example, if the first electrode EL1 is an anode, the second cathode EL2 may be a cathode, and if the first electrode EL1 is a cathode, the second electrode EL2 may be an anode.

The second electrode EL2 may be a transmissive electrode, a transflective electrode or a reflective electrode. If the second electrode EL2 is the transmissive electrode, the second electrode EL2 may include a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, Yb, W, a compound thereof, or a mixture thereof (for example, AgMg, AgYb, and/or MgAg). The second electrode EL2 may have a multilayered structure including a reflective layer or a transflective layer formed using any of the above-described materials and a transparent conductive layer formed using ITO, IZO, ZnO, ITZO, etc. For example, the second electrode EL2 may include the aforementioned metal materials, combinations of two or more metal materials selected from the aforementioned metal materials, and/or oxides of the aforementioned metal materials.

In one or more embodiments, the second electrode EL2 may be connected (e.g., coupled) with an auxiliary electrode. If the second electrode EL2 is connected (e.g., coupled) with the auxiliary electrode, the resistance of the second electrode EL2 may decrease.

On the second electrode EL2 in the electroluminescence device ED of one or more embodiments, a capping layer CPL may be further disposed (e.g., provided). The capping layer CPL may include a multilayer or a single layer.

In one or more embodiments, the capping layer CPL may be an organic layer or an inorganic layer. For example, if the capping layer CPL includes an inorganic material, the inorganic material may include an alkali metal compound such as LiF, an alkaline earth metal compound such as $MgF_2$, SiON, SiNx, SiOy, etc.

For example, if the capping layer CPL includes an organic material, the organic material may include α-NPD, NPB, TPD, m-MTDATA, $Alq_3$, CuPc, N4,N4,N4',N4'-tetra(biphenyl-4-yl) biphenyl-4,4'-diamine (TPD15), 4,4',4"-tris(carbazol sol-9-yl) triphenylamine (TCTA), etc., or may include an epoxy resin, or an acrylate such as methacrylate. In one or more embodiments, Compounds P1 to P5 below may be included in the capping layer CPL, but embodiments of the present disclosure are not limited thereto.

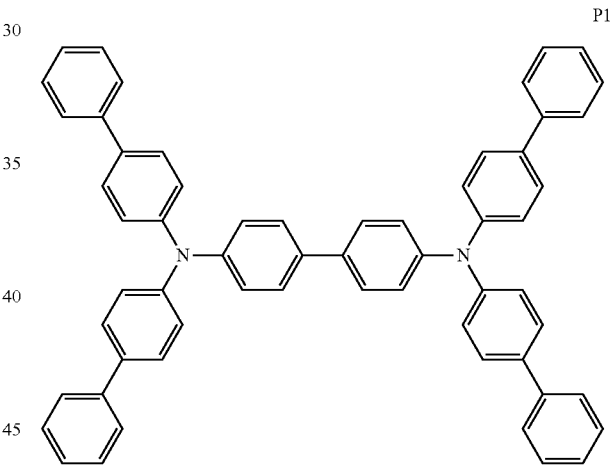

P1

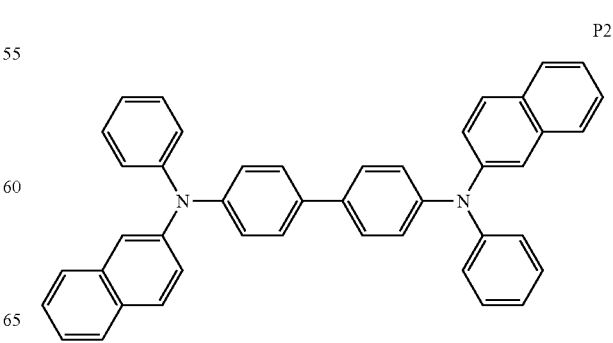

P2

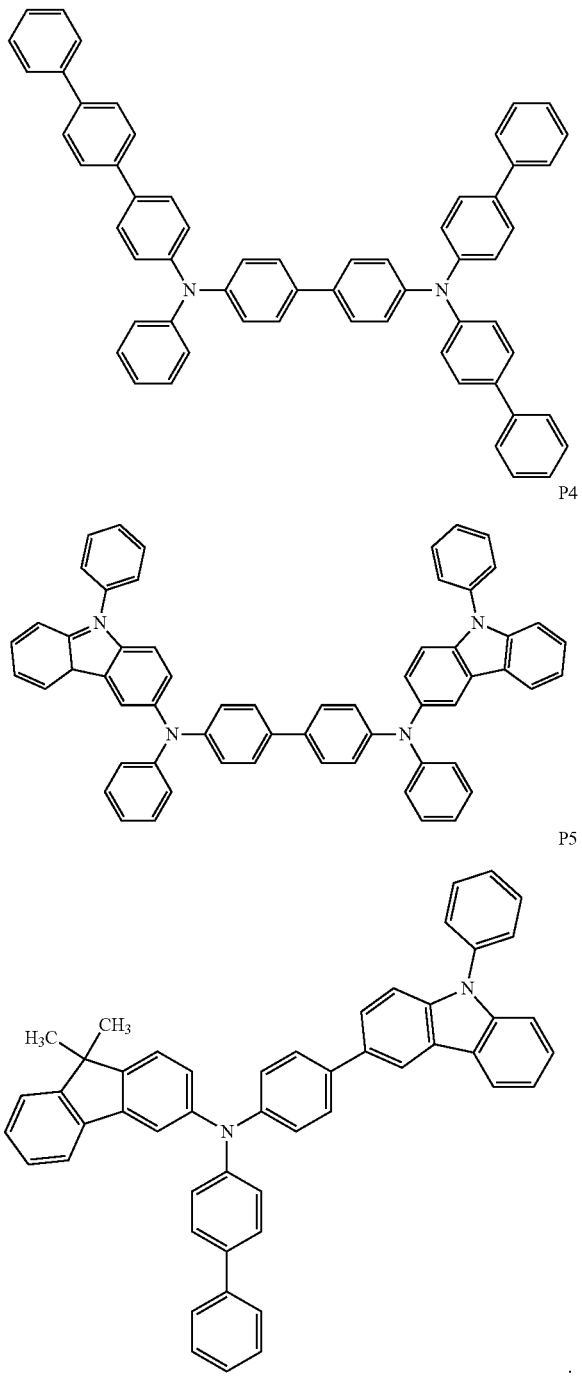

The refractive index of the capping layer CPL may be about 1.6 or more. For example, the refractive index of the capping layer CPL with respect to light in a wavelength range of about 550 nm to about 660 nm may be about 1.6 or more.

Figure 7:
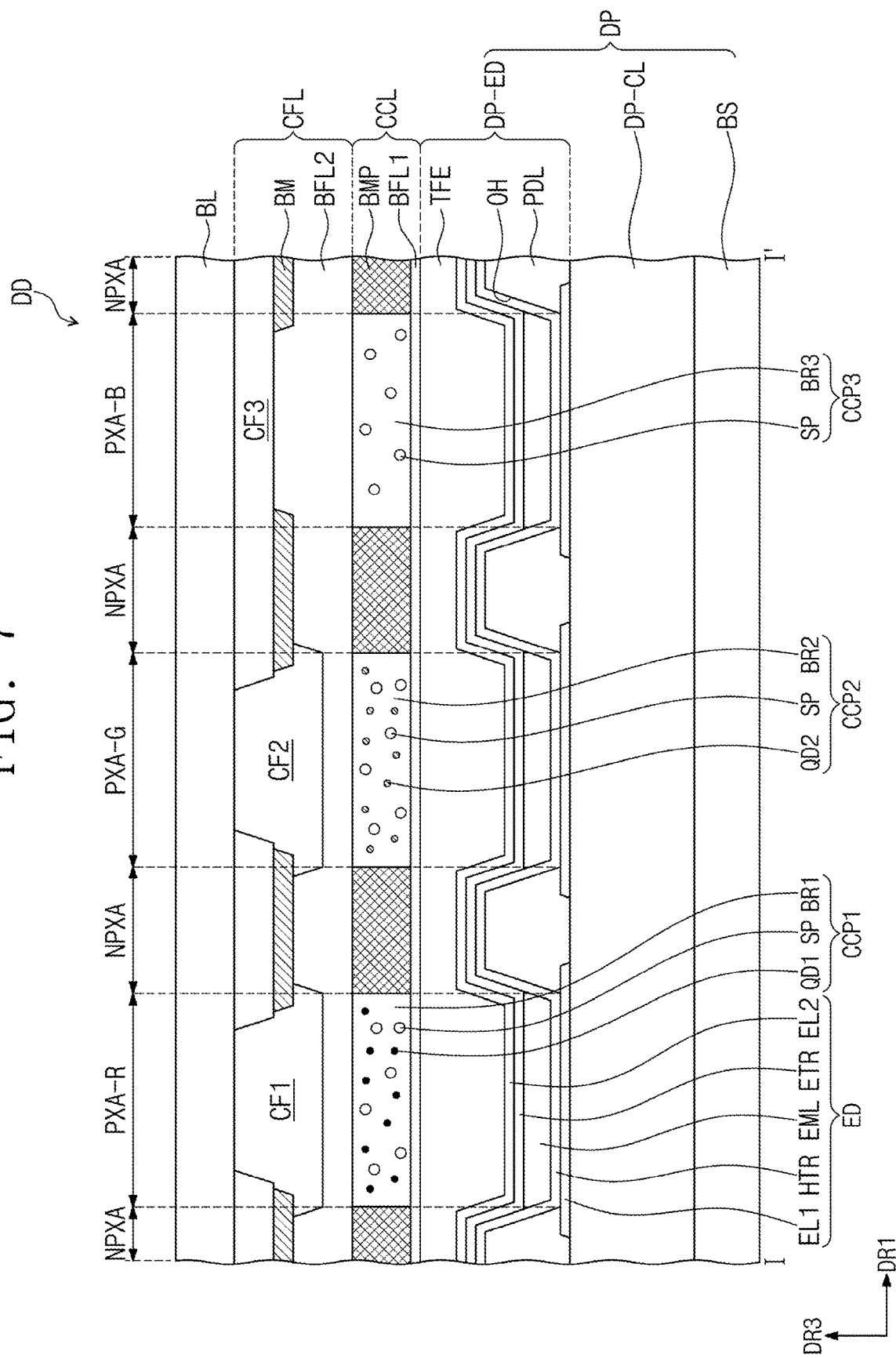
FIG. 7 and FIG. 8 are cross-sectional views of display apparatuses according to embodiments, respectively.
Figure 8:
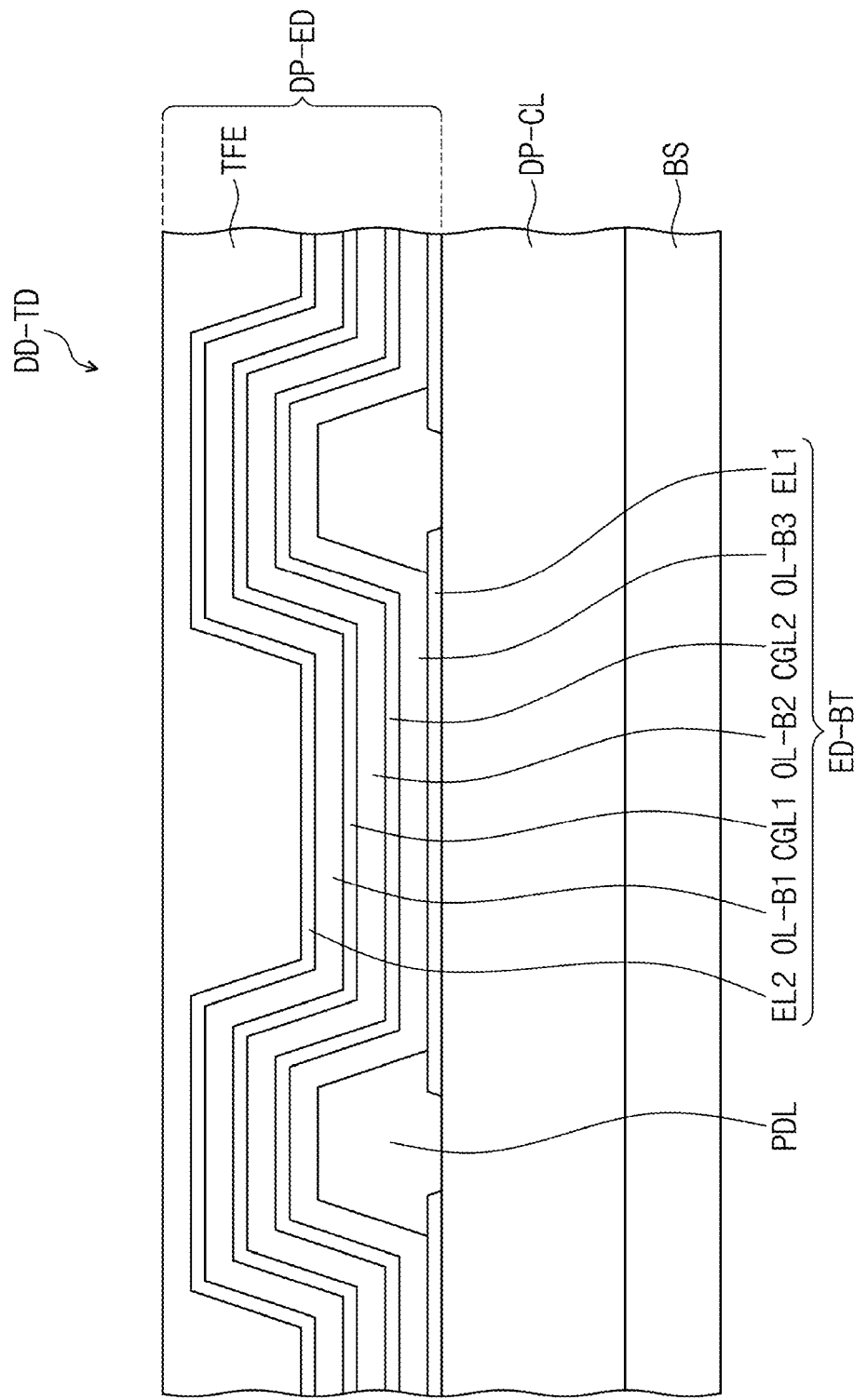

FIG. 7 and FIG. 8 are cross-sectional views on display apparatuses according to embodiments, respectively. In the explanation on the display apparatuses of embodiments referring to FIG. 7 and FIG. 8, the overlapping parts with the explanation on FIG. 1 to FIG. 6 will not be explained again, and the different features will be explained chiefly.

Referring to FIG. 7, the display apparatus DD according to one or more embodiments may include a display panel DP including a display device layer DP-ED, a light controlling layer CCL disposed on the display panel D, and a color filter layer CFL.

In one or more embodiments shown in FIG. 7, the display panel DP includes a base layer BS, a circuit layer DP-CL provided on the base layer BS and a display device layer DP-ED, and the display device layer DP-ED may include an electroluminescence device ED.

The electroluminescence device ED may include a first electrode EL1, a hole transport region HTR disposed on the first electrode EL1, an emission layer EML disposed on the hole transport region HTR, an electron transport region ETR disposed on the emission layer EML, and a second electrode EL2 disposed on the electron transport region ETR. Here, the same structure of the electroluminescence devices ED of FIG. 3 to FIG. 6 may be applied to the structure of the electroluminescence device ED shown in FIG. 7.

Referring to FIG. 7, the emission layer EML may be disposed in an opening part OH defined in a pixel definition layer PDL. For example, the emission layer EML divided by the pixel definition layer PDL and correspondingly provided to each of luminous areas PXA-R, PXA-G and PXA-B may emit light in the same wavelength region. In the display apparatus DD of one or more embodiments, the emission layer EML may emit blue light. In one or more embodiments, the emission layer EML may be provided as a common layer for all luminous areas PXA-R, PXA-G and PXA-B.

The light controlling layer CCL may be disposed on the display panel DP. The light controlling layer CCL may include a light converter. The light converter may be a quantum dot or a phosphor. The light converter may transform the wavelength of light provided thereto and then emit the converted light. For example, the light controlling layer CCL may be a layer including quantum dots or a layer including phosphors.

The light controlling layer CCL may include multiple light controlling parts CCP1, CCP2 and CCP3. The light controlling parts CCP1, CCP2 and CCP3 may be separated from one another.

Referring to FIG. 7, partition pattern BMP may be disposed between the separated light controlling parts CCP1, CCP2 and CCP3, but embodiments of the present disclosure are not limited thereto. In FIG. 7, the partition pattern BMP is shown not to be overlapped with the light controlling parts CCP1, CCP2 and CCP3, but at least a portion of the edge of the light controlling parts CCP1, CCP2 and CCP3 may be overlapped with the partition pattern BMP.

The light controlling layer CCL may include a first light controlling part CCP1 including a first quantum dot QD1 converting (e.g., to convert) first color light provided from the electroluminescence device ED into second color light, a second light controlling part CCP2 including a second quantum dot QD2 converting (e.g., to convert) first color light into third color light, and a third light controlling part CCP3 transmitting (e.g., to transmit) first color light.

In one or more embodiments, the first light controlling part CCP1 may provide red light which is the second color light, and the second light controlling part CCP2 may provide green light which is the third color light. The third color controlling part CCP3 may transmit and provide blue light which is the first color light provided from the electroluminescence device ED. For example, the first quantum dot QD1 may be a red quantum dot, and the second quantum dot QD2 may be a green quantum dot. For the quantum dots QD1 and QD2, the same explanation as above may be applied.

In one or more embodiments, the light controlling layer CCL may further include a scatterer SP. The first light controlling part CCP1 may include the first quantum dot QD1 and the scatterer SP, the second light controlling part CCP2 may include the second quantum dot QD2 and the scatterer SP, and the third light controlling part CCP3 may not include a quantum dot but include the scatterer SP.

The scatterer SP may be an inorganic particle. For example, the scatterer SP may include at least one selected from among $TiO_2$, ZnO, $Al_2O_3$, $SiO_2$, and hollow silica. The scatterer SP may include at least one selected from among $TiO_2$, ZnO, $Al_2O_3$, $SiO_2$, and hollow silica, or may be a mixture of two or more materials selected among $TiO_2$, ZnO, $Al_2O_3$, $SiO_2$, and hollow silica.

Each of the first light controlling part CCP1, the second light controlling part CCP2, and the third light controlling part CCP3 may include base resins BR1, BR2 and BR3 respectively dispersing the quantum dots QD1 and QD2 and the scatterer SP. In one or more embodiments, the first light controlling part CCP1 may include the first quantum dot QD1 and the scatterer SP dispersed in the first base resin BR1, the second light controlling part CCP2 may include the second quantum dot QD2 and the scatterer SP dispersed in the second base resin BR2, and the third light controlling part CCP3 may include the scatterer particle SP dispersed in the third base resin BR3. The base resins BR1, BR2 and BR3 are mediums in which the quantum dots QD1 and QD2 and the scatterer SP are dispersed, and may be composed of various suitable resin compositions which may be generally referred to as a binder. For example, the base resins BR1, BR2 and BR3 may be acrylic resins, urethane-based resins, silicone-based resins, epoxy-based resins, etc. The base resins BR1, BR2 and BR3 may be transparent resins. In one or more embodiments, the first base resin BR1, the second base resin BR2 and the third base resin BR3 may be the same or different from each other.

The light controlling layer CCL may include a barrier layer BFL1. The barrier layer BFL1 may play the role of blocking or reducing the penetration of moisture and/or oxygen (hereinafter, will be referred to as "humidity/oxygen"). The barrier layer BFL1 may be disposed on the light controlling parts CCP1, CCP2 and CCP3 to block or reduce the exposure of the light controlling parts CCP1, CCP2 and CCP3 to humidity/oxygen. In one or more embodiments, the barrier layer BFL1 may cover the light controlling parts CCP1, CCP2 and CCP3. In one or more embodiments, a barrier layer BFL2 may be provided between the light controlling parts CCP1, CCP2 and CCP3 and a color filter layer CFL.

Barrier layers BFL1 and BFL2 may include at least one inorganic layer. For example, the barrier layers BFL1 and BFL2 may be formed by including an inorganic material. For example, the barrier layers BFL1 and BFL2 may each independently be formed by including silicon nitride, aluminum nitride, zirconium nitride, titanium nitride, hafnium nitride, tantalum nitride, silicon oxide, aluminum oxide, titanium oxide, tin oxide, cerium oxide and/or silicon oxynitride, or any suitable metal thin film securing light transmittance. In one or more embodiments, the barrier layers BFL1 and BFL2 may further include an organic layer. The barrier layers BFL1 and BFL2 may be composed of a single layer of multiple layers.

In the display apparatus DD of one or more embodiments, the color filter layer CFL may be disposed (e.g., positioned) on the light controlling layer CCL. For example, the color filter layer CFL may be disposed directly on the light controlling layer CCL. In this case, the barrier layer BFL2 may be omitted.

The color filter layer CFL may include a light blocking part BM and filters CF1, CF2 and CF3. The color filter layer CFL may include a first filter CF1 transmitting (e.g., to transmit) second color light, a second filter CF2 transmitting (e.g., to transmit) third color light, and a third filter CF3 transmitting (e.g., to transmit) first color light. For example, the first filter CF1 may be a red filter, the second filter CF2 may be a green filter, and the third filter CF3 may be a blue filter. Each of the filters CF1, CF2 and CF3 may include a polymer photosensitive resin and a pigment and/or dye. The first filter CF1 may include a red pigment and/or dye, the second filter CF2 may include a green pigment and/or dye, and the third filter CF3 may include a blue pigment and/or dye. However, embodiments of the present disclosure are not limited thereto, and the third filter CF3 may not include the pigment and/or dye. The third filter CF3 may include a polymer photosensitive resin and not include a pigment and/or dye. The third filter CF3 may be transparent. The third filter CF3 may be formed using a transparent photosensitive resin.

In one or more embodiments, the first filter CF1 and the second filter CF2 may be yellow filters. The first filter CF1 and the second filter CF2 may be provided in one body without distinction (e.g., may be formed integrally with each other).

The light blocking part BM may be a black matrix. The light blocking part BM may be formed by including an organic light blocking material or an inorganic light blocking material including a black pigment and/or black dye. The light blocking part BM may prevent or reduce light leakage phenomenon and divide (e.g., define) the boundaries among adjacent filters CF1, CF2 and CF3. In one or more embodiments, the light blocking part BM may be formed as a blue filter.

The first to third filters CF1, CF2 and CF3 may be disposed (e.g., positioned) corresponding to a red luminous area PXA-R, a green luminous area PXA-G, and a blue luminous area PXA-B, respectively.

On the color filter layer CFL, a base substrate BL may be disposed. The base substrate BL may be a member providing a base surface on which the color filter layer CFL, the light controlling layer CCL, etc. are disposed. The base substrate BL may be a glass substrate, a metal substrate, a plastic substrate, etc. However, embodiments of the present disclosure are not limited thereto, and the base substrate BL may be an inorganic layer, an organic layer or a composite material layer. In one or more embodiments, the base substrate BL may be omitted.

FIG. 8 is a cross-sectional view showing a portion of the display apparatus according to one or more embodiments. In FIG. 8, the cross-sectional view of a portion corresponding to the display panel DP in FIG. 7 is shown. In a display apparatus DD-TD of one or more embodiments, an electroluminescence device ED-BT may include multiple light-emitting structures OL-B1, OL-B2 and OL-B3. The electroluminescence device ED-BT may include oppositely disposed first electrode EL1 and second electrode EL2, and the multiple light-emitting structures OL-B1, OL-B2 and OL-B3 stacked in order in a thickness direction and provided between the first electrode EL1 and the second electrode EL2. Each of the light-emitting structures OL-B1, OL-B2 and OL-B3 may include an emission layer EML (FIG. 7), and a hole transport region HTR and an electron transport region ETR disposed with the emission layer EML (FIG. 7) therebetween.

For example, the electroluminescence device ED-BT included in the display apparatus DD-TD of one or more embodiments may be an electroluminescence device of a tandem structure including multiple emission layers.

In one or more embodiments shown in FIG. 8, light emitted from the light-emitting structures OL-B1, OL-B2 and OL-B3 may be all blue light. However, embodiments of the present disclosure are not limited thereto, and the wavelength regions of light emitted from the light-emitting structures OL-B1, OL-B2 and OL-B3 may be different from each other. For example, the electroluminescence device ED-BT including the multiple light-emitting structures OL-B1, OL-B2 and OL-B3 emitting (e.g., to emit) light in different wavelength regions may emit white light.

Among neighboring light-emitting structures OL-B1, OL-B2 and OL-B3, a charge generating layer CGL may be disposed (e.g., a first charge generating layer CGL1 may be between the light-emitting structures OL-B1 and OL-B2, and a second charge generating layer CGL2 may be between the light-emitting structures OL-B2 and OL-B3). The charge generating layer CGL may include a p-type charge generating layer and/or an n-type charge generating layer.

The electroluminescence device ED according to one or more embodiments of the present disclosure includes the polycyclic compound of one or more embodiments in an emission layer EML disposed between a first electrode EL1 and a second electrode EL2 and may show excellent emission efficiency.

Meanwhile, the compound of one or more embodiments may be included in an organic layer other than the emission layer EML as a material for an electroluminescence device ED. For example, the electroluminescence device ED according to one or more embodiments of the present disclosure may include the fused polycyclic compound in at least one functional layer disposed between the first electrode EL1 and the second electrode EL2, and/or a capping layer CPL disposed on the second electrode EL2.

The electroluminescence device of one or more embodiments, including the polycyclic compound of one or more embodiments in an emission layer may emit blue light and show high efficiency properties.

Hereinafter, the polycyclic compound according to one or more embodiments and the present disclosure and the electroluminescence device of one or more embodiments will be explained referring to embodiments and comparative embodiments. However, the embodiments shown below are only illustrations to assist the understanding of the present disclosure, and the scope of the present disclosure is not limited thereto.

Synthetic Method of Polycyclic Compound According to an Embodiment

The synthetic method of the polycyclic compound according to one or more embodiments of the present disclosure will be explained by referring to the synthetic methods of Compounds 1, 2, 4, 6, 8, 13, 15, 16, 21 and 37. However, the synthetic method of the polycyclic compound explained below is only one or more embodiments, and the synthetic method of the polycyclic compound according to the present disclosure is not limited to the following examples.

1. Synthesis of Compound 1

Compound 1 of one or more embodiments may be synthesized by Reaction 1 below.

1-1. Synthesis of Compound 1

2 g of 3-bromo-9-phenyl-9H-carbazole (CAS=1153-85-1), 2.53 g of 3-(9-phenyl-9H-fluoren-9-yl)-9H-carbazole (CAS=1310827-55-4), 1.19 g of sodium tert-butoxide, 0.28 g of tris(dibenzylideneacetone)dipalladium(0) (Pd$_2$(dba)$_3$), and 0.13 mL of tri-tert-butylphosphine (t-Bu$_3$P) were dissolved in 30 mL of a toluene solvent and then, stirred at about 110 degrees (° C.) for about 12 hours. After finishing the reaction, the reaction solution was extracted, and the organic layer thus obtained was dried. The residue was separated by column chromatography, recrystalized and purified by sublimation to obtain 3 g (yield 75%) of Compound 1 with high purity. Compound 1 was identified by LC-MS (Liquid chromatography-mass spectrometry) and 1H-NMR (nuclear magnetic resonance). The values are recorded in Table 1 below.

2. Synthesis of Compound 2

Compound 2 of one or more embodiments may be synthesized by Reaction 2 below.

Reaction 2

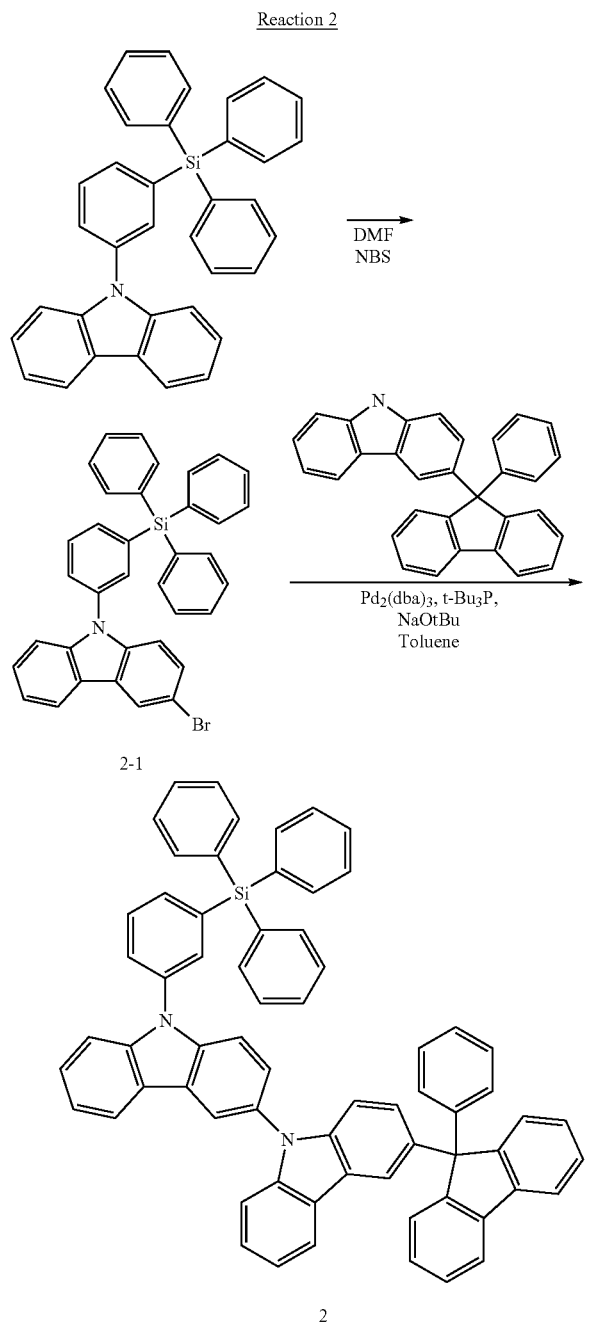

2

2-1. Synthesis of Intermediate Compound 2-1

10 g of 9-(3-(triphenylsilyl)phenyl)-9H-carbazole (CAS=944465-44-5) was dissolved in a DMF solvent, and at about 0 degrees, 3.55 g of NBS was added thereto dropwisely, followed by stirring at room temperature for about 12 hours. After finishing the reaction, the reaction solution was extracted, and the organic layer thus obtained was dried. The residue was separated by column chromatography to obtain 10 g (yield 86%) of Intermediate Compound 2-1. Intermediate Compound 2-1 was identified by LC-MS. (C36H26BrNSi: M+1 580.6)

2-2. Synthesis of Compound 2

2 g of Intermediate Compound 2-1, 1.4 g of 3-(9-phenyl-9H-fluoren-9-yl)-9H-carbazole (CAS=1310827-55-4), 0.66 g of sodium tert-butoxide, 0.15 g of $Pd_2(dba)_3$, and 0.07 mL of $t-Bu_3P$ were dissolved in 30 mL of a toluene solvent and then, stirred at about 110 degrees for about 12 hours. After finishing the reaction, the reaction solution was extracted, and the organic layer thus obtained was dried. The residue was separated by column chromatography, recrystalized and purified by sublimation to obtain 2.8 g (yield 90%) of Compound 2 with high purity. Compound 2 was identified by LC-MS and 1H-NMR. The values are recorded in Table 1 below.

3. Synthesis of Compound 4

Compound 4 of one or more embodiments may be synthesized by Reaction 3 below.

Reaction 3

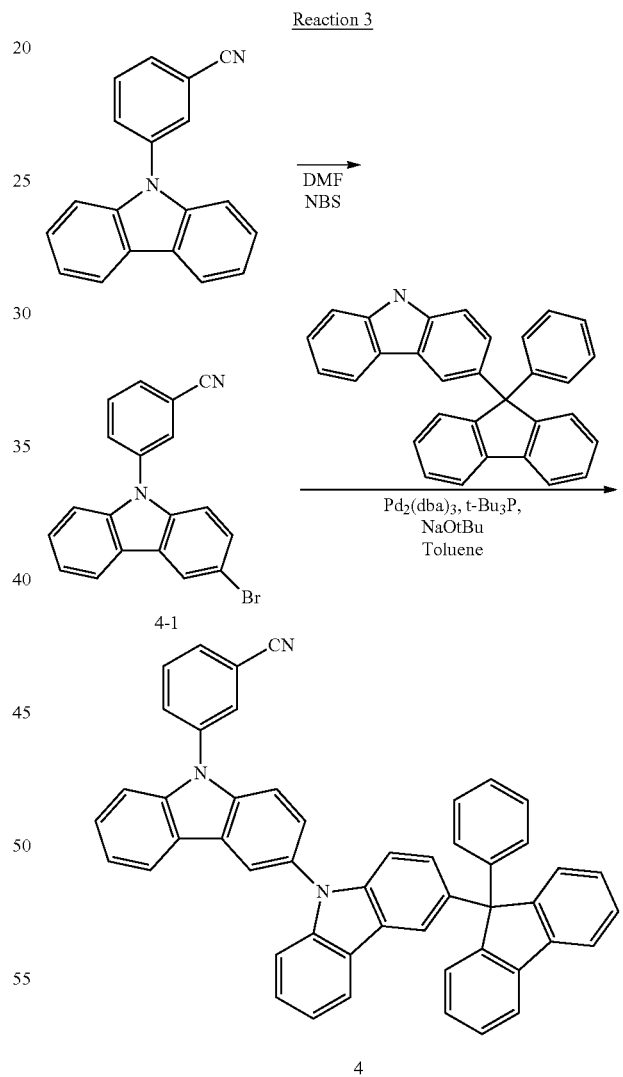

4

3-1. Synthesis of Intermediate Compound 4-1

10 g of 3-(9H-carbazole-9-yl)benzonitrile (CAS=1097244-73-9) was dissolved in a DMF solvent, and at about 0 degrees, 6.63 g of NBS was added thereto dropwisely, followed by stirring at room temperature for about 12 hours. After finishing the reaction, the reaction solution was extracted, and the organic layer thus obtained was dried. The residue was separated by column chromatography to obtain 11 g (yield 85%) of Intermediate Compound 4-1. Intermediate Compound 4-1 was identified by LC-MS. (C19H11BrN2: M+1 474.4)

3-2. Synthesis of Compound 4

2 g of Intermediate Compound 4-1, 2.35 g of 3-(9-phenyl-9H-fluoren-9-yl)-9H-carbazole (CAS=1310827-55-4), 1.11 g of sodium tert-butoxide, 0.26 g of $Pd_2(dba)_3$, and 0.12 mL of $t\text{-}Bu_3P$ were dissolved in 30 mL of a toluene solvent and then, stirred at about 110 degrees for about 12 hours. After finishing the reaction, the reaction solution was extracted, and the organic layer thus obtained was dried. The residue was separated by column chromatography, recrystalized and purified by sublimation to obtain 3 g (yield 77%) of Compound 4 with high purity. Compound 4 was identified by LC-MS and 1H-NMR. The values are recorded in Table 1 below.

4. Synthesis of Compound 5

Compound 5 of one or more embodiments may be synthesized by Reaction 4 below.

4-1. Synthesis of Compound 5

2 g of 3-bromo-9-(dibenzo[b,d]furan-2-yl)-9H-carbazole (CAS=1338488-90-6), 1.98 g of 3-(9-phenyl-9H-fluoren-9-yl)-9H-carbazole (CAS=1310827-55-4), 0.93 g of sodium tert-butoxide, 0.22 g of $Pd_2(dba)_3$, and 0.11 mL of $t\text{-}Bu_3P$ were dissolved in 30 mL of a toluene solvent and then, stirred at about 110 degrees for about 12 hours. After finishing the reaction, the reaction solution was extracted, and the organic layer thus obtained was dried. The residue was separated by column chromatography, recrystalized and purified by sublimation to obtain 2.7 g (yield 75%) of Compound 5 with high purity. Compound 5 was identified by LC-MS and 1H-NMR. The values are recorded in Table 1 below.

Reaction 4

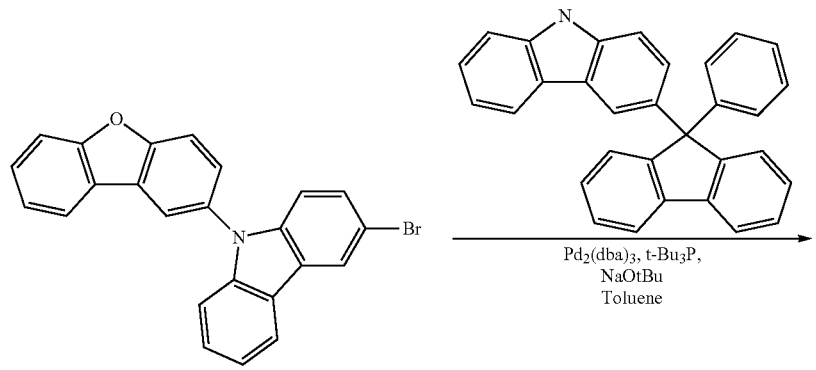

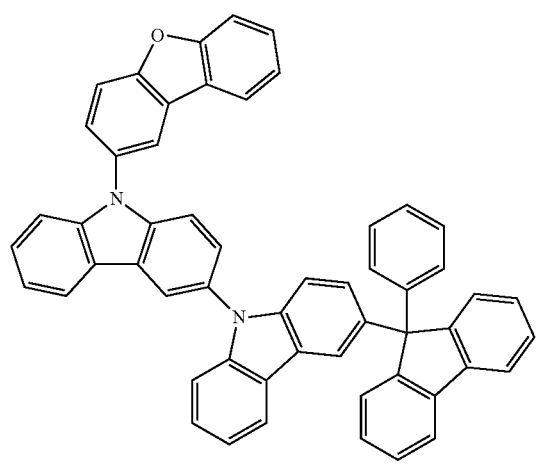

5. Synthesis of Compound 8

Compound 8 of one or more embodiments may be synthesized by Reaction 5 below.

Reaction 5

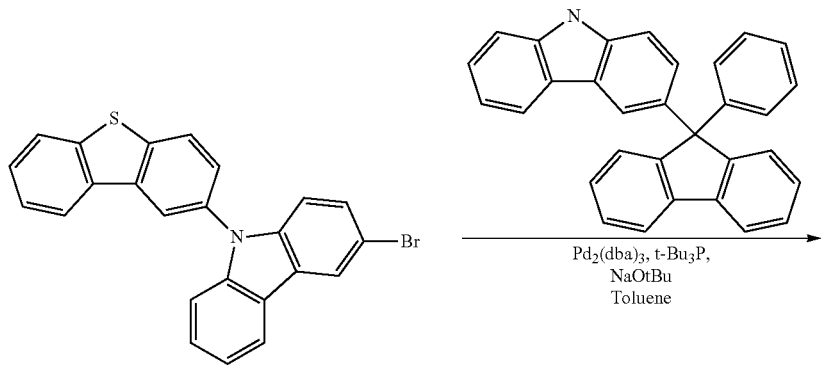

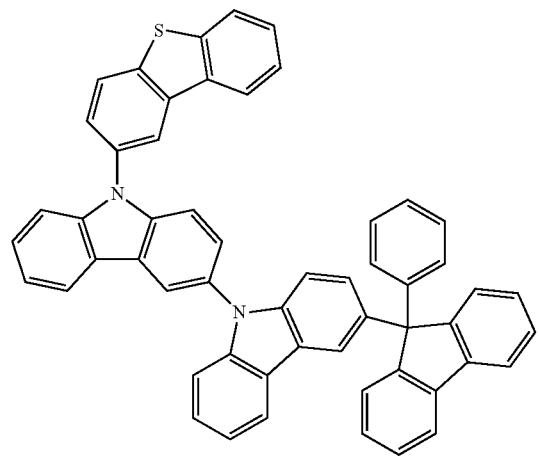

8

5-1. Synthesis of Compound 8

2 g of 3-bromo-9-(dibenzo[b,d]thiophene-2-yl)-9H-carbazole (CAS=1402543-33-2), 1.9 g of 3-(9-phenyl-9H-fluoren-9-yl)-9H-carbazole (CAS=1310827-55-4), 0.9 g of sodium tert-butoxide, 0.21 g of Pd$_2$(dba)$_3$, and 0.1 mL of t-Bu$_3$P were dissolved in 30 mL of a toluene solvent and then, stirred at about 110 degrees for about 12 hours. After finishing the reaction, the reaction solution was extracted, and the organic layer thus obtained was dried. The residue was separated by column chromatography, recrystalized and purified by sublimation to obtain 3.1 g (yield 88%) of Compound 8 with high purity. Compound 8 was identified by LC-MS and 1H-NMR. The values are recorded in Table 1 below.

6. Synthesis of Compound 13

Compound 13 of one or more embodiments may be synthesized by Reaction 6 below.

Reaction 6

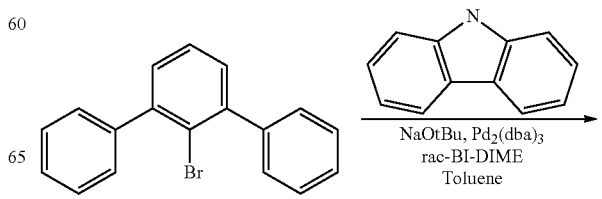

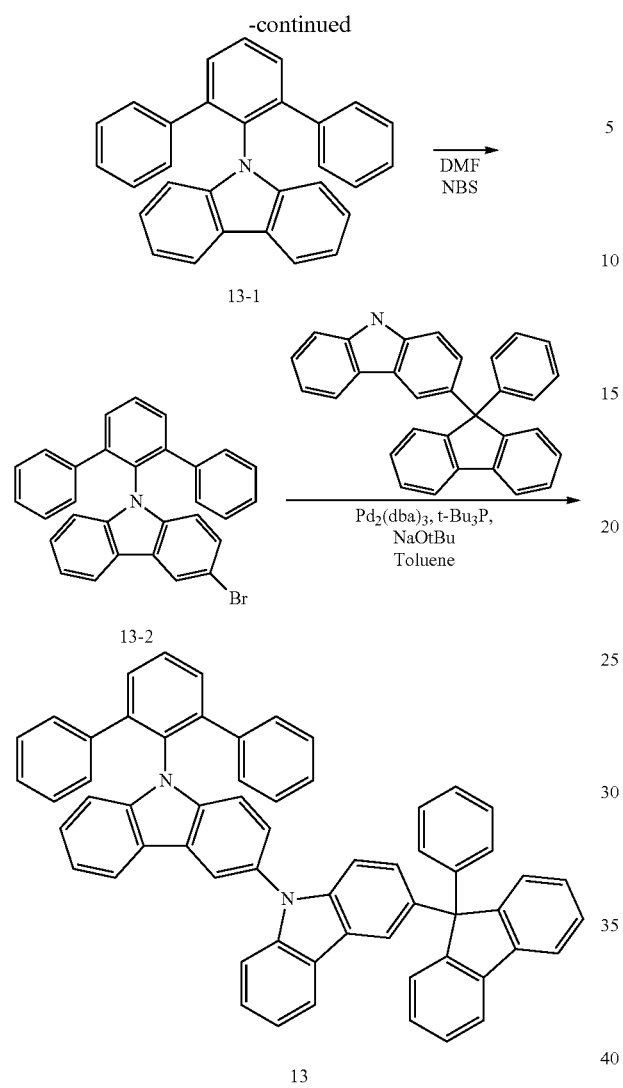

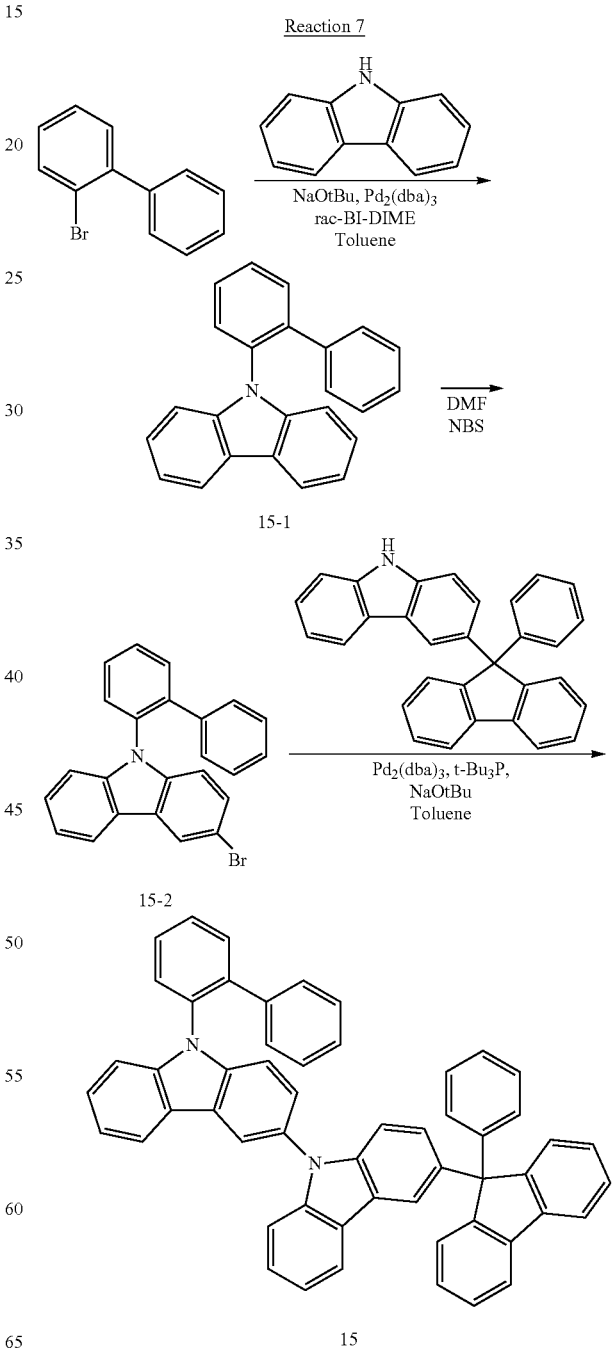

6-1. Synthesis of Intermediate Compound 13-1

10 g of 2'-bromo-1,1':3',1''-terphenyl (CAS=126866-29-3), 5.41 g of carbazole, 6.22 g of sodium tert-butoxide, 1.48 g of Pd$_2$(dba)$_3$, and 1.07 g of rac-BI-DIME (CAS=1246888-90-3) were dissolved in 30 mL of a toluene solvent and then, stirred at about 110 degrees for about 12 hours. After finishing the reaction, the reaction solution was extracted, and the organic layer thus obtained was dried. The residue was separated by column chromatography and purified by sublimation to obtain 10 g (yield 78%) of Intermediate Compound 13-1. Intermediate Compound 13-1 was identified by LC-MS. (C30H21N: M+1 395.51)

6-2. Synthesis of Intermediate Compound 13-2

10 g of Intermediate Compound 13-1 was dissolved in a DMF solvent, and at about 0 degrees, 4.5 g of NBS was added thereto dropwisely, followed by stirring at room temperature for about 12 hours. After finishing the reaction, the reaction solution was extracted, and the organic layer thus obtained was dried. The residue was separated by column chromatography to obtain 11 g (yield 92%) of Intermediate Compound 13-2. Intermediate Compound 13-2 was identified by LC-MS. (C30H20BrN: M+1 474.4)

6-3. Synthesis of Compound 13

2 g of Intermediate Compound 13-2, 1.72 g of 3-(9-phenyl-9H-fluoren-9-yl)-9H-carbazole (CAS=1310827-55-4), 0.81 g of sodium tert-butoxide, 0.19 g of Pd$_2$(dba)$_3$, and 0.08 mL of t-Bu$_3$P were dissolved in 30 mL of a toluene solvent and then, stirred at about 110 degrees for about 12 hours. After finishing the reaction, the reaction solution was extracted, and the organic layer thus obtained was dried. The residue was separated by column chromatography, recrystalized and purified by sublimation to obtain 2.4 g (yield 71%) of Compound 13 with high purity. Compound 13 was identified by LC-MS and 1H-NMR. The values are recorded in Table 1 below.

7. Synthesis of Compound 15

Compound 15 of one or more embodiments may be synthesized by Reaction 7 below.

Reaction 7

7-1. Synthesis of Intermediate Compound 15-1

10 g of 2-bromo-1,1'-biphenyl (CAS=2052-07-5), 7.17 g of carbazole, 8.25 g of sodium tert-butoxide, 1.96 g of $Pd_2(dba)_3$, and 1.42 g of rac-BI-DIME (CAS=1246888-90-3) were dissolved in 200 mL of a toluene solvent and then, stirred at about 110° C. for about 12 hours. After finishing the reaction, the reaction solution was extracted, and the organic layer thus obtained was dried. The residue was separated by column chromatography and purified by sublimation to obtain 10 g (yield 73%) of Intermediate Compound 15-1. Intermediate Compound 15-1 was identified by LC-MS. (C24H17N: M+1 320.41)

7-2. Synthesis of Intermediate Compound 15-2

10 g of Intermediate Compound 15-1 was dissolved in 150 mL of DMF, and at about 0° C., 5.57 g of NBS was added thereto dropwisely, followed by stirring at room temperature for about 12 hours. After finishing the reaction, the reaction solution was extracted, and the organic layer thus obtained was dried. The residue was separated by column chromatography to obtain 12 g (yield 96%) of Intermediate Compound 15-2. Intermediate Compound 15-2 was identified by LC-MS. (C24H16BrN: M+1 398.3)

7-3. Synthesis of Compound 15

2 g of Intermediate Compound 15-2, 2.05 g of 3-(9-phenyl-9H-fluoren-9-yl)-9H-carbazole (CAS=1310827-55-4), 0.97 g of sodium tert-butoxide, 0.23 g of $Pd_2(dba)_3$, and 0.16 mL of $t-Bu_3P$ were dissolved in 30 mL of a toluene solvent and then, stirred at about 110° C. for about 12 hours. After finishing the reaction, the reaction solution was extracted, and the organic layer thus obtained was dried. The residue was separated by column chromatography, recrystalized and purified by sublimation to obtain 3 g (yield 82%) of Compound 15 with high purity. Compound 15 was identified by LC-MS and 1H-NMR. The values are recorded in Table 1 below.

8. Synthesis of Compound 16

Compound 16 of one or more embodiments may be synthesized by Reaction 8 below.

Reaction 8

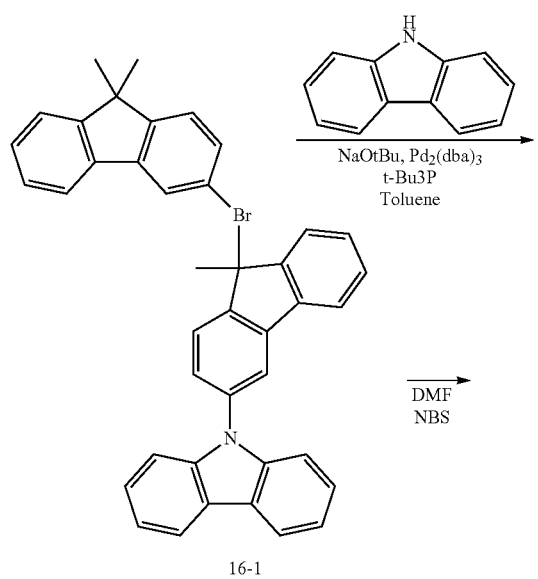

16-1

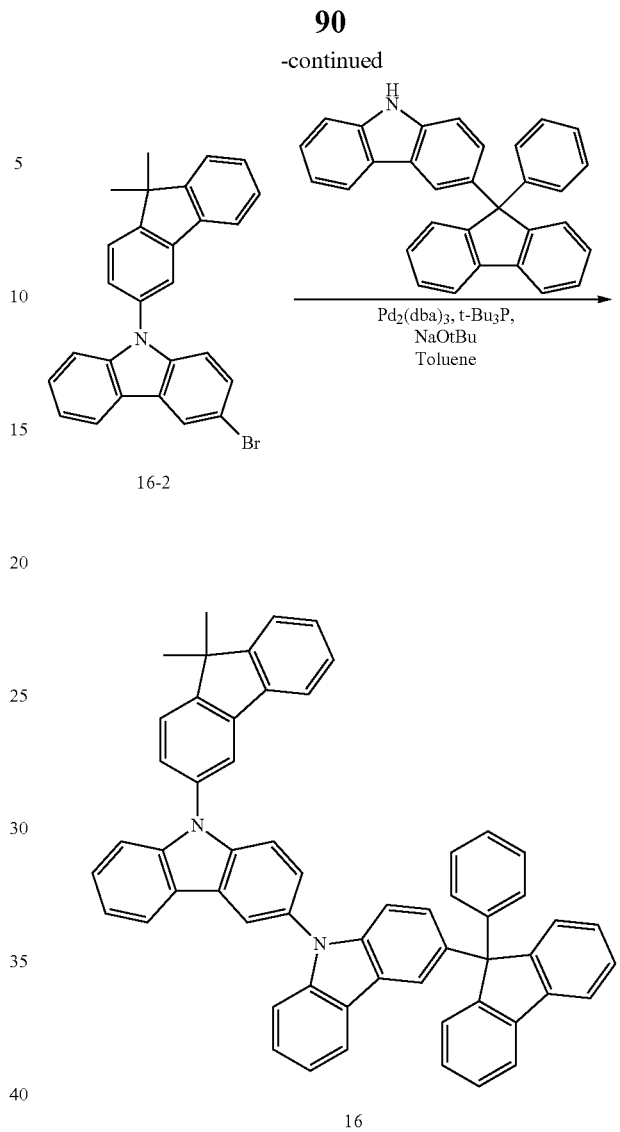

16-2

16

8-1. Synthesis of Intermediate Compound 16-1

10 g of 3-bromo-9,9-dimethyl-9H-fluorene (CAS=1190360-23-6), 6.12 g of carbazole, 7.04 g of sodium tert-butoxide, 1.68 g of $Pd_2(dba)_3$, and 1.21 mL of $t-Bu_3P$ were dissolved in 180 mL of a toluene solvent and then, stirred at about 110° C. for about 12 hours. After finishing the reaction, the reaction solution was extracted, and the organic layer thus obtained was dried. The residue was separated by column chromatography and purified by sublimation to obtain 11 g (yield 84%) of Intermediate Compound 16-1. Intermediate Compound 16-1 was identified by LC-MS. (C27H21N: M+1 359.47)

8-2. Synthesis of Intermediate Compound 16-2

11 g of Intermediate Compound 16-1 was dissolved in 150 mL of DMF, and at about 0° C., 5.45 g of NBS was added thereto dropwisely, followed by stirring at room temperature for about 12 hours. After finishing the reaction, the reaction solution was extracted, and the organic layer thus obtained was dried. The residue was separated by column chromatography to obtain 13 g (yield 97%) of Intermediate Compound 16-2. Intermediate Compound 16-2 was identified by LC-MS. (C27H20BrN: M+1 438.37)

8-3. Synthesis of Compound 16

2 g of Intermediate Compound 16-2, 1.86 g of 3-(9-phenyl-9H-fluoren-9-yl)-9H-carbazole (CAS=1310827-55-4), 0.88 g of sodium tert-butoxide, 0.21 g of Pd$_2$(dba)$_3$, and 0.15 mL of t-Bu$_3$P were dissolved in 30 mL of a toluene solvent and then, stirred at about 110° C. for about 12 hours. After finishing the reaction, the reaction solution was extracted, and the organic layer thus obtained was dried. The residue was separated by column chromatography, recrystalized and purified by sublimation to obtain 3 g (yield 86%) of Compound 16 with high purity. Compound 16 was identified by LC-MS and 1H-NMR. The values are recorded in Table 1 below.

9. Synthesis of Compound 21

Compound 21 of one or more embodiments may be synthesized by Reaction 9 below.

Reaction 9

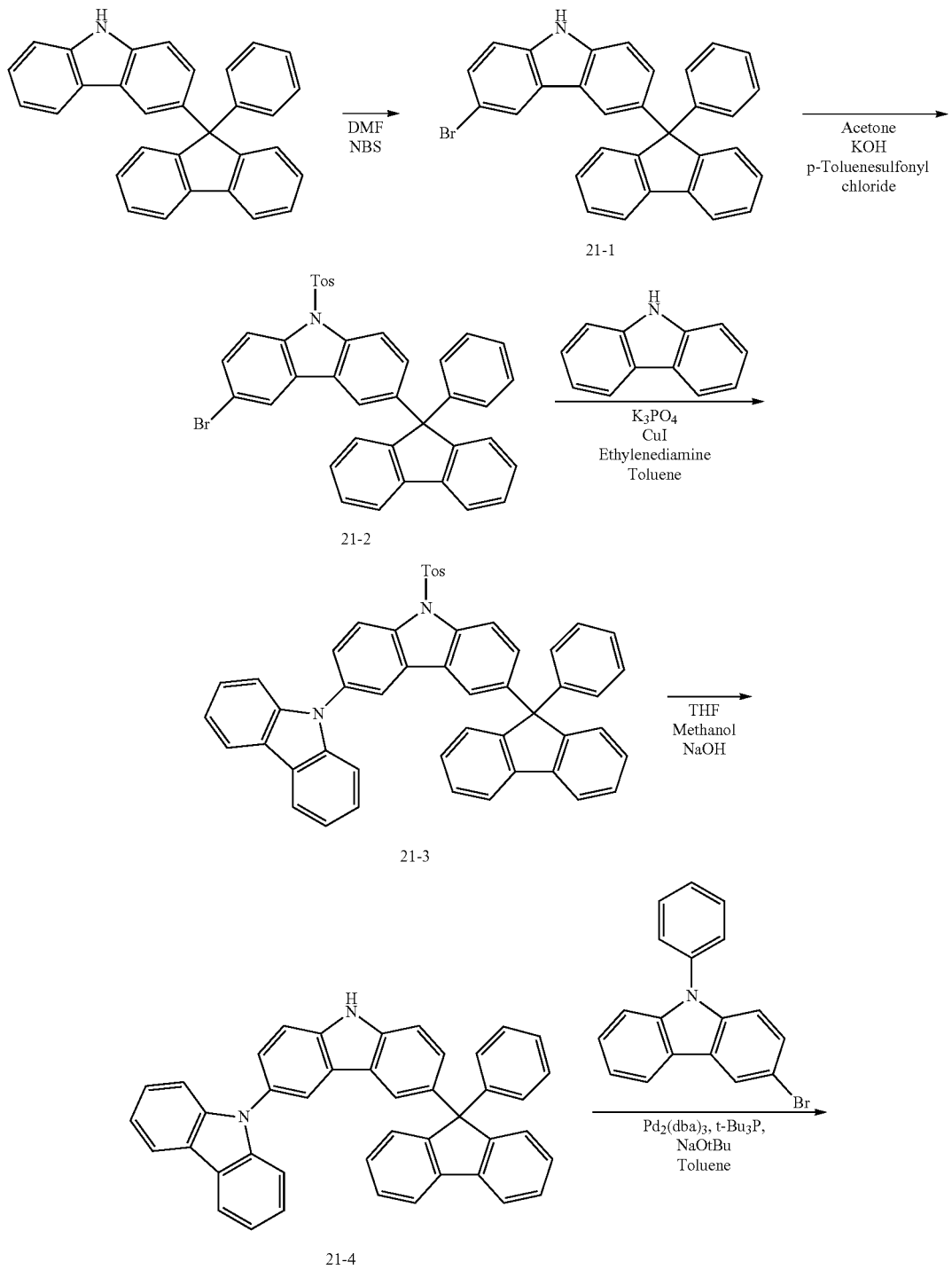

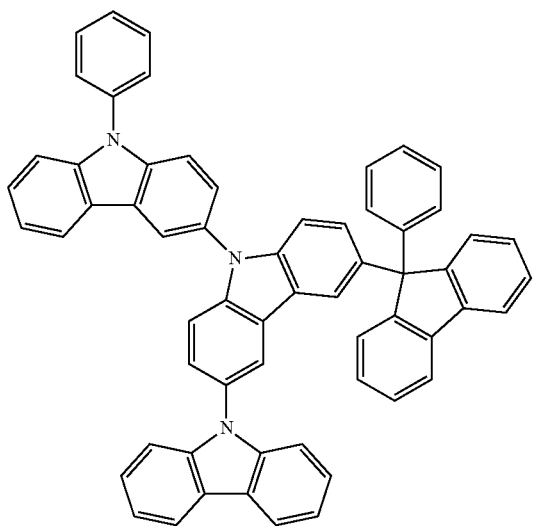

21

9-1. Synthesis of Intermediate Compound 16-1

10 g of 3-(9-phenyl-9H-fluoren-9-yl)-9H-carbazole (CAS=1310827-55-4) was dissolved in 120 mL of DMF, and at about 0° C., 4.37 g of NBS was added thereto dropwisely, followed by stirring at room temperature for about 12 hours. After finishing the reaction, the reaction solution was extracted, and the organic layer thus obtained was dried. The residue was separated by column chromatography to obtain 11.5 g (yield 96%) of Intermediate Compound 21-1. Intermediate Compound 21-1 was identified by LC-MS. (C31H20BrN: M+1 486.41)

9-2. Synthesis of Intermediate Compound 21-2

11.5 g of Intermediate Compound 21-1 was dissolved in an acetone solvent, and 6.76 g of p-toluenesulfonyl chloride and 2.66 g of KOH were added thereto, followed by stirring at about 60° C. for about 6 hours. After finishing the reaction, the reaction solution was extracted, and the organic layer thus obtained was dried. The residue was separated by column chromatography to obtain 13 g (yield 86%) of Intermediate Compound 21-2. Intermediate Compound 21-2 was identified by LC-MS. (C38H26BrNO2S: M+1 640.6)

9-3. Synthesis of Intermediate Compound 21-3

13 g of Intermediate Compound 21-2, 4.03 g of carbazole, 12.8 g of K3PO4, 7.66 g of CuI, and 0.67 mL of ethylenediamine were added and stirred in 100 mL of a toluene solvent for about 12 hours. After finishing the reaction, the reaction solution was extracted, and the organic layer thus obtained was dried. The residue was separated by column chromatography to obtain 12 g (yield 82%) of Intermediate Compound 21-3. Intermediate Compound 21-3 was identified by LC-MS. (C50H34N2O2S: M+1 726.89)

9-4. Synthesis of Intermediate Compound 21-4

12 g of Intermediate Compound 21-3 was dissolved in 80 mL of THF, 40 mL of methanol and 40 mL of deionized water, and 6.6 g of NaOH was added thereto, followed by stirring at about 90° C. for about 12 hours. After finishing the reaction, the reaction solution was extracted, and the organic layer thus obtained was dried. The residue was separated by column chromatography to obtain 7 g (yield 74%) of Intermediate Compound 21-4. Intermediate Compound 21-4 was identified by LC-MS. (C43H28N2: M+1 572.71)

9-5. Synthesis of Compound 21

2 g of Intermediate Compound 21-4, 1.13 g of 3-bromo-9-phenyl-9H-carbazole (CAS=1153-85-1), 0.67 g of sodium tert-butoxide, 0.16 g of Pd2(dba)3, and 0.11 mL of t-Bu3P were dissolved in 20 mL of a toluene solvent and then, stirred at about 110° C. for about 12 hours. After finishing the reaction, the reaction solution was extracted, and the organic layer thus obtained was dried. The residue was separated by column chromatography, recrystalized and purified by sublimation to obtain 2 g (yield 70%) of Compound 21 with high purity. Compound 21 was identified by LC-MS and 1H-NMR. The values are recorded in Table 1 below.

10. Synthesis of Compound 37

Compound 37 of one or more embodiments may be synthesized by Reaction 10 below.

Reaction 10

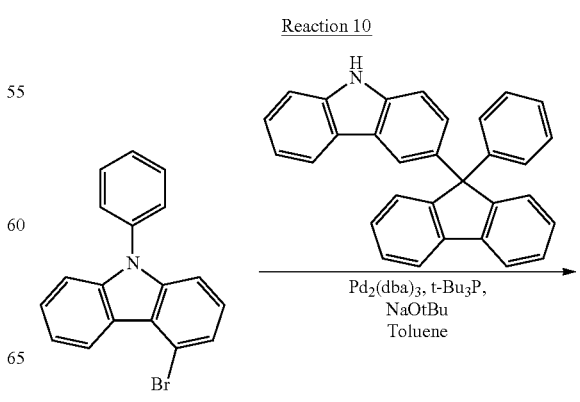

-continued

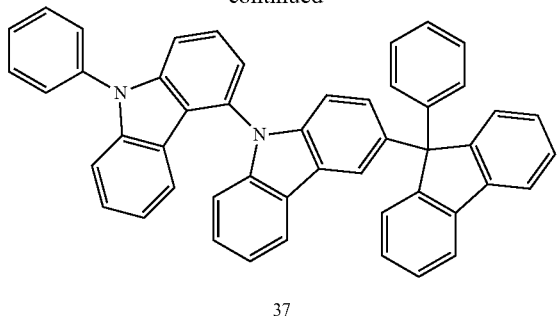

37

10-1. Synthesis of Compound 37

2 g of 4-bromo-9-phenyl-9H-carbazole (CAS=1097884-37-1), 2.53 g of 3-(9-phenyl-9H-fluoren-9-yl)-9H-carbazole (CAS=1310827-55-4), 1.19 g of sodium tert-butoxide, 0.28 g of $Pd_2(dba)_3$, and 0.2 mL of $t\text{-}Bu_3P$ were dissolved in 30 mL of a toluene solvent and then, stirred at about 110° C. for about 12 hours. After finishing the reaction, the reaction solution was extracted, and the organic layer thus obtained was dried. The residue was separated by column chromatography, recrystalized and purified by sublimation to obtain 3 g (yield 75%) of Compound 37 with high purity. Compound 37 was identified by LC-MS and 1H-NMR. The values are recorded in Table 1 below.

The molecular weights and NMR analysis results of Compounds 1, 2, 4, 5, 8, 13, 15, 16, 21, and 37 thus synthesized are shown in Table 1 below.

and washed with ultrasonic waves using isopropyl alcohol and pure water for about 5 minutes, respectively, exposed to ultraviolet rays for about 30 minutes and washed by exposing to ozone. Then, the glass substrate thus washed was installed in a vacuum deposition apparatus. On the substrate a known compound NPD was vacuum deposited to a thickness of about 300 Å to form a hole injection layer, and TCTA was vacuum deposited as a hole transport compound to a thickness of about 200 Å to form a hole transport layer. On the hole transport layer, CzSi was vacuum deposited as a hole transport layer compound to a thickness of about 100 Å.

Then, as a host material during forming an emission layer, the polycyclic compound of one or more embodiments (e.g., one of Compounds 1, 2, 4, 5, 8, 13, 15, 16, 21, and 37) or Comparative Compound was used. As a dopant material, $Ir(pmp)_3$ was used. The host and dopant were co-deposited in a weight ratio of 92:8 to form an emission layer with a thickness of about 250 Å. For example, in Example 1 to Example 10, each of Compounds 1, 2, 4, 5, 8, 13, 15, 16, 21, and 37 was mixed with $Ir(pmp)_3$ and deposited, and in Comparative Example 1 to Comparative Example 4, each of Comparative Compounds C1, C2, C3 and C4 was mixed with $Ir(pmp)_3$ and deposited to form the emission layer.

Then, on the emission layer, TSPO1 was deposited to a thickness of about 200 Å as an electron transport layer compound, and TPBI was deposited to a thickness of about 300 Å as an electron injection layer compound. On the electron transport layer, an alkali metal halide, LiF was deposited to a thickness of about 10 Å as an electron injection layer, and Al was vacuum deposited to a thickness

TABLE 1

| Division | Compound | 1H NMR (CDCl$_3$, 400 MHz) | MS/FAB found | MS/FAB calc. |
|---|---|---|---|---|
| 1 | Compound 1 | 8.55 (d, 2H), 8.05 (s, 1H), 7.90-7.94 (m, 4H), 7.16-7.72 (m, 18H) | 648.81 | 648.26 |
| 2 | Compound 2 | 8.55 (d, 2H), 8.05 (s, 1H), 7.90-7.94 (m, 4H), 7.72 (1H, d), 7.67 (s, 2H), 7.60 (m, 2H), 7.16-7.55 (m, 34H) | 907.20 | 906.34 |
| 3 | Compound 4 | 8.55 (d, 2H), 8.05 (s, 1H), 7.88-7.94 (m, 5H), 7.55-7.72 (m, 8H), 7.16-7.50 (m, 15H) | 673.82 | 673.25 |
| 4 | Compound 5 | 8.55 (d, 2H), 8.05 (s, 1H), 7.90-7.98 (m, 5H), 7.54-7.74 (m, 8H), 7.18-7.45 (m, 20H) | 738.89 | 738.27 |
| 5 | Compound 8 | 8.55 (d, 2H), 8.45 (d, 1H), 8.10 (d, 2H), 7.90-7.94 (m, 6H), 7.67-7.72 (d, 2H), 7.16-7.56 (m, 21H) | 754.95 | 754.24 |
| 6 | Compound 13 | 8.55 (d, 2H), 8.01 (d, 3H), 7.67-7.72 (m, 3H), 7.55 (m, 3H), 7.19-7.55 (m, 29H) | 800.32 | 800.32 |
| 7 | Compound 15 | 8.55 (d, 2H), 8.05 (s, 1H), 7.90-7.94 (m, 4H), 7.80 (t, 1H), 7.72 (d, 1H), 7.67 (s, 1H), 7.55-7.57 (m, 3H), 7.16-7.55 (m, 23H) | 724.91 | 724.29 |
| 8 | Compound 16 | 8.55 (d, 2H), 8.05 (s, 1H), 7.90-7.96 (m, 3H), 7.69-7.72 (m, 3H), 7.55 (m, 3H), 7.16-7.55 (m, 22H), 1.69 (s, 6H) | 764.97 | 764.32 |
| 9 | Compound 21 | 8.82 (s, 1H), 8.55 (d, 2H), 8.19 (d, 1H), 7.90-7.94 (m, 5H), 7.55-7.72 (m, 10H), 7.16-7.38 (m, 18H), 7.18 (d, 1H) | 814 | 813.31 |
| 10 | Compound 37 | 8.55 (d, 1H), 8.05 (s, 1H), 7.90-7.94 (dd, 4H), 7.16-7.62 (m, 26H) | 648.81 | 648.26 |

Manufacture of Electroluminescence Device

An ITO glass substrate with 15 Ω/cm$^2$ (about 1,200 Å) of Corning Co. was cut into a size of 50 mm×50 mm×0.7 mm of about 3,000 Å (cathode electrode) to form a LiF/Al electrode. An electroluminescence device was thus manufactured.

Compounds used in Example 1 to Example 10 and Comparative Example 1 to Comparative Example 4 are shown in Table 2 below.
TABLE 2
Compound 1
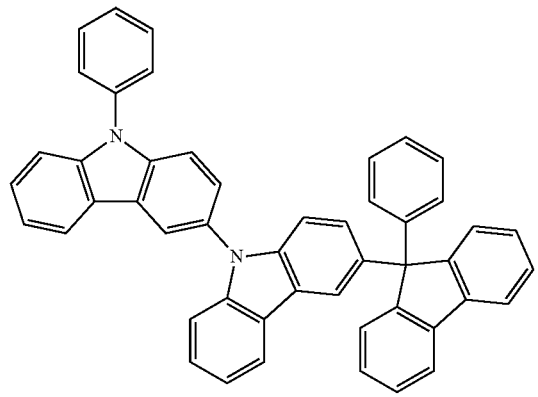 [SMILES: c1ccc(-n2c3ccccc3c3cc(-n4c5ccccc5c5cc(C6(c7ccccc7)c7ccccc7-c7ccccc76)ccc54)ccc32)cc1]
1
Compound 2
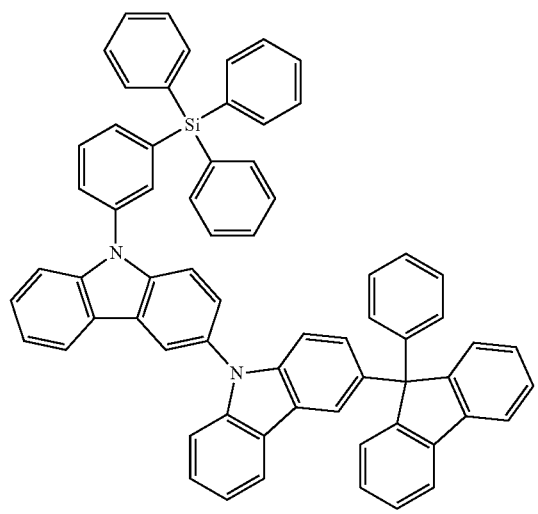 [SMILES: c1ccc(C2(c3ccc4c(c3)c3ccccc3n4-c3ccc4c(c3)c3ccccc3n4-c3cccc([Si](c4ccccc4)(c4ccccc4)c4ccccc4)c3)c3ccccc3-c3ccccc32)cc1]
2
Compound 4
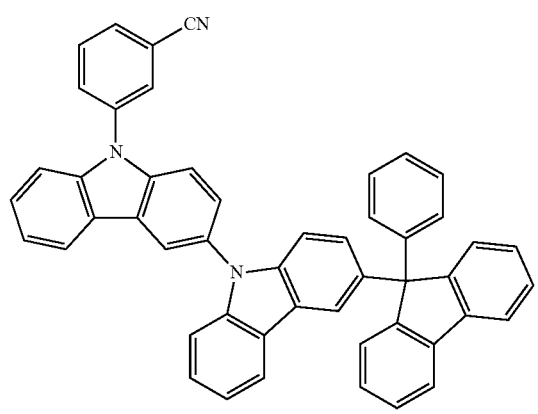 [SMILES: N#Cc1cccc(-n2c3ccccc3c3cc(-n4c5ccccc5c5cc(C6(c7ccccc7)c7ccccc7-c7ccccc76)ccc54)ccc32)c1]
4

TABLE 2-continued
Compound 5
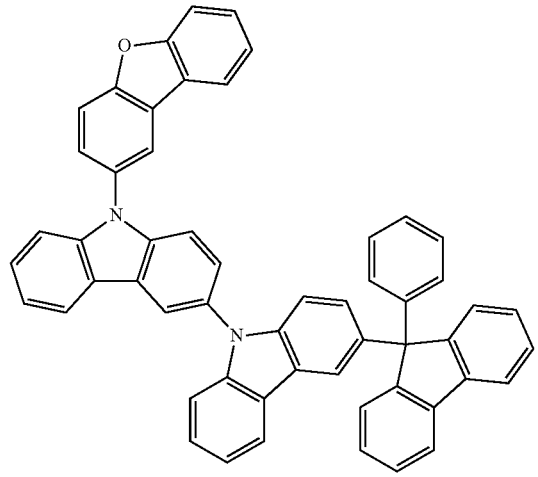
5
Compound 8
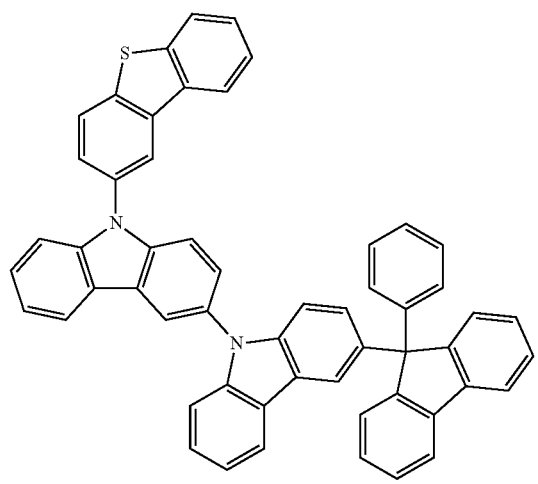 [SMILES: c1ccc(C2(c3ccc4c(c3)c3ccccc3n4-c3ccc4c(c3)c3ccccc3n4-c3ccc4sc5ccccc5c4c3)c3ccccc3-c3ccccc32)cc1]
8
Compound 13
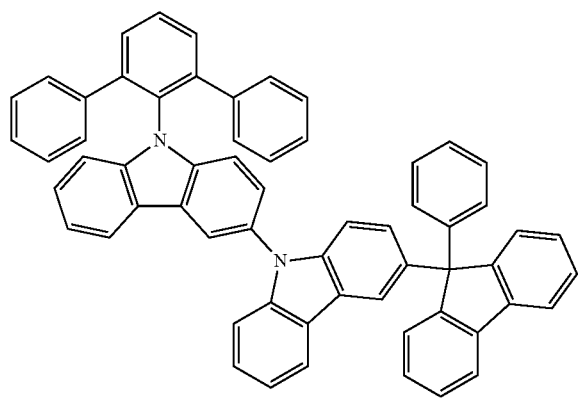 [SMILES: c1ccc(-c2cccc(-c3ccccc3)c2-n2c3ccccc3c3cc(-n4c5ccccc5c5cc(C6(c7ccccc7)c7ccccc7-c7ccccc76)ccc54)ccc32)cc1]
13

TABLE 2-continued
Compound 15
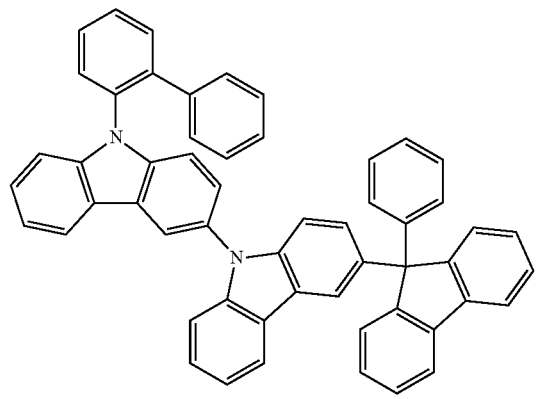 [SMILES: c1ccc(-c2ccccc2-n2c3ccccc3c3cc(-n4c5ccccc5c5cc(C6(c7ccccc7)c7ccccc7-c7ccccc76)ccc54)ccc32)cc1]
15
Compound 16
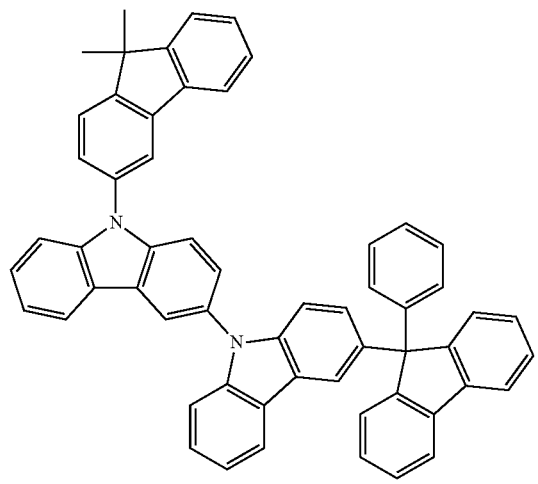 [SMILES: CC1(C)c2ccccc2-c2cc(-n3c4ccccc4c4cc(-n5c6ccccc6c6cc(C7(c8ccccc8)c8ccccc8-c8ccccc87)ccc65)ccc43)ccc21]
16
Compound 21
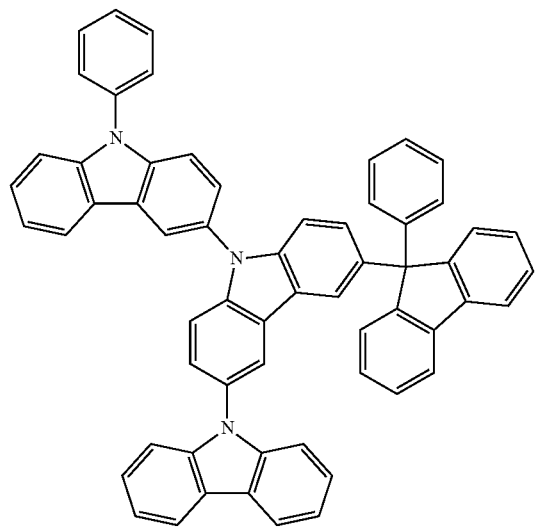 [SMILES: c1ccc(-n2c3ccccc3c3cc(-n4c5ccc(-n6c7ccccc7c7ccccc76)cc5c5cc(C6(c7ccccc7)c7ccccc7-c7ccccc76)ccc54)ccc32)cc1]
21

TABLE 2-continued
Compound 37
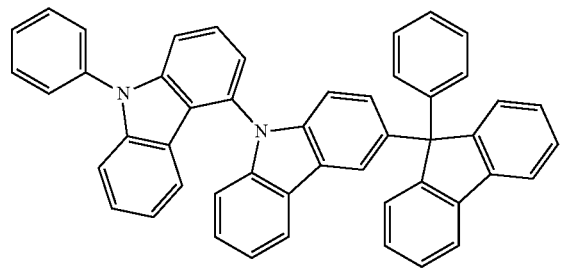 [SMILES: c1ccc(-n2c3ccccc3c3c(-n4c5ccccc5c5cc(C6(c7ccccc7)c7ccccc7-c7ccccc76)ccc54)cccc32)cc1]
37
Comparative Compound C1
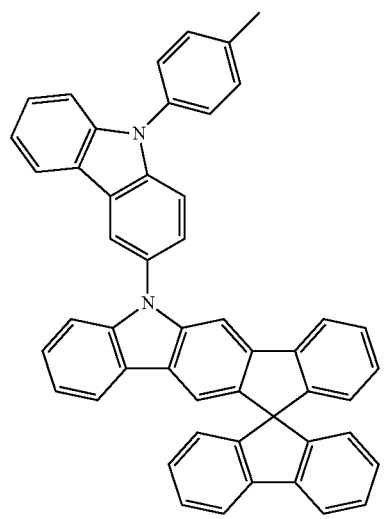 [SMILES: Cc1ccc(-n2c3ccccc3c3cc(-n4c5ccccc5c5cc6c(cc54)-c4ccccc4C64c5ccccc5-c5ccccc54)ccc32)cc1]
C1
Comparative Compound C2
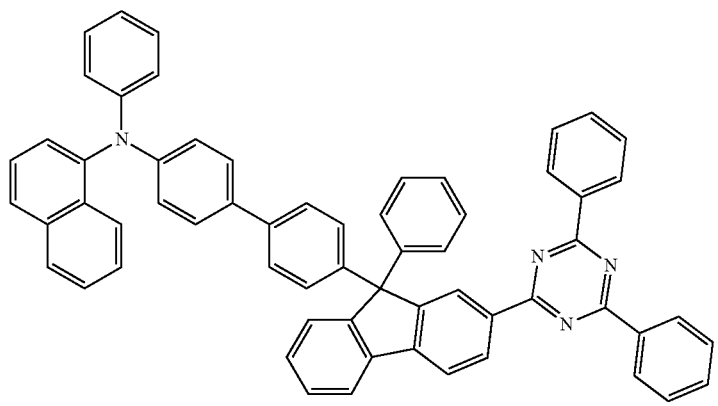 [SMILES: c1ccc(-c2nc(-c3ccccc3)nc(-c3ccc4c(c3)C(c3ccccc3)(c3ccc(-c5ccc(N(c6ccccc6)c6cccc7ccccc67)cc5)cc3)c3ccccc3-4)n2)cc1]
C2

TABLE 2-continued

Comparative Compound C3

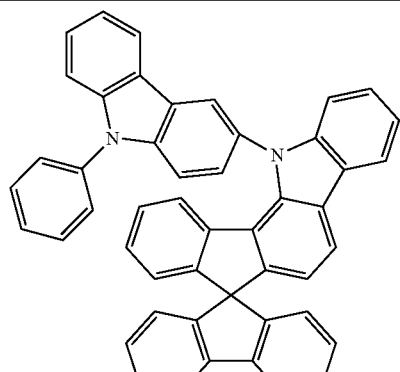

C3

Comparative Compound C4

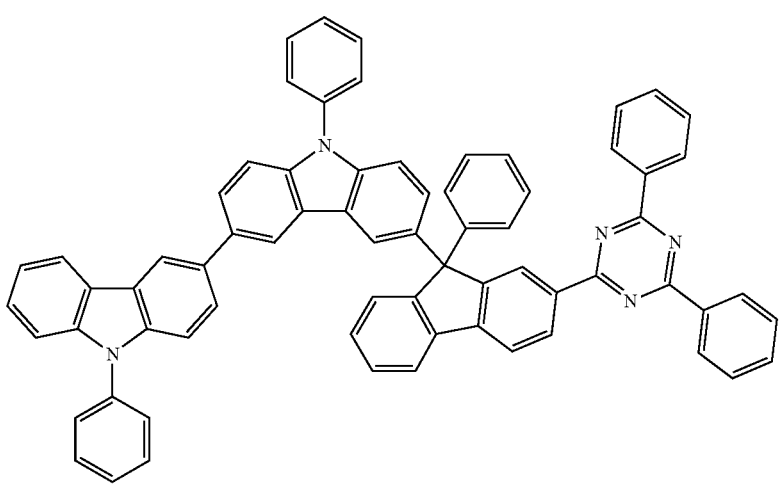 [SMILES: c1ccc(-c2nc(-c3ccccc3)nc(-c3ccc4c(c3)C(c3ccccc3)(c3ccc5c(c3)c3cc(-c6ccc7c(c6)c6ccccc6n7-c6ccccc6)ccc3n5-c3ccccc3)c3ccccc3-4)n2)cc1]

C4

Evaluation of Energy Levels of Compounds

TABLE 3

| Division | Light-emitting material | Driving voltage (V) | Efficiency (Cd/A) | Maximum quantum efficiency (%) | Maximum emission wavelength (nm) |
|---|---|---|---|---|---|
| Example 1 | Compound 1 | 4.9 | 23.1 | 22.5 | 460 |
| Example 2 | Compound 2 | 4.8 | 21.7 | 21.8 | 462 |
| Example 3 | Compound 4 | 4.6 | 22.4 | 21.0 | 464 |
| Example 4 | Compound 5 | 4.7 | 20.5 | 20.2 | 462 |
| Example 5 | Compound 8 | 4.6 | 21.6 | 19.5 | 463 |
| Example 6 | Compound 13 | 4.9 | 20.7 | 20.2 | 462 |
| Example 7 | Compound 15 | 4.6 | 21.3 | 21.1 | 461 |
| Example 8 | Compound 16 | 4.6 | 20.1 | 20.0 | 460 |
| Example 9 | Compound 21 | 4.5 | 23.5 | 23.1 | 465 |
| Example 10 | Compound 37 | 5.0 | 19.7 | 21.5 | 461 |
| Comparative Example 1 | Compound C1 | 5.0 | 19.3 | 19.3 | 468 |
| Comparative Example 2 | Compound C2 | 5.1 | 17.2 | 18.0 | 467 |
| Comparative Example 3 | Compound C3 | 4.9 | 17.5 | 17.8 | 465 |
| Comparative Example 4 | Compound C4 | 4.6 | 18.2 | 17.8 | 466 |

Referring to the results of Table 3, the electroluminescence devices of Example 1 to Example 10 and the electroluminescence devices of Comparative Example 1 to Comparative Example 4 may each emit light in a blue wavelength region. It could be confirmed that the electroluminescence devices of Example 1 to Example 10 showed lower average values of driving voltages, higher emission efficiencies and higher maximum quantum efficiencies when compared with the electroluminescence devices of Comparative Example 1 to Comparative Example 4. Comparative Compounds C1 to C3 each include the structure of a polycyclic compound including a fluorene group skeleton and a carbazole group skeleton but do not disclose a structure in which a bis carbazole group is substituted at a fluorene group as in the polycyclic compound of the present disclosure.

Comparative Compound C4 includes a first carbazole group substituted at carbon at position 9 of a fluorene group, and a second carbazole group substituted at the first carbazole group. However, the second carbazole group is connected with a carbon atom at position 6 of the first carbazole group. This is different from the structure of the present disclosure, wherein the polycyclic compound includes a fluorene group, a first carbazole group is substituted at the fluorene group, and a second carbazole group is substituted at the nitrogen atom of the first carbazole group.

The polycyclic compound of one or more embodiments of the present disclosure includes a fluorene group, a phenyl group and a first carbazole group directly connected at carbon at position 9 of the fluorene group, and a second carbazole group directly connected with the nitrogen atom at position 9 of the first carbazole group. In addition, at the nitrogen atom at position 9 of the second carbazole group, an aryl group, a heteroaryl group, etc., may be connected, and steric hindrance effects of the compound may be further increased, and hole transport capacity may be further improved.

The electroluminescence device according to one or more embodiments of the present disclosure includes the polycyclic compound of one or more embodiments in at least one of an emission layer or a hole transport region, and may have a reduced device driving voltage and excellent emission efficiency.

The electroluminescence device according to one or more embodiments of the present disclosure may have excellent (e.g., high) emission efficiency.

Although the embodiments of the present disclosure have been described, it is understood that the present invention should not be limited to these embodiments but various changes and modifications can be made by one ordinary skilled in the art within the spirit and scope of the present disclosure as hereinafter claimed by the following claims and their equivalents.

What is claimed is:
1. An electroluminescence device, comprising:
a first electrode;
a second electrode facing the first electrode; and
a plurality of organic layers between the first electrode and the second electrode,
wherein at least one organic layer selected from among the plurality of organic layers comprises a polycyclic compound, and
the polycyclic compound comprises:
a substituted or unsubstituted fluorene group;
a substituted or unsubstituted phenyl group connected with a carbon atom at position 9 of the substituted or unsubstituted fluorene group;
a substituted or unsubstituted first carbazole group connected with the carbon atom at position 9 of the substituted or unsubstituted fluorene group; and
a substituted or unsubstituted second carbazole group connected with a nitrogen atom of the substituted or unsubstituted first carbazole group,
wherein the substituted first carbazole group is substituted with a substituted or unsubstituted fourth carbazole group, a substituted or unsubstituted dibenzofuran group, a substituted or unsubstituted dibenzothiophene group, or a biphenyl group.

2. The electroluminescence device of claim 1, wherein the substituted or unsubstituted phenyl group is directly connected with the carbon atom at position 9 of the substituted or unsubstituted fluorene group.

3. The electroluminescence device of claim 1, wherein the substituted or unsubstituted first carbazole group is directly connected with the carbon atom at position 9 of the substituted or unsubstituted fluorene group.

4. The electroluminescence device of claim 1, wherein the substituted or unsubstituted second carbazole group is directly connected with the nitrogen atom of the substituted or unsubstituted first carbazole group.

5. The electroluminescence device of claim 1, wherein a substituted or unsubstituted third carbazole group is connected with a nitrogen atom of the substituted or unsubstituted second carbazole group.

6. The electroluminescence device of claim 1, wherein the substituted or unsubstituted phenyl group and the substituted or unsubstituted first carbazole group do not form a ring with each other.

7. The electroluminescence device of claim 1, wherein the plurality of organic layers comprise a hole transport region, an emission layer, and an electron transport region, and the polycyclic compound is in the emission layer.

8. The electroluminescence device of claim 7, wherein the emission layer is to emit at least one of fluorescence, phosphorescence, or thermally activated delayed fluorescence.

9. The electroluminescence device of claim 7, wherein the emission layer comprises a host and a dopant, and the host comprises the polycyclic compound.

10. An electroluminescence device, comprising:
a first electrode;
a second electrode facing the first electrode; and
a plurality of organic layers between the first electrode and the second electrode, the plurality of organic layers comprising a hole transport region, an emission layer, and an electron transport region,
wherein the emission layer comprises a polycyclic compound, and
the polycyclic compound comprises:
a substituted or unsubstituted fluorene group;
a substituted or unsubstituted phenyl group connected with a carbon atom at position 9 of the substituted or unsubstituted fluorene group;
a substituted or unsubstituted first carbazole group connected with the carbon atom at position 9 of the substituted or unsubstituted fluorene group; and
a substituted or unsubstituted second carbazole group connected with a nitrogen atom of the substituted or unsubstituted first carbazole group, and
wherein the emission layer is to emit light having a central wavelength of about 420 nm to about 470 nm.

11. An electroluminescence device, comprising:
a first electrode;
a second electrode facing the first electrode; and
a plurality of organic layers between the first electrode and the second electrode, wherein at least one organic layer selected from among the plurality of organic layers comprises a polycyclic compound represented by Formula 1:

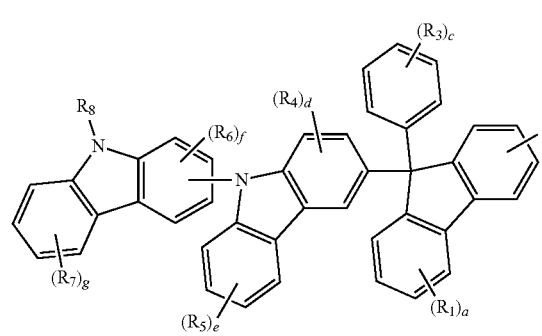

Formula 1 and in Formula 1, $R_1$ to $R_4$ and $R_6$ to $R_8$ are each independently a hydrogen atom, a deuterium atom, a halogen atom, a cyano group, a substituted or unsubstituted silyl group, a substituted or unsubstituted alkyl group of 1 to 30 carbon atoms, a substituted or unsubstituted alkenyl group of 2 to 30 carbon atoms, a substituted or unsubstituted amine group, a substituted or unsubstituted aryl group of 6 to 30 ring-forming carbon atoms, or a substituted or unsubstituted heteroaryl group of 2 to 30 ring-forming carbon atoms, $R_5$ is a hydrogen atom, a deuterium atom, a substituted or unsubstituted carbazole group, a substituted or unsubstituted dibenzofuran group, a substituted or unsubstituted dibenzothiophene group, or a biphenyl group, "a" and "b" are each independently an integer of 0 to 4, "c" is an integer of 0 to 5, "d" is an integer of 0 to 3, "e" is an integer of 0 to 4, "f" is an integer of 0 to 3, and "g" is an integer of 0 to 4.

12. The electroluminescence device of claim 11, wherein $R_1$ to $R_4$, $R_6$, and $R_7$ are each independently a hydrogen atom or a deuterium atom.

13. The electroluminescence device of claim 11, wherein $R_5$ is a substituted or unsubstituted carbazole group, a substituted or unsubstituted dibenzofuran group, or a substituted or unsubstituted dibenzothiophene group.

14. The electroluminescence device of claim 11, wherein $R_8$ is a substituted or unsubstituted aryl group of 6 to 30 ring-forming carbon atoms, or a substituted or unsubstituted heteroaryl group of 2 to 30 ring-forming carbon atoms.

15. The electroluminescence device of claim 11, wherein Formula 1 is represented by Formula 1-1:

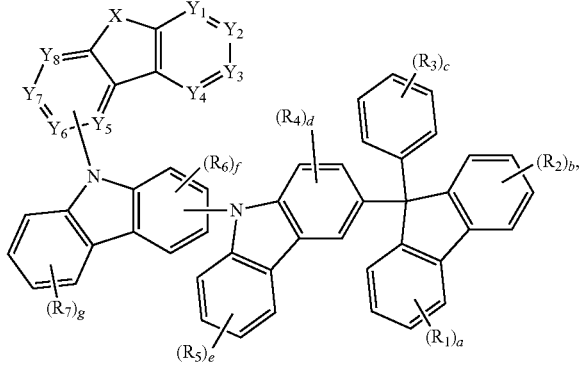

Formula 1-1 and in Formula 1-1,

X is $NAr_1$, O or S, $Y_1$ to $Y_8$ are each independently $CR_a$ or N, $Ar_1$ is a substituted or unsubstituted aryl group of 6 to 30 ring-forming carbon atoms, or a substituted or unsubstituted heteroaryl group of 2 to 30 ring-forming carbon atoms, $R_a$ is a hydrogen atom, a deuterium atom, a halogen atom, a cyano group, a substituted or unsubstituted silyl group, a substituted or unsubstituted alkyl group of 1 to 30 carbon atoms, a substituted or unsubstituted alkenyl group of 2 to 30 carbon atoms, a substituted or unsubstituted amine group, a substituted or unsubstituted aryl group of 6 to 30 ring-forming carbon atoms, or a substituted or unsubstituted heteroaryl group of 2 to 30 ring-forming carbon atoms, and $R_1$ to $R_7$, and "a" to "g" are the same as defined in Formula 1.

16. The electroluminescence device of claim 11, wherein Formula 1 is represented by any one selected from among Formula 2-1 to Formula 2-3:

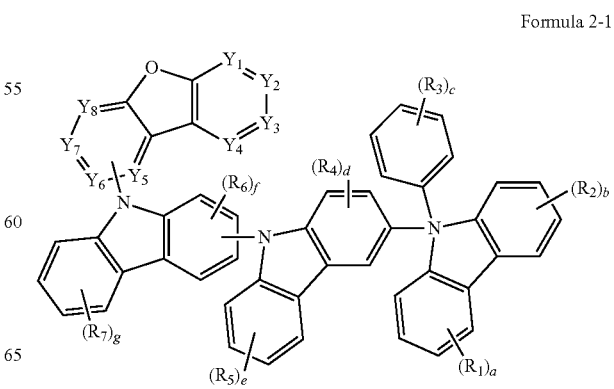

Formula 2-1

-continued

Formula 2-2

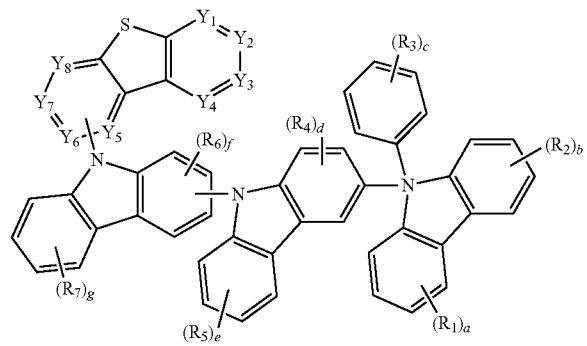

Formula 2-3

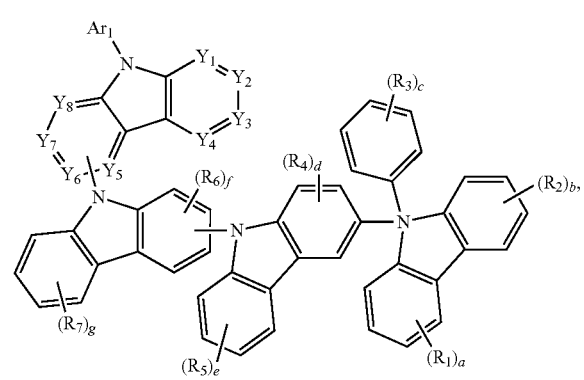

and in Formula 2-1 to Formula 2-3, $Y_1$ to $Y_8$ are each independently $CR_a$ or N, $Ar_1$ is a substituted or unsubstituted aryl group of 6 to 30 ring-forming carbon atoms, or a substituted or unsubstituted heteroaryl group of 2 to 30 ring-forming carbon atoms, $R_a$ is a hydrogen atom, a deuterium atom, a halogen atom, a cyano group, a substituted or unsubstituted silyl group, a substituted or unsubstituted alkyl group of 1 to 30 carbon atoms, a substituted or unsubstituted alkenyl group of 2 to 30 carbon atoms, a substituted or unsubstituted amine group, a substituted or unsubstituted aryl group of 6 to 30 ring-forming carbon atoms, or a substituted or unsubstituted heteroaryl group of 2 to 30 ring-forming carbon atoms, and $R_1$ to $R_7$, and "a" to "g" are the same as defined in Formula 1.

17. The electroluminescence device of claim 16, wherein $Ar_1$ is a substituted or unsubstituted phenyl group.

18. The electroluminescence device of claim 11, wherein Formula 1 is represented by Formula 3-1 or Formula 3-2:

Formula 3-1

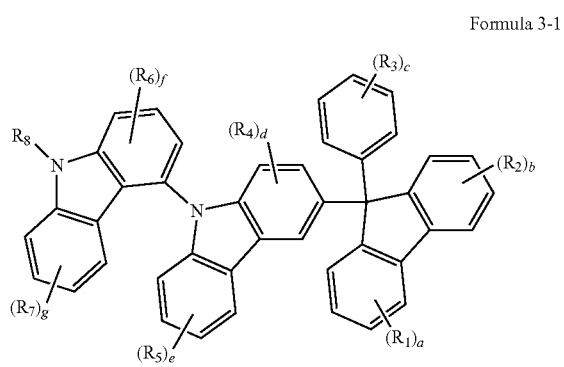

Formula 3-2

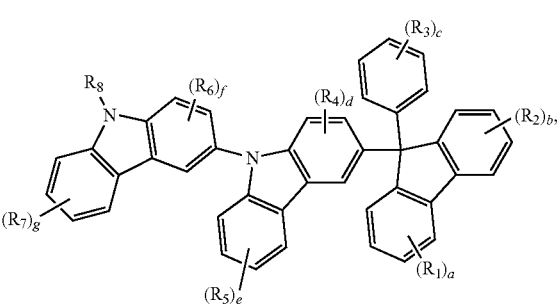

and in Formula 3-1 and Formula 3-2, $R_1$ to $R_8$, and "a" to "g" are the same as defined in Formula 1.

19. The electroluminescence device of claim 11, wherein Formula 1 is represented by Formula 4-1:

Formula 4-1

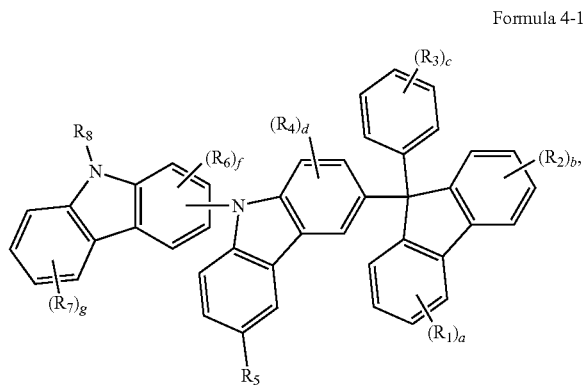

and in Formula 4-1, $R_1$ to $R_8$, "a" to "d", and "f" to "g" are the same as defined in Formula 1.

20. The electroluminescence device of claim 11, wherein the polycyclic compound represented by Formula 1 comprises at least one selected from among compounds represented in Compound Group 1:

Compound Group 1
1
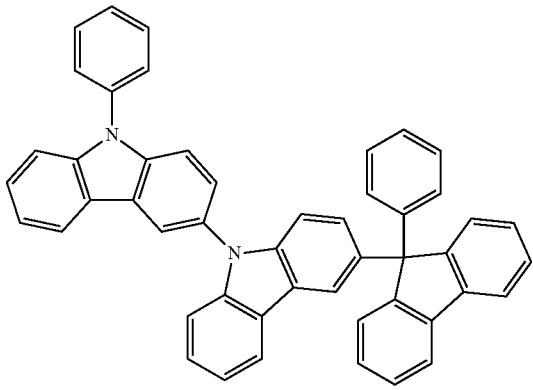
2
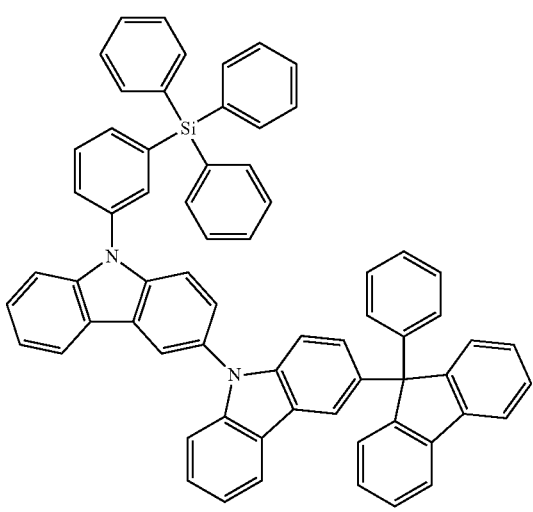
3
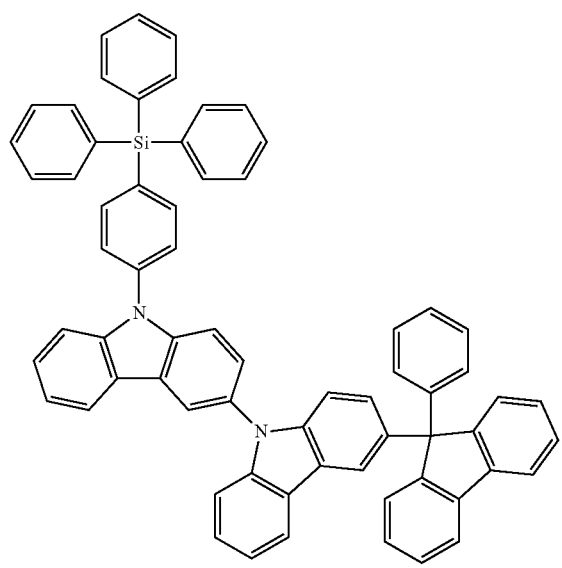
4
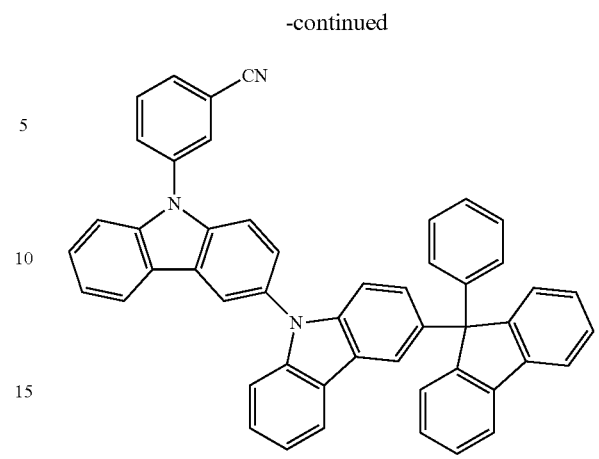
5
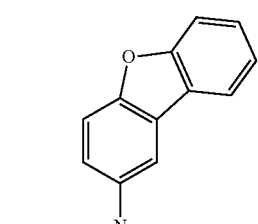
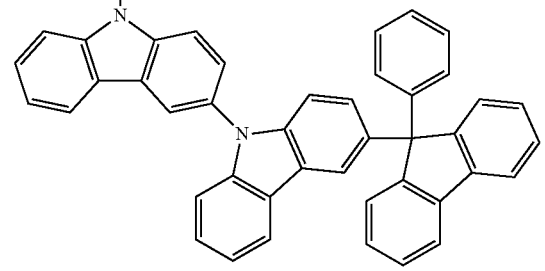
6
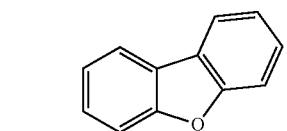
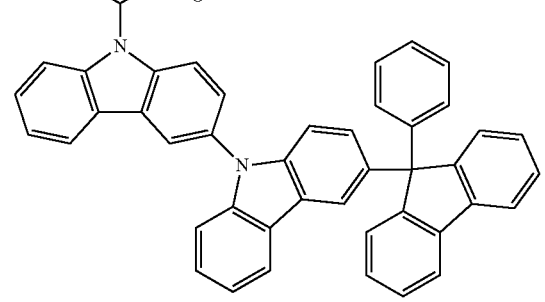

115
-continued
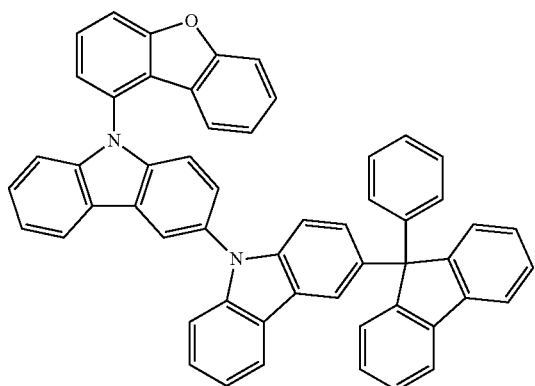
7
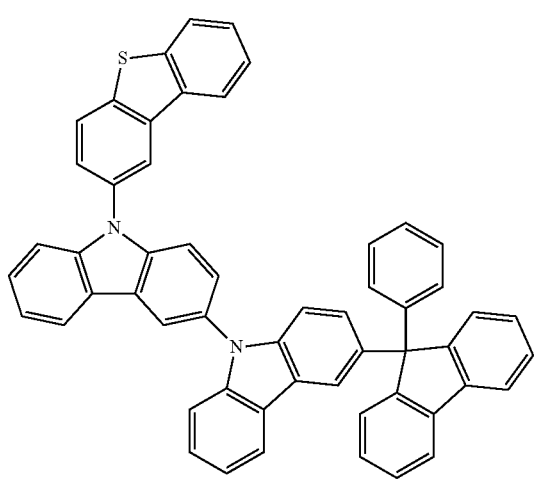
8
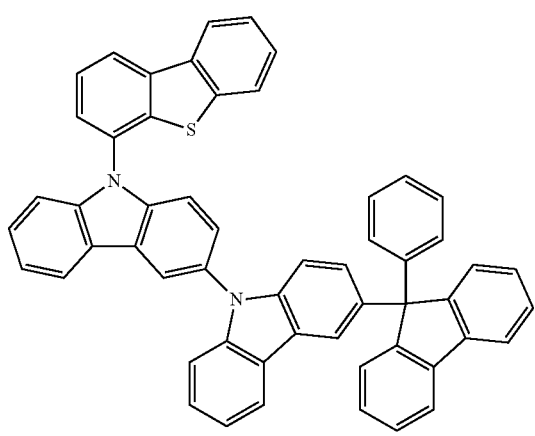
9
116
-continued
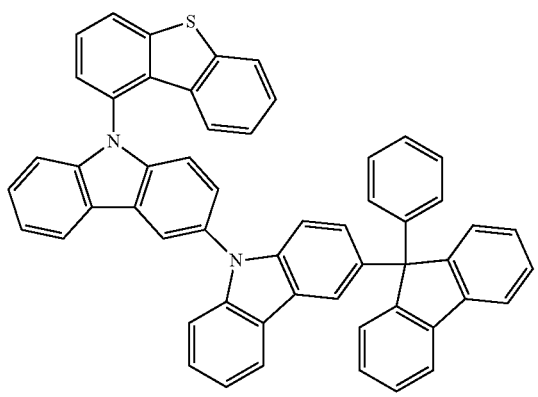
10
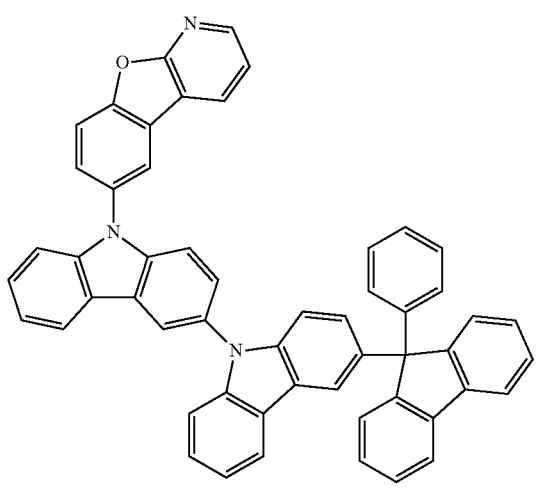
11
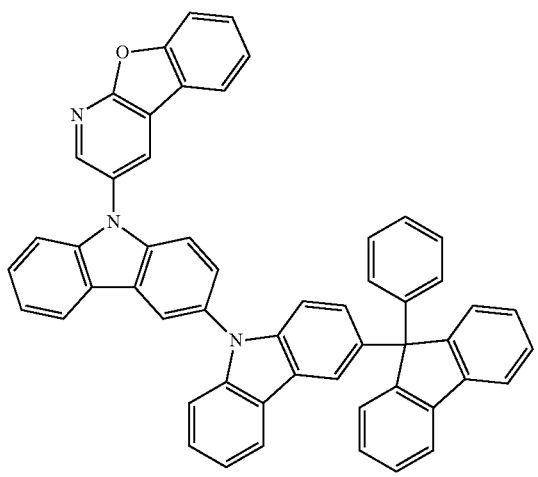
12

13
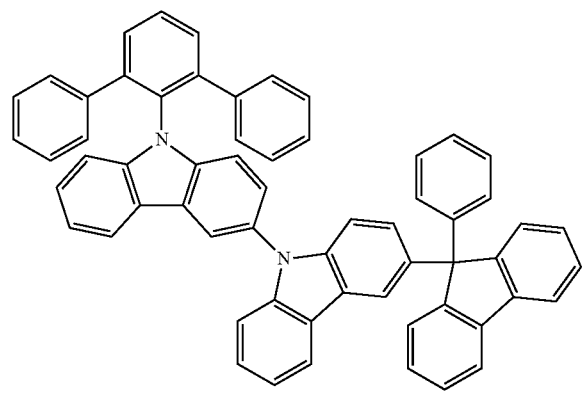
14
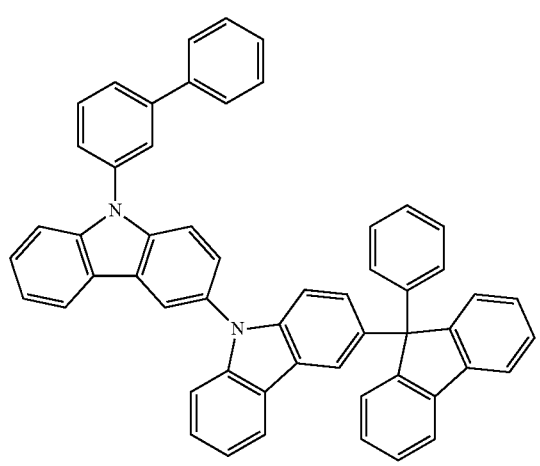
16
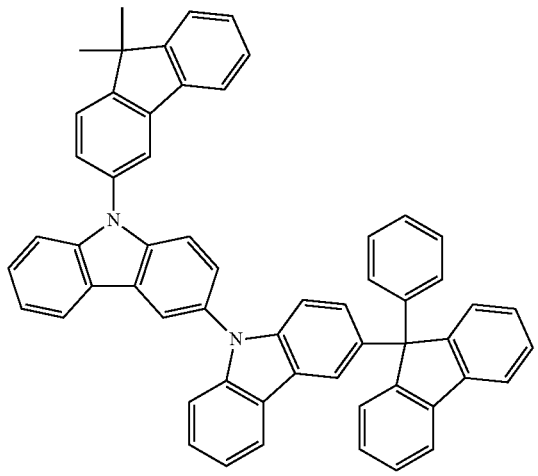
17
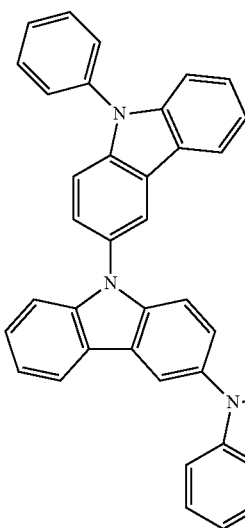
18
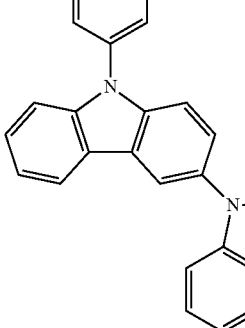

19
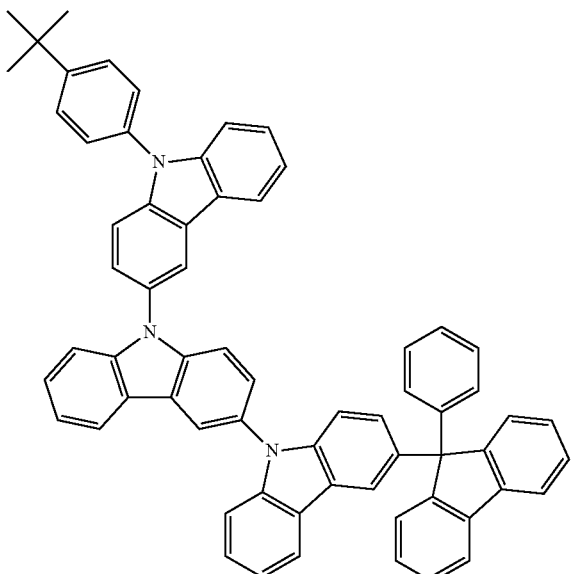
21
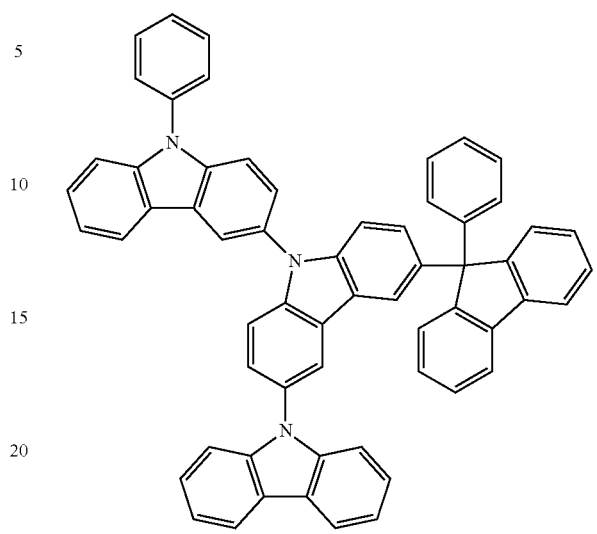
20
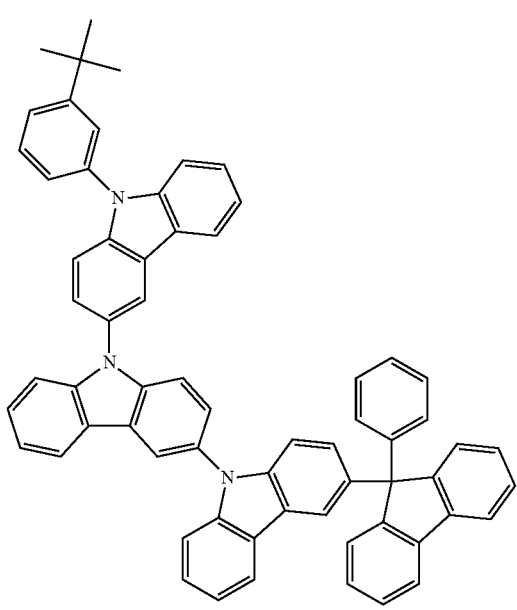
22
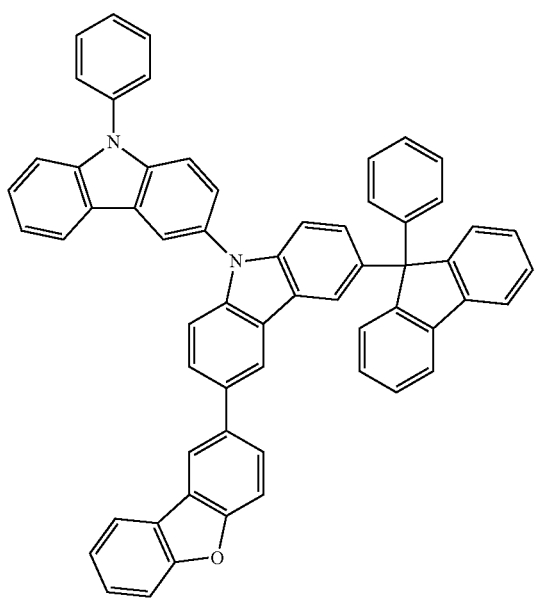

-continued
23
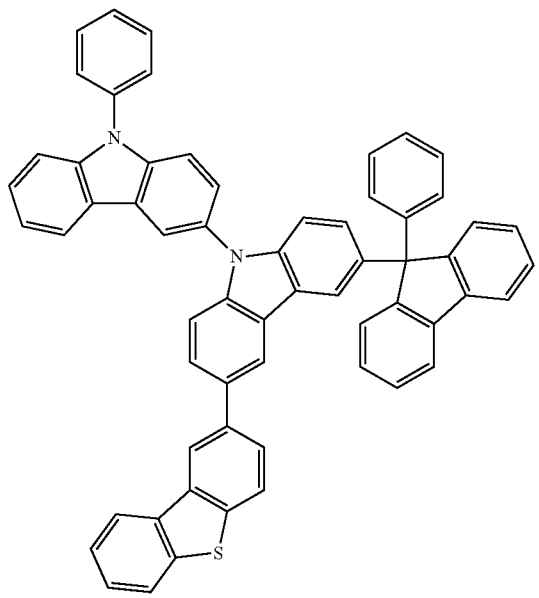
24
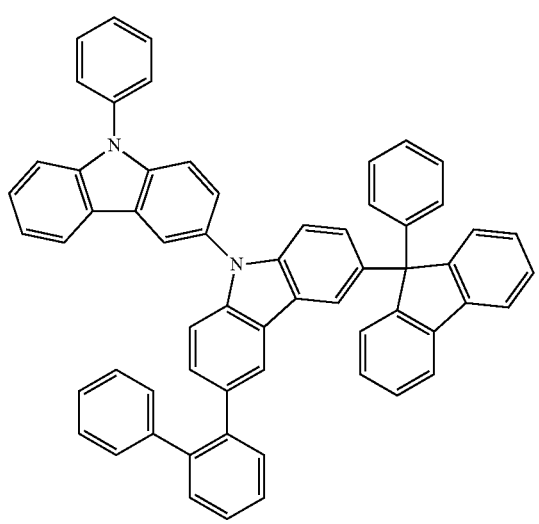
25
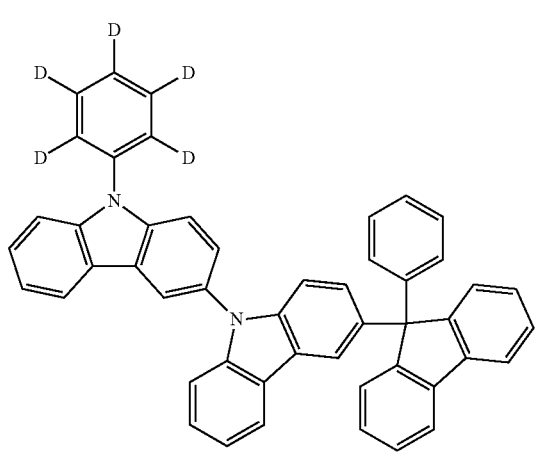
-continued
26
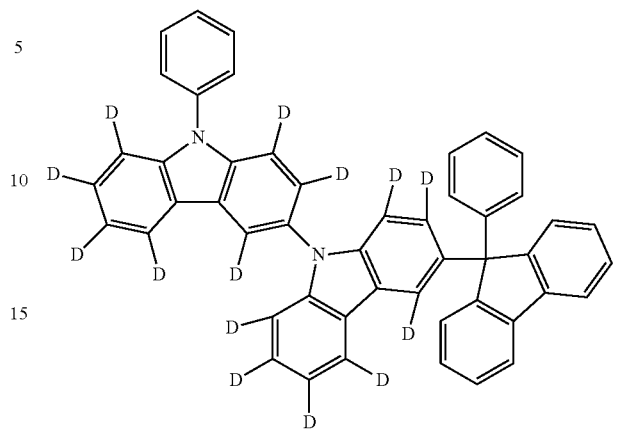
27
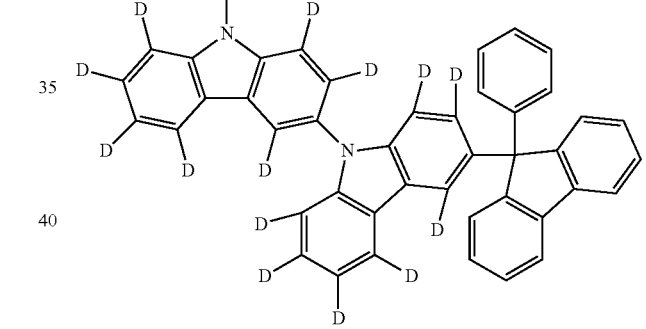
28
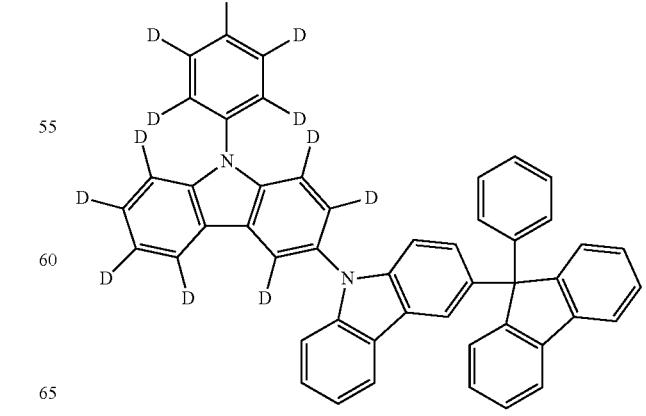

29
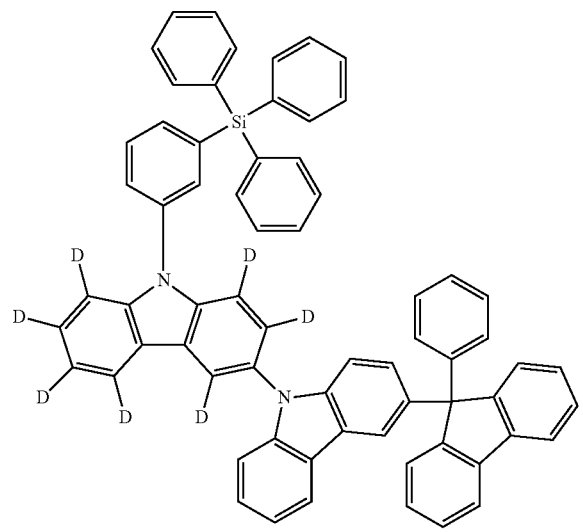
30
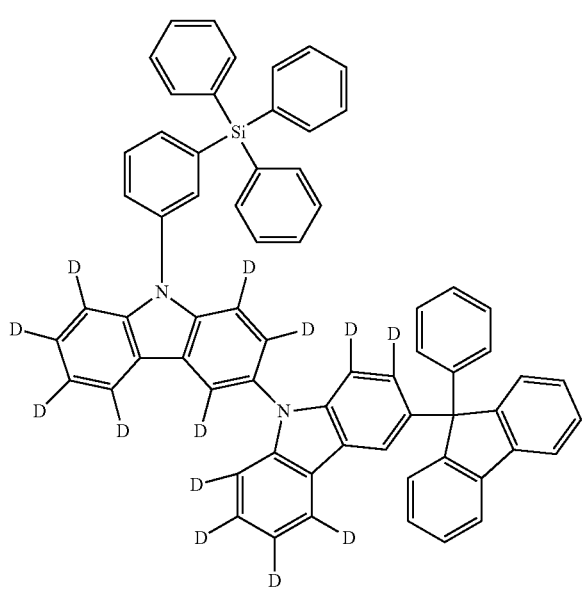
31
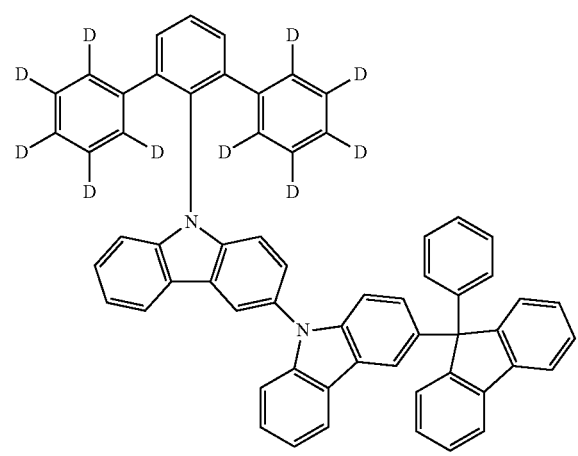
32
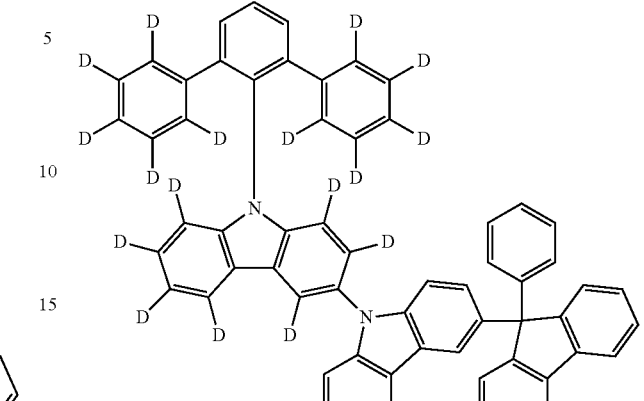
33
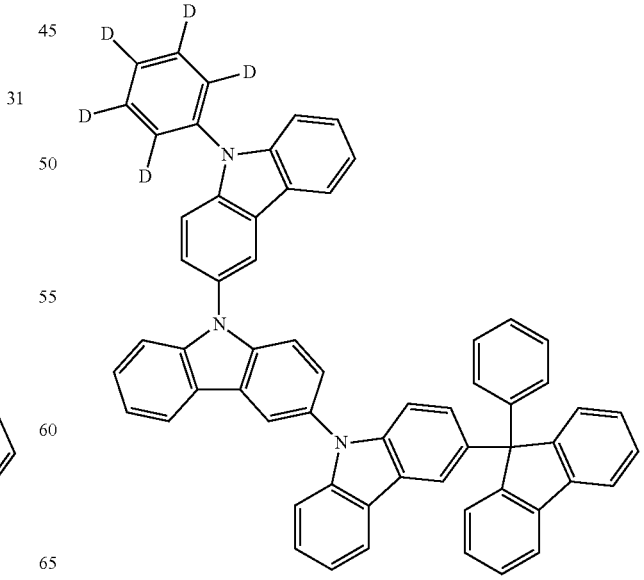
34

35
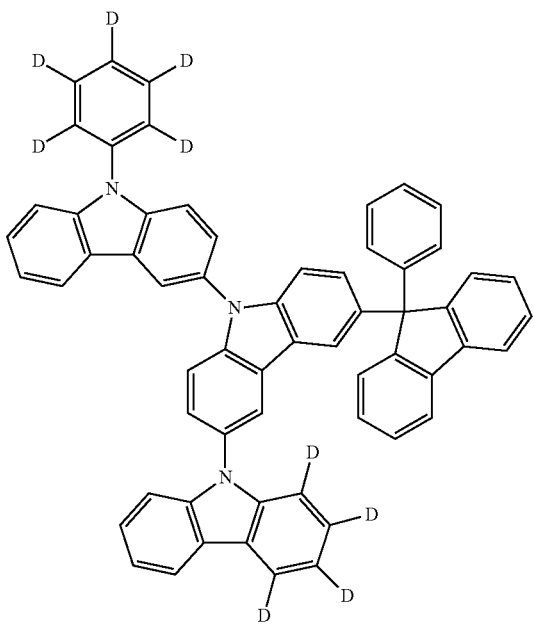
36
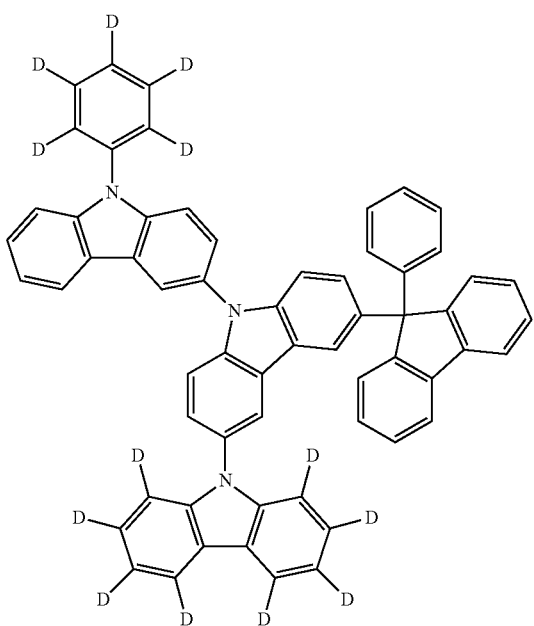
37
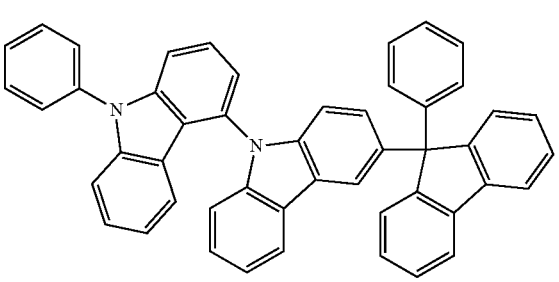
38
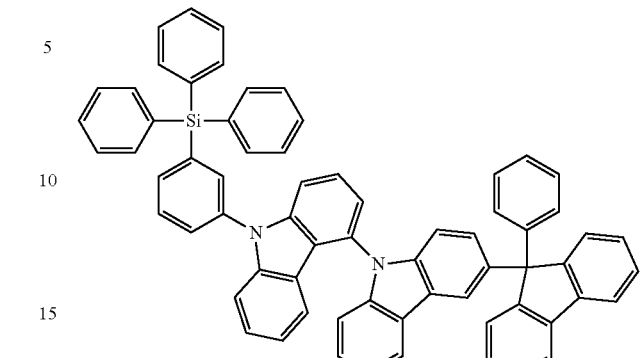
39
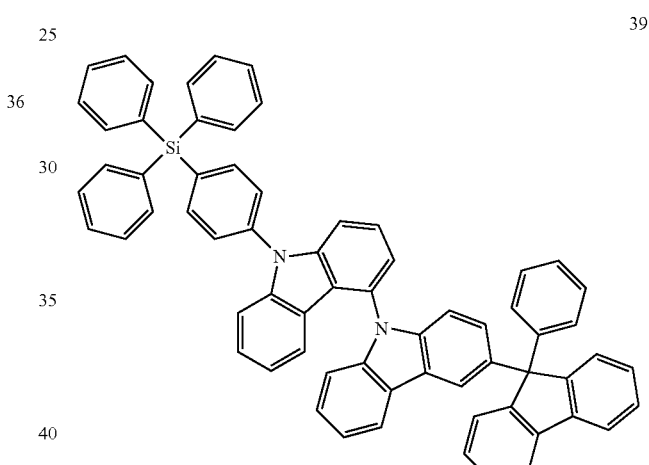
40
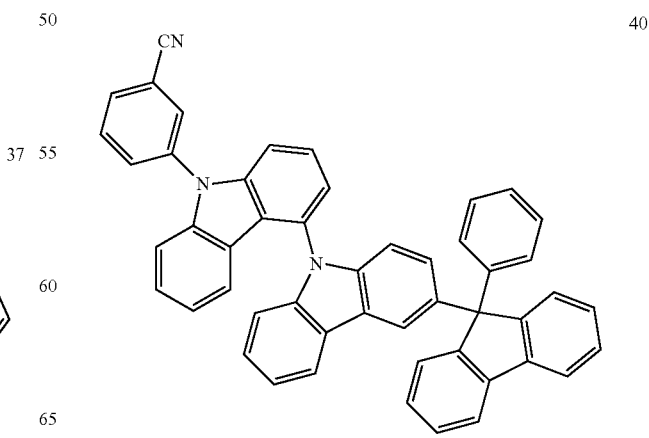

41
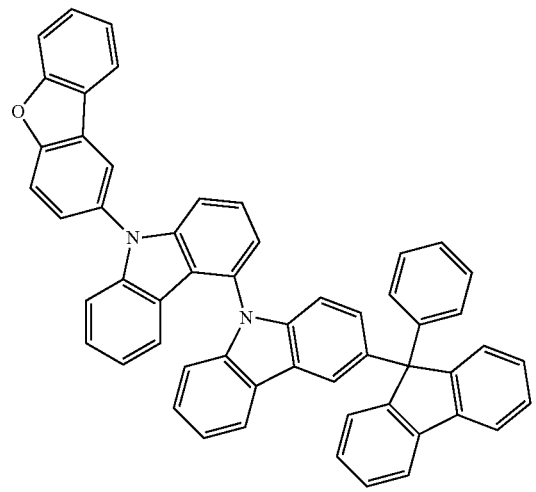
42
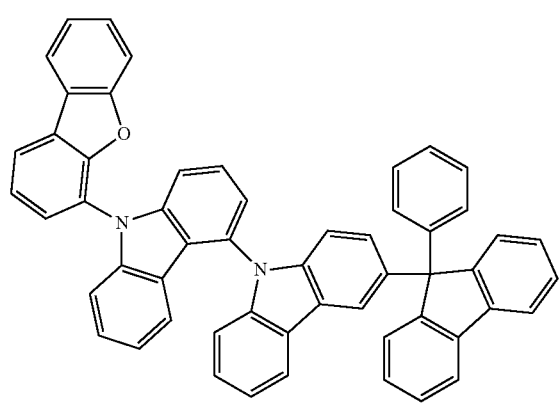
43
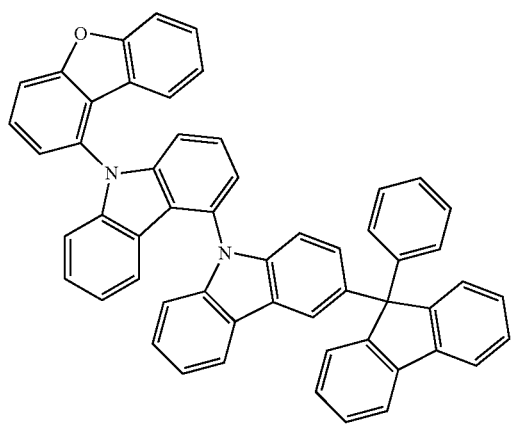
44
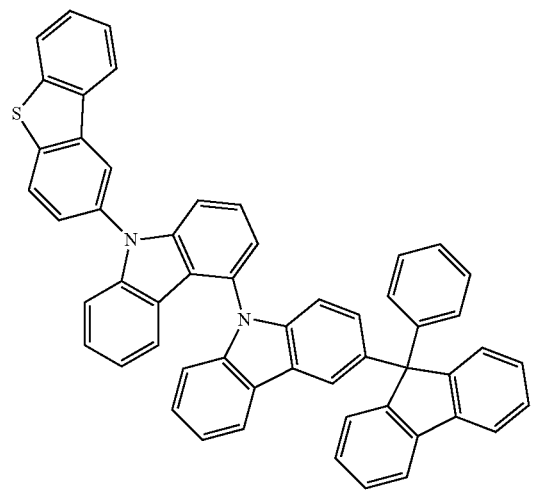
45
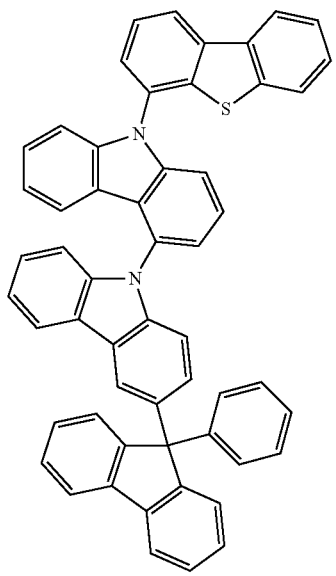
46
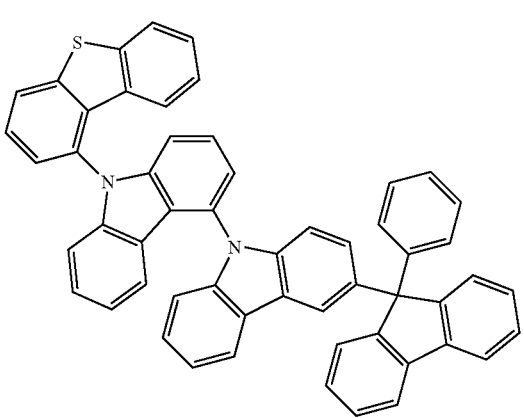

47
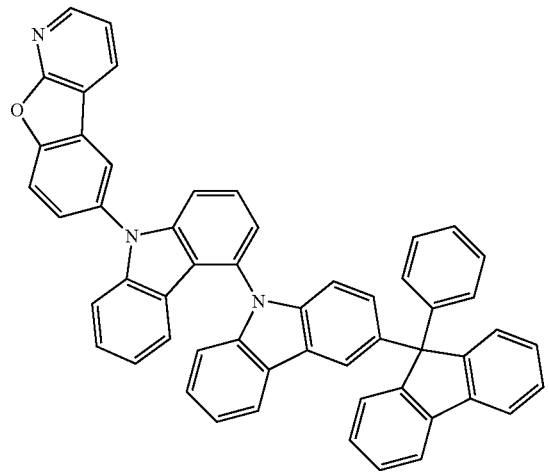
48
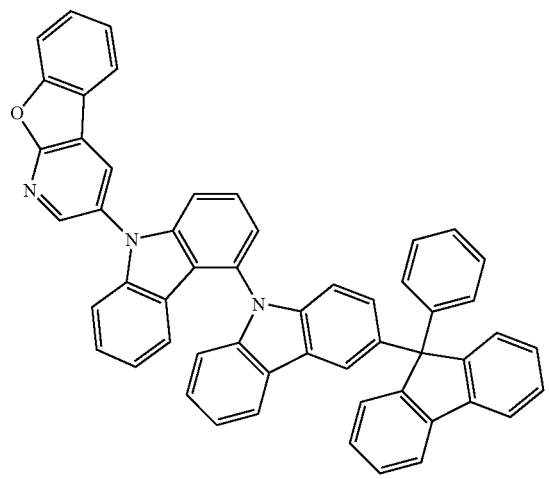
49
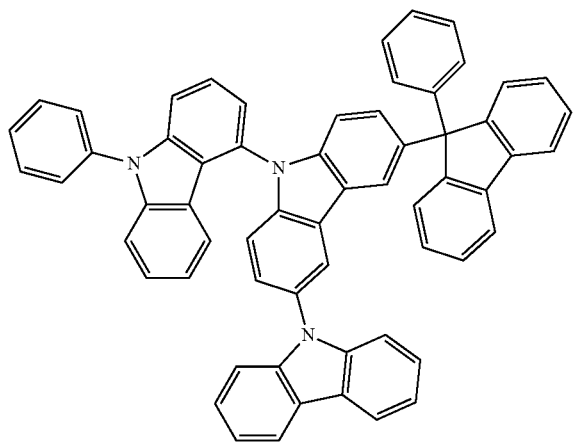
50
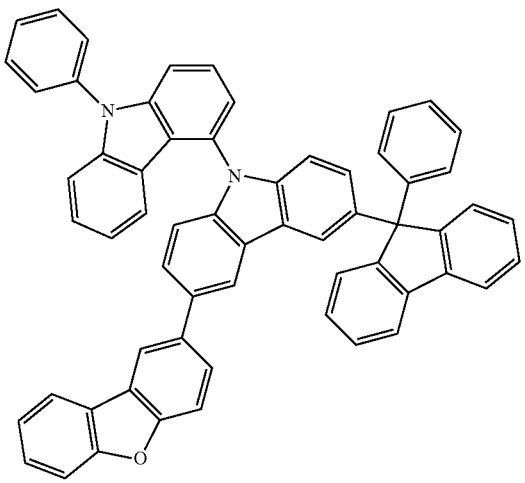
51
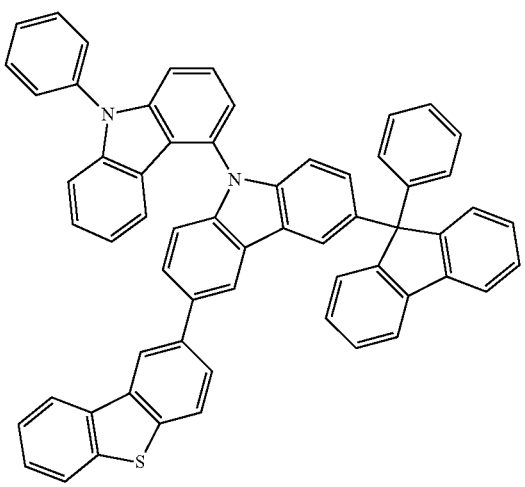
52
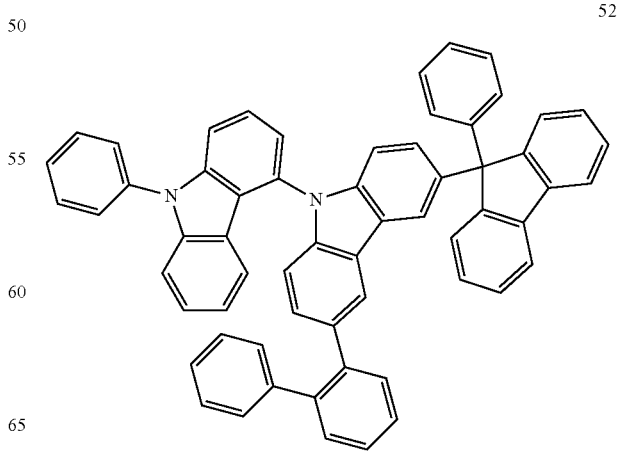

53
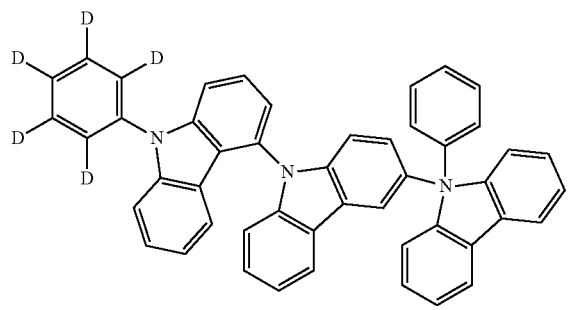
54
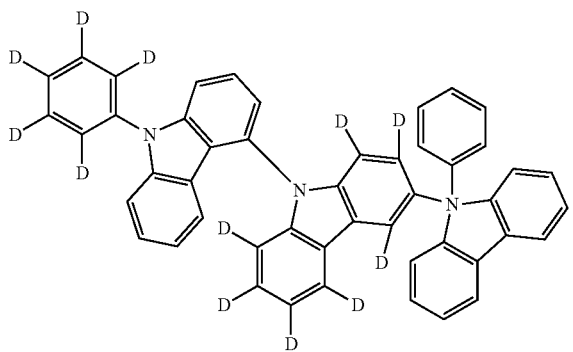
55
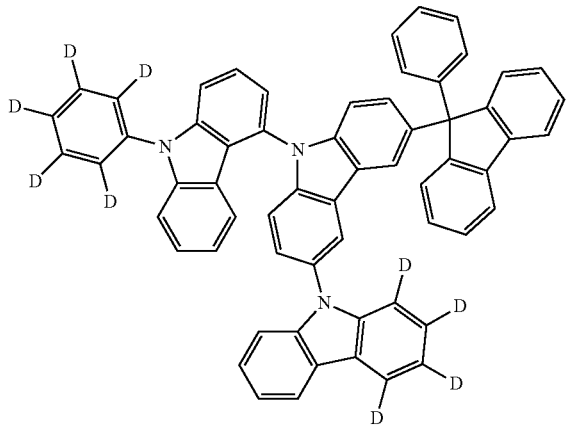
56
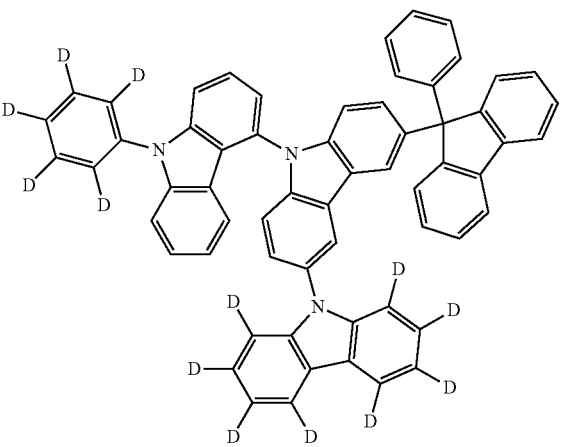
* * * * *